(12) United States Patent
Kinoshita

(10) Patent No.: US 11,300,877 B2
(45) Date of Patent: Apr. 12, 2022

(54) RADIATION-SENSITIVE RESIN COMPOSITION, RESIST PATTERN-FORMING METHOD AND ACID DIFFUSION CONTROL AGENT

(71) Applicant: JSR CORPORATION, Tokyo (JP)

(72) Inventor: Natsuko Kinoshita, Tokyo (JP)

(73) Assignee: JSR Corporation, Tokyo (JP)

( * ) Notice: Subject to any disclaimer, the term of this patent is extended or adjusted under 35 U.S.C. 154(b) by 13 days.

(21) Appl. No.: 16/030,227

(22) Filed: Jul. 9, 2018

(65) Prior Publication Data

US 2018/0321585 A1 Nov. 8, 2018

Related U.S. Application Data

(63) Continuation of application No. PCT/JP2016/088799, filed on Dec. 26, 2016.

(30) Foreign Application Priority Data

Jan. 13, 2016 (JP) ................. 2016-004820

(51) Int. Cl.
| | | |
|---|---|---|
| *G03F 7/004* | (2006.01) | |
| *G03F 7/039* | (2006.01) | |
| *G03F 7/30* | (2006.01) | |
| *G03F 7/38* | (2006.01) | |
| *C07D 233/64* | (2006.01) | |
| *C07D 235/02* | (2006.01) | |
| *C07D 235/18* | (2006.01) | |
| *G03F 7/038* | (2006.01) | |
| *C08F 220/16* | (2006.01) | |
| *G03F 7/16* | (2006.01) | |
| *G03F 7/20* | (2006.01) | |
| *G03F 7/32* | (2006.01) | |
| *C08F 220/28* | (2006.01) | |
| *C08F 220/18* | (2006.01) | |
| *C08F 220/22* | (2006.01) | |

(52) U.S. Cl.
CPC ......... *G03F 7/0045* (2013.01); *C07D 233/64* (2013.01); *C07D 235/02* (2013.01); *C07D 235/18* (2013.01); *C08F 220/16* (2013.01); *C08F 220/28* (2013.01); *G03F 7/038* (2013.01); *G03F 7/039* (2013.01); *G03F 7/0397* (2013.01); *G03F 7/162* (2013.01); *G03F 7/168* (2013.01); *G03F 7/2006* (2013.01); *G03F 7/2041* (2013.01); *G03F 7/30* (2013.01); *G03F 7/322* (2013.01); *G03F 7/38* (2013.01); *C08F 220/1806* (2020.02); *C08F 220/1807* (2020.02); *C08F 220/1808* (2020.02); *C08F 220/1809* (2020.02); *C08F 220/1811* (2020.02); *C08F 220/1812* (2020.02); *C08F 220/1818* (2020.02); *C08F 220/22* (2013.01); *C08F 220/281* (2020.02); *C08F 220/283* (2020.02); *C08F 2800/10* (2013.01)

(58) Field of Classification Search
CPC .... G03F 7/0392; G03F 7/0397; G03F 7/0045; G03F 7/38; C07D 233/64; C07D 235/02; C07D 235/18

See application file for complete search history.

(56) References Cited

U.S. PATENT DOCUMENTS

| | | | |
|---|---|---|---|
| 4,910,122 A | 3/1990 | Arnold et al. | |
| 5,744,537 A | 4/1998 | Brunsvold et al. | |
| 6,136,500 A | 10/2000 | Kobayashi et al. | |
| RE41,580 E * | 8/2010 | Hasegawa ............ | C07D 307/00 430/270.1 |
| 10,031,419 B2 * | 7/2018 | Takizawa ................ | G03F 7/039 |
| 2002/0051933 A1 | 5/2002 | Kodama et al. | |
| 2006/0008736 A1 * | 1/2006 | Kanda ................... | G06F 3/0395 430/270.1 |
| 2006/0147836 A1 * | 7/2006 | Hatakeyama ......... | G06F 7/0046 430/921 |
| 2007/0015080 A1 * | 1/2007 | Toukhy ................. | G03F 7/0392 430/270.1 |

(Continued)

FOREIGN PATENT DOCUMENTS

| | | |
|---|---|---|
| EP | 0159428 A1 | 10/1985 |
| JP | S59-93448 A | 5/1984 |

(Continued)

OTHER PUBLICATIONS

International Search Report dated Mar. 28, 2017 in PCT/JP2016/088799 (w/ English translation).

(Continued)

*Primary Examiner* — John S Chu

(74) *Attorney, Agent, or Firm* — Element IP, PLC

(57) ABSTRACT

A radiation-sensitive resin composition includes: a first polymer having a first structural unit that includes an acid-labile group; a radiation-sensitive acid generator; and a first compound capable of forming a salt through a structural change in a molecule thereof upon irradiation with a radioactive ray. Basicity of the first compound preferably changes upon irradiation with a radioactive ray. The first compound preferably generates an acid upon irradiation with a radioactive ray. The first compound is preferably represented by formula (1). In formula (1), $Ar^1$ represents a substituted or unsubstituted heteroarenediyl group having 4 to 30 ring atoms and having at least one nitrogen atom as a ring-constituting atom.

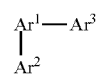

(1)

20 Claims, No Drawings

(56) References Cited

U.S. PATENT DOCUMENTS

| | | | | |
|---|---|---|---|---|
| 2008/0311514 | A1* | 12/2008 | Nakashima | G03F 7/0397 430/281.1 |
| 2011/0306743 | A1* | 12/2011 | Abe | G03O 1/73 526/219.6 |
| 2015/0338736 | A1* | 11/2015 | Kawabata | C07C 309/12 430/281.1 |
| 2015/0370170 | A1* | 12/2015 | Hirano | G03F 7/2041 430/17 |

FOREIGN PATENT DOCUMENTS

| | | |
|---|---|---|
| JP | H05-188598 A | 7/1993 |
| JP | H06-12452 B2 | 2/1994 |
| JP | H11-125907 A | 5/1999 |
| JP | 2002-122994 A | 4/2002 |
| JP | 2009-134088 A | 6/2009 |
| JP | 2010-061043 A | 3/2010 |
| JP | 2012-234038 A | 11/2012 |
| JP | 2015022074 A | 2/2015 |
| JP | 2015-068860 A | 4/2015 |
| JP | 2015163672 A | 9/2015 |
| TW | 201523134 A | 6/2015 |

OTHER PUBLICATIONS

Office Action dated Aug. 25, 2020 in Japanese Patent Application No. 2017-561573 (with English translation), 5 pages.
Office Action dated Jun. 30, 2020 in Taiwanese Patent Application No. 105144063 (with English translation), 9 pages.
Combined Office Action and Search Report dated Jan 6, 2021 in Chinese Patent Application No. 201680078761.6 (with English translation).
Kamil Skonieczny et al, "Photochemical Conversion of Phenanthro[9,10-d]imidazoles into π-Expanded Heterocycles", The Journal of Organic Chemistry, 80, 2015, pp. 5753-5763.
Office Action dated Mar. 16, 2021 in Japanese Patent Application No. 2017-561573 (with English translation), 5 pages.

* cited by examiner

RADIATION-SENSITIVE RESIN COMPOSITION, RESIST PATTERN-FORMING METHOD AND ACID DIFFUSION CONTROL AGENT

CROSS-REFERENCE TO RELATED APPLICATIONS

The present application is a continuation application of International Application No. PCT/JP2016/088799, filed Dec. 26, 2016, which claims priority to Japanese Patent Application No. 2016-004820, filed Jan. 13, 2016. The contents of these applications are incorporated herein by reference in their entirety.

BACKGROUND OF THE INVENTION

Field of the Invention

The present invention relates to a radiation-sensitive resin composition, a resist pattern-forming method and an acid diffusion control agent.

Discussion of the Background

A radiation-sensitive resin composition for use in microfabrication by lithography generates an acid upon irradiation with a radioactive ray such as an electromagnetic wave or a charged particle ray at a light-exposed region. A chemical reaction in which the acid serves as a catalyst causes the difference in rates of dissolution in a developer solution, between light-exposed regions and light-unexposed regions, whereby a resist pattern is formed on a substrate.

At present, miniaturization in resist pattern processing techniques has been attempted through use of a laser beam or electron beam having a shorter wavelength, and use of an immersion scanner and the like. There exist demands for such a radiation-sensitive resin composition to be able to provide not only a resist pattern formed with superior resolution but also superior lithography performances such as a LWR (Line Width Roughness) performance, a depth of focus and an inhibitory ability of defects, thereby enabling a highly accurate pattern to be formed at a high process yield. To meet these demands, a radiation-sensitive acid generator, an acid diffusion control agent and other components for use in the radiation-sensitive resin composition have been studied in detail on their types, molecular structures and the like. Known such an acid diffusion control agent includes a photodegradable base constituted with an onium salt compound containing an onium cation, and a carboxylic acid anion and/or a sulfonic acid anion (see, Japanese Unexamined Patent Application, Publication Nos. H11-125907, 2002-122994 and 2010-061043).

However, under current circumstances in which miniaturization of resist patterns has proceeded to a level for line widths of no greater than 45 nm, required levels for the aforementioned performances are further elevated. Moreover, contraction of the resist film during post exposure baking is recently needed to be smaller, and consequently, there exist demands for more improvements of various performances as the resist film described above. In addition, an improvement of storage stability is also rerequired.

SUMMARY OF THE INVENTION

According to an aspect of the present invention, a radiation-sensitive resin composition includes: a first polymer comprising a first structural unit that comprises an acid-labile group; a radiation-sensitive acid generator; and a first compound capable of forming a salt through a structural change in a molecule thereof upon irradiation with a radioactive ray. According to another aspect of the present invention, a resist pattern-forming method includes applying the radiation-sensitive resin composition on one face side of a substrate. The resist film obtained after the applying is exposed. The resist film exposed is developed.

According to further aspect of the present invention, an acid diffusion control agent includes a compound capable of forming a salt through a structural change in a molecule thereof upon irradiation with a radioactive ray.

DESCRIPTION OF THE EMBODIMENTS

According to one embodiment of the invention, a radiation-sensitive resin composition contains: a first polymer (hereinafter, may be also referred to as "(A) polymer" or "polymer (A)") having a first structural unit that includes an acid-labile group (hereinafter, may be also referred to as "structural unit (I)"); a radiation-sensitive acid generator (hereinafter, may be also referred to as "(B) acid generator" or "acid generator (B)"); and a first compound capable of forming a salt through a structural change in a molecule thereof upon irradiation with a radioactive ray (hereinafter, may be also referred to as "(C) compound" or "compound (C)"), the compound (C) not being a salt.

According to another embodiment of the invention, a resist pattern-forming method includes: applying the radiation-sensitive resin composition of the one embodiment of the invention on one face side of a substrate; exposing a resist film obtained after the applying; and developing the resist film exposed.

According to yet another embodiment of the invention, an acid diffusion control agent includes a compound capable of forming a salt through a structural change in a molecule thereof upon irradiation with a radioactive ray.

The "organic group" as referred to herein means a group having at least one carbon atom. The "acid-labile group" as referred to herein means a group that will substitute for the hydrogen atom included in the carboxy group, a hydroxy group and the like, the group being to be dissociated by an action of an acid. Furthermore, the number of "ring atoms" as referred to herein means the number of atoms constituting the ring in an alicyclic structure, an aromatic ring structure, an aliphatic hetero ring structure or an aromatic hetero ring structure, and in the case of the ring being polycyclic, the number of "ring atoms" means the total number of atoms constituting the polycycle.

According to the radiation-sensitive resin composition and the resist pattern-forming method of the embodiments of the present invention, formation of a resist pattern accompanied by less LWR, higher resolution, and fewer defects is enabled, with superior depth of focus, inhibitory ability of contraction during PEB and storage stability attained. The acid diffusion control agent of the yet another embodiment of the invention can be suitably used as an acid diffusion control agent component of the radiation-sensitive resin composition of the one embodiment of the invention. Therefore, these can be suitably used in pattern formation for manufacture of semiconductor devices in which further progress of miniaturization is expected.

Radiation-Sensitive Resin Composition

The radiation-sensitive resin composition of an embodiment of the present invention contains (A) a polymer, (B) an acid generating agent and (C) a compound. The radiation-sensitive resin composition may also contain, as favorable components, a polymer (hereinafter, may be also referred to as "(D) polymer" of "polymer (D)") having a greater percentage content by mass of fluorine atoms than the polymer (A) and/or (E) a solvent. Furthermore, the radiation-sensitive resin composition may contain other optional component within a range not leading to impairment of the effects of the present invention. Due to having the constitution described above, the radiation-sensitive resin composition is capable of leading to superior LWR performances, resolution, depth of focus, inhibitory ability of defects, inhibitory ability of contraction during PEB and storage stability (hereinafter, these performances may be also referred to as "LWR performances, etc.," as a whole). Each component will be described below.

(A) Polymer

The polymer (A) has the structural unit (I). According to the radiation-sensitive resin composition, an acid generated from the acid generator (B) and the like results in a dissociation of an acid-labile group of the polymer (A) at light-exposed regions upon irradiation with a radioactive ray, and thus a difference in solubility in a developer solution is caused between light-exposed regions and light-unexposed regions, thereby consequently enabling a resist pattern to be formed. The polymer (A) typically serves as a base polymer in the radiation-sensitive resin composition. The term "base polymer" as referred to herein means a polymer that is included in the greatest content of polymers constituting the resist pattern, and preferably, a polymer that will account for no less than 50% by mass and more preferably no less than 60% by mass.

It is preferred that the polymer (A) also has a structural unit that includes a lactone structure, a cyclic carbonate structure, a sultone structure or a combination thereof (hereinafter, may be also referred to as "structural unit (II)"), a structural unit that includes a phenolic hydroxyl group (hereinafter, may be also referred to as "structural unit (III)"), and/or a structural unit that includes an alcoholic hydroxyl group (hereinafter, may be also referred to as "structural unit (IV)") in addition to the structural unit (I). Additionally, the polymer (A) may have other structural unit than the structural units (I) to (IV). The polymer (A) may have one or two or more of these structural units. Each structural unit will be described below.

Structural Unit (I)

The structural unit (I) includes an acid-labile group. Examples of the structural unit (I) include a structural unit represented by the following formula (2) (hereinafter, may be also referred to as "structural unit (I-1)"), structural unit that includes an acetal structure (hereinafter, may be also referred to as "structural unit (I-2)"), and the like. The polymer (A) may have one or two or more of each of the structural unit (I-1) or the structural unit (I-2). The polymer (A) may have both the structural unit (I-1) and the structural unit (I-2). The structural unit (I-1) and the structural unit (I-2) will be described below.

Structural Unit (I-1)

The structural unit (I-1) is the structural unit represented by the following formula (2).

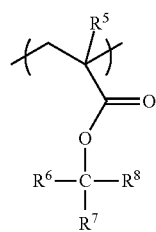

(2)

In the above formula (2), $R^5$ represents a hydrogen atom, a fluorine atom, a methyl group or a trifluoromethyl group; $R^6$ represents a monovalent hydrocarbon group having 1 to 20 carbon atoms; and $R^7$ and $R^8$ each independently represent a monovalent hydrocarbon group having 1 to 20 carbon atoms, or $R^7$ and $R^8$ taken together represent an alicyclic structure having 3 to 20 ring atoms together with the carbon atom to which $R^7$ and $R^8$ bond.

The "hydrocarbon group" may be a saturated hydrocarbon group or an unsaturated hydrocarbon group. The "hydrocarbon group" may include a chain hydrocarbon group, an alicyclic hydrocarbon group and an aromatic hydrocarbon group. The "chain hydrocarbon group" as referred to herein means a hydrocarbon group not including a ring structure but comprising only a chain structure, and both a straight chain hydrocarbon group and a branched hydrocarbon group may be involved. The "alicyclic hydrocarbon group" as referred to herein means a hydrocarbon group not including an aromatic ring structure but comprising only an alicyclic structure as the ring structure, and both a monocyclic alicyclic hydrocarbon group and a polycyclic alicyclic hydrocarbon group may be involved. However, the alicyclic hydrocarbon group does not need to be constituted with only the alicyclic structure, and a part thereof may include a chain structure. The "aromatic hydrocarbon group" as referred to herein means a hydrocarbon group including an aromatic ring structure as the ring structure. However, the aromatic hydrocarbon group does not need to be constituted with only the aromatic ring structure, and a part thereof may include a chain structure and/or an alicyclic structure.

In light of a degree of copolymerization of a monomer that gives the structural unit (I-1), $R^5$ represents preferably a hydrogen atom or a methyl group, and more preferably a methyl group.

The monovalent hydrocarbon group having 1 to 20 carbon atoms which may be represented by $R^6$, $R^7$ or $R^8$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like. Of these, the alkyl groups are preferred, alkyl groups having 1 to 4 carbon atoms are more preferred, a methyl group, an ethyl group and i-propyl group are still more preferred, and an ethyl group is particularly preferred.

Examples of the monovalent alicyclic hydrocarbon group having 3 to 20 carbon atoms include:

monocyclic alicyclic saturated hydrocarbon groups such as a cyclopentyl group and a cyclohexyl group;

monocyclic alicyclic unsaturated hydrocarbon groups such as a cyclopentenyl group and a cyclohexenyl group;

polycyclic alicyclic saturated hydrocarbon groups such as a norbornyl group, an adamantyl group and a tricyclodecyl group;

polycyclic alicyclic unsaturated hydrocarbon groups such as a norbornenyl group and a tricyclodecenyl group; and the like. Of these, the monocyclic alicyclic saturated hydrocarbon groups and the polycyclic alicyclic saturated hydrocarbon groups are preferred, and a cyclopentyl group, a cyclohexyl group, a norbornyl group and an adamantyl group are more preferred.

Examples of the monovalent aromatic hydrocarbon group having 6 to 20 carbon atoms include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthryl methyl group; and the like.

The alicyclic structure having 3 to 20 carbon atoms which may be taken together represented by $R^7$ and $R^8$ together with the carbon atom to which $R^7$ and $R^8$ bond include:

monocyclic saturated alicyclic structures such as a cyclopropane structure, a cyclobutane structure, a cyclopentane structure, a cyclohexane structure, a cycloheptane structure and a cyclooctane structure;

polycyclic saturated alicyclic structures such as a norbornane structure, an adamantane structure, a tricyclodecane structure and a tetracyclododecane structure; and the like. Of these, monocyclic saturated alicyclic structures having 5 to 8 carbon atoms and polycyclic saturated alicyclic structure having 7 to 12 carbon atoms are preferred, a cyclopentane structure, a cyclohexane structure, a cyclooctane structure, a norbornane structure and an adamantane structure are more preferred, and a cyclopentane structure and an adamantane structure are still more preferred.

Examples of the structural unit (I-1) include structural units represented by the following formulae (2-1) to (2-6) (hereinafter, may be also referred to as "structural unit (I-1-1) to (I-1-6)"), and the like.

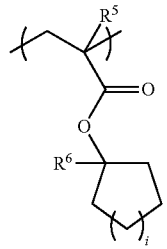

(2-1)

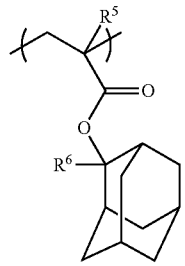

(2-2)

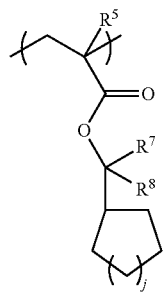

(2-3)

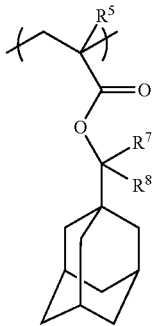

(2-4)

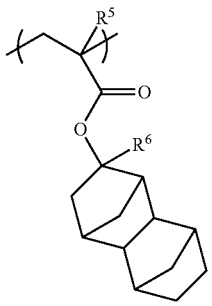

(2-5)

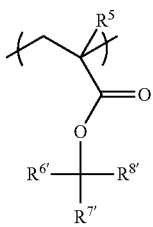

(2-6)

In the above formulae (2-1) to (2-6), $R^5$ to $R^8$ are as defined in the above formula (2).

In the above formula (2-1), i is an integer of 1 to 4.

In the above formula (2-3), j is an integer of 1 to 4.

In the above formula (2-6), $R^{6'}$, $R^7$ and $R^{7'}$ each independently represent a monovalent hydrocarbon group having 1 to 20 carbon atoms.

In the above formula, i is preferably 1 to 3, and more preferably 1 and 2.

The structural unit (I) is preferably any of the structural units (I-1-1) to (I-1-5).

Examples of the structural unit (I-1) include structural units represented by the following formulae, and the like.

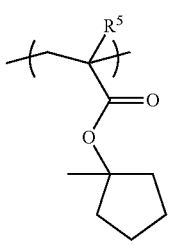 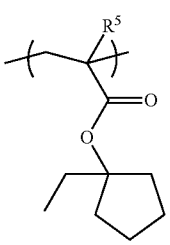 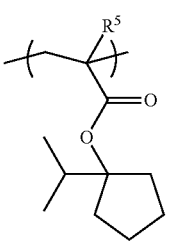

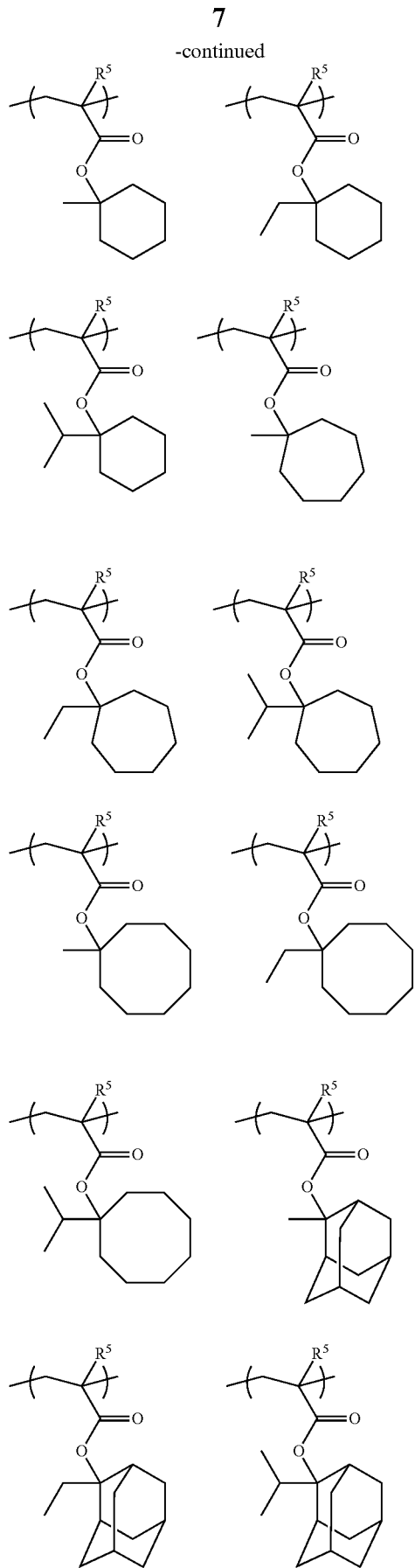
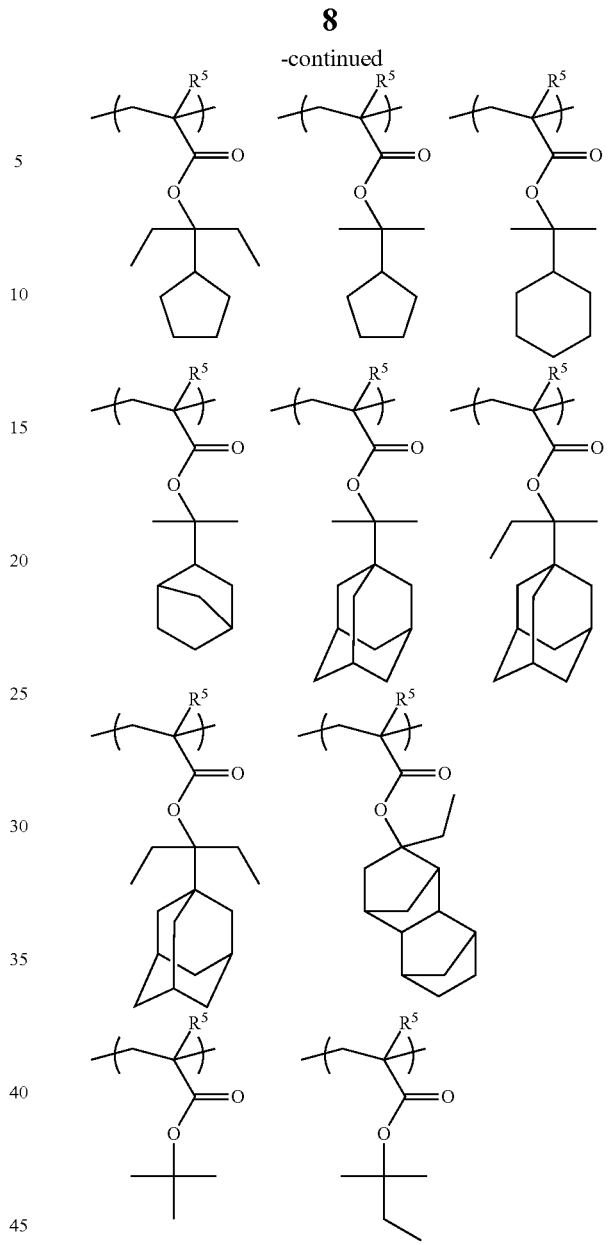

In the above formulae, $R^5$ is as defined in the above formula (2).

The structural unit (I) is preferably a structural unit derived from 1-alkyl-monocycliccycloalkan-1-yl (meth)acrylate, a structural unit derived from 2-alkyl-polycyclic cycloalkan-2-yl (meth)acrylate and a structural unit derived from 2-(cycloalkane-yl)propan-2-yl (meth)acrylate, and more preferably a structural unit derived from 1-i-propyl-cyclopentan-1-yl (meth)acrylate, a structural unit derived from 1-methylcyclohexan-1-yl (meth)acrylate, a structural unit derived from 2-ethyl-adamantan-2-yl (meth)acrylate, a structural unit derived from 2-ethyl-tetracyclododecan-2-yl (meth)acrylate, a structural unit derived from 2-(adamantan-1-yl)propan-2-yl (meth)acrylate and a structural unit derived from 2-(cyclohexan-1-yl)propan-2-yl (meth)acrylate.

Structural Unit (I-2)

The structural unit (I-2) has an acetal structure. Exemplary group having an acetal structure is a group represented by the following formula (A) (hereinafter, may be also referred to as "group (A)"), and the like. In the group (A), —C($R^9$)($R^{10}$)(O$R^z$) serves as the acid-labile group.

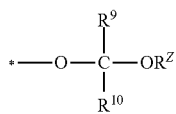
(A)

In the above formula (A), $R^9$ and $R^{10}$ each independently represent a hydrogen atom or a monovalent hydrocarbon group having 1 to 20 carbon atoms; $R^Z$ represents a monovalent hydrocarbon group having 1 to 20 carbon atoms; and * denotes a bonding site to a moiety other than the group (A) in the structural unit (I-2).

Examples of the monovalent hydrocarbon group having 1 to 20 carbon atoms which may be represented by $R^9$, $R^{10}$ or $R^Z$ include similar groups to those exemplified as the hydrocarbon group which may be represented by $R^6$, $R^7$ or $R^8$ in the above formula (2), and the like.

$R^9$ and $R^{10}$ each represent preferably a hydrogen atom or a chain hydrocarbon group, more preferably a hydrogen atom or an alkyl group, and still more preferably a hydrogen atom or a methyl group. $R^Z$ represents preferably a chain hydrocarbon group or an alicyclic hydrocarbon group, more preferably an alicyclic hydrocarbon group, still more preferably a cycloalkyl group, and particularly preferably a tetracyclododecyl group.

The structural unit (I-2) is exemplified by a structural unit represented by the following formula (2'), and the like.

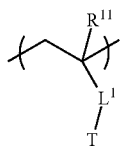
(2')

in the above formula (2'), $R^{11}$ represents a hydrogen atom, a fluorine atom, a methyl group or a trifluoromethyl group; $L^1$ represents a single bond or a divalent organic group having 1 to 20 carbon atoms; and T represents the group (A).

$R^{11}$ represents, in light of a degree of copolymerization of a monomer that gives the structural unit (I-2), more preferably a hydrogen atom or a methyl group, and still more preferably a methyl group.

The divalent organic group having 1 to 20 carbon atoms which may be represented by $L^1$ is exemplified by a substituted or unsubstituted divalent hydrocarbon group having 1 to 10 carbon atoms, —CO—, and the like. Examples of the substituent for the hydrocarbon group include a hydroxy group, a halogen atom, an alkoxy group, a cyano group, and the like.

$L^1$ represents preferably a single bond or —CO—, and more preferably —CO—.

The structural unit (I-2) is preferably a structural unit derived from 1-(tetracyclododecan-2-yloxy)ethan-1-yl (meth)acrylate.

The lower limit of the proportion of the structural unit (I) contained with respect to the total structural units constituting the polymer (A) is preferably 10 mol %, more preferably 20 mol %, still more preferably 30 mol %, and particularly preferably 40 mol %. The upper limit of the proportion is preferably 80 mol %, more preferably 70 mol %, still more preferably 60 mol %, and particularly preferably 55 mol %. When the proportion of the structural unit (I) contained falls within the above range, further improvements of the LWR performances, etc., of the radiation-sensitive resin composition are enabled.

Structural Unit (II)

The structural unit (II) includes a lactone structure, a cyclic carbonate structure, a sultone structure or a combination thereof. Due to further having the structural unit (II) in addition to the structural unit (I), the polymer (A) enables the solubility in a developer solution to be more appropriately adjusted, and as a result, more improvements of the LWR performances, etc., of the radiation-sensitive resin composition are enabled. In addition, adhesiveness of the resist pattern formed from the radiation-sensitive resin composition to the substrate can be improved.

Examples of the structural unit (II) include structural units represented by the following formulae, and the like.

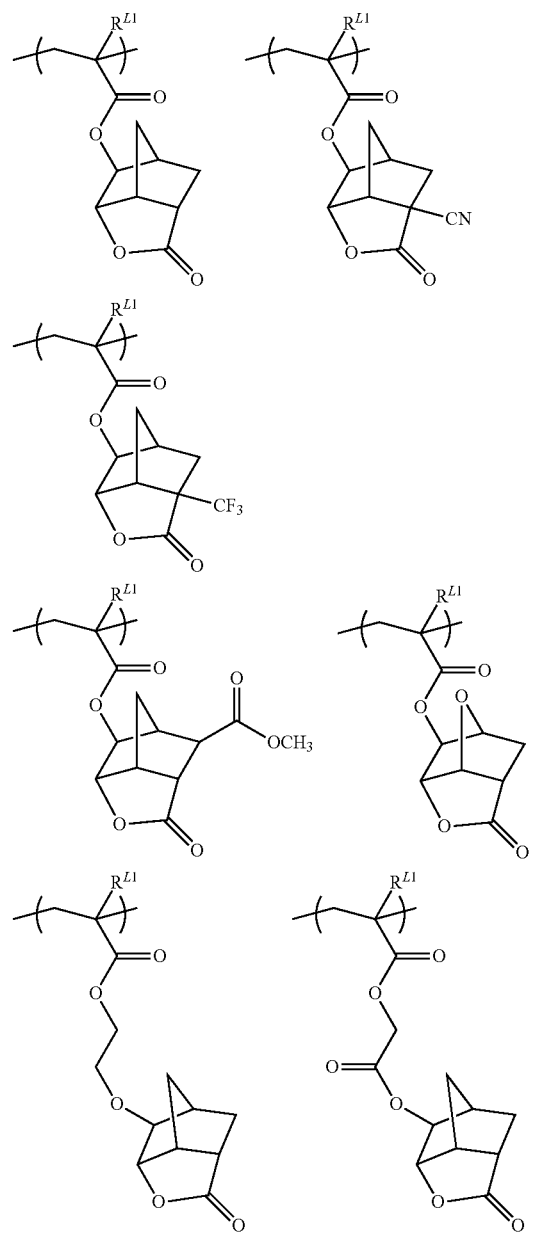

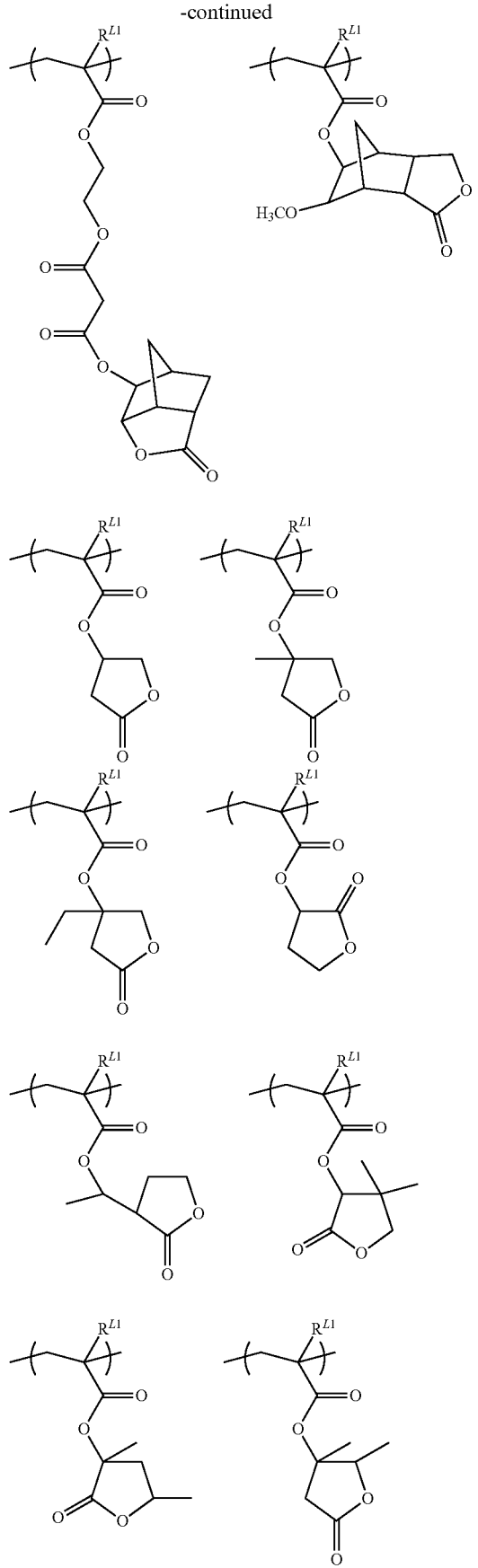
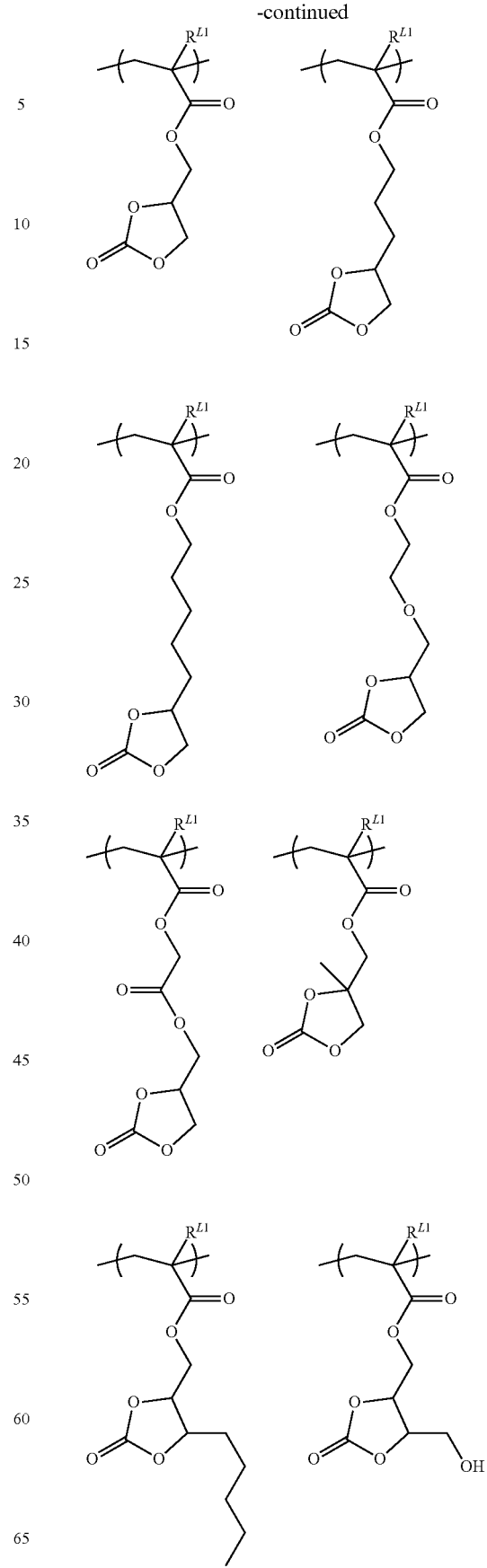

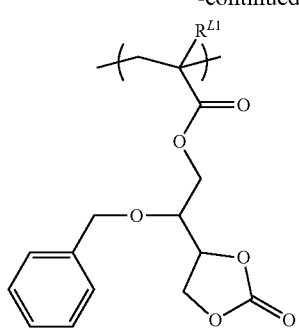
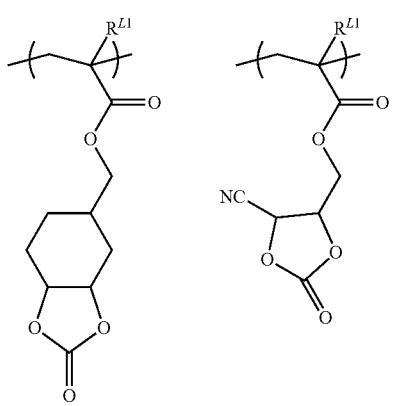
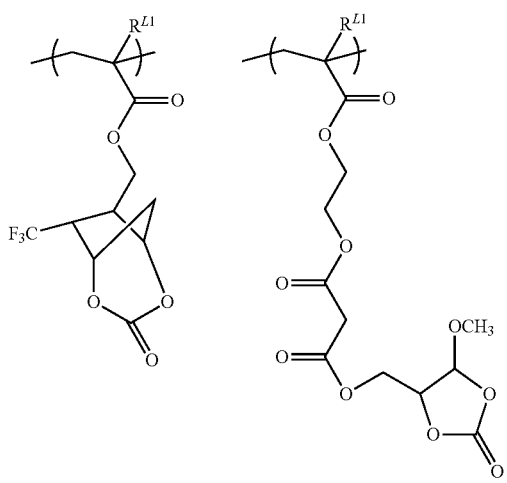
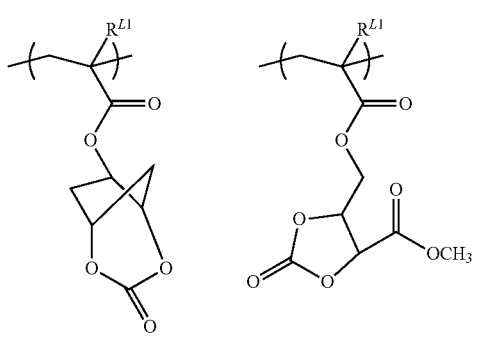
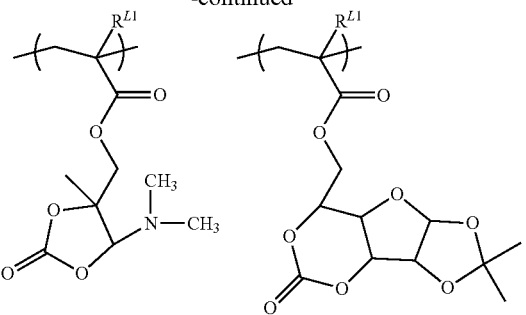
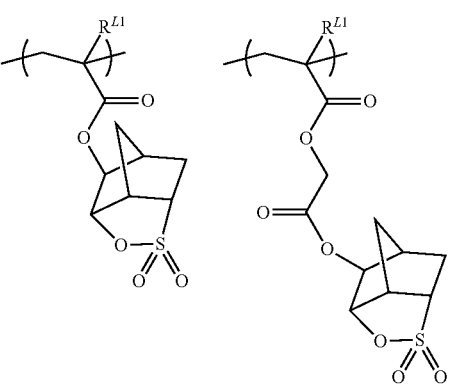
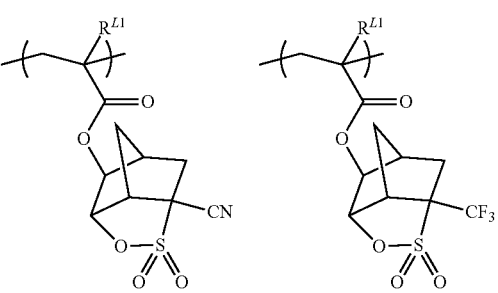
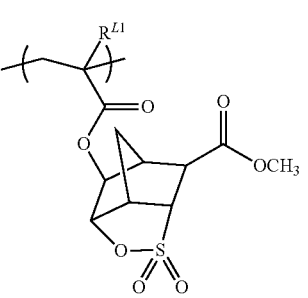
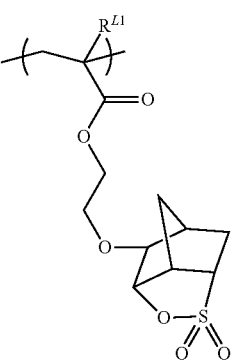

-continued

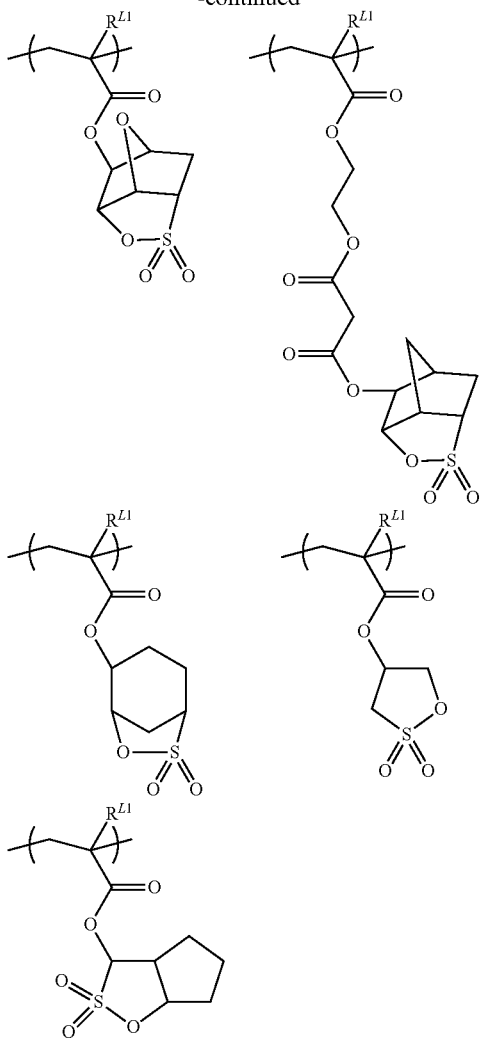

In the above formulae, $R^{L1}$ represents a hydrogen atom, a fluorine atom, a methyl group or a trifluoromethyl group.

The structural unit (II) is preferably a structural unit that includes a lactone structure, a structural unit that includes a cyclic carbonate structure and a structural unit that includes a sultone structure, more preferably a structural unit derived from lactone structure-including (meth)acrylate, a structural unit derived from cyclic carbonate structure-including (meth)acrylate and a structural unit derived from sultone structure-including (meth)acrylate, and still more preferably a structural unit derived from norbornanelactone-yl (meth)acrylate, a structural unit derived from cyanonorbornanelactone-yl (meth)acrylate, a structural unit derived from norbornanelactone-yloxycarbonyl methyl (meth)acrylate, a structural unit derived from γ-butyrolactone-yl (meth)acrylate, a structural unit derived from 1-(3-methyl-γ-norbornanelactone-3-yl)ethyl (meth)acrylate, a structural unit derived from ethylenecarbonate-ylmethyl (meth)acrylate and a structural unit derived from norbornanesultone-yl (meth)acrylate.

In the case in which the polymer (A) has the structural unit (II), the lower limit of the proportion of structural unit (II) contained with respect to the total structural units in the polymer (A) is preferably 10 mol %, more preferably 20 mol %, still more preferably 30 mol %, and particularly preferably 40 mol %. The upper limit of the proportion is preferably 80 mol %, more preferably 70 mol %, still more preferably 65 mol %, and particularly preferably 60 mol %. When the proportion of the structural unit (II) contained falls within the above range, the polymer (A) enables the solubility in a developer solution to be further appropriately adjusted, and as a result, further improvements of the LWR performances, etc., of the radiation-sensitive resin composition are enabled. In addition, the adhesiveness of the resultant resist pattern to the substrate can be further improved.

Structural Unit (III)

The structural unit (III) includes a phenolic hydroxyl group. In a case in which a KrF excimer laser beam, an extreme ultraviolet ray (EUV), an electron beam or the like is employed as the radioactive ray with which irradiation is conducted in the exposure step of the resist pattern-forming method, the polymer (A) having the structural unit (III) enables the sensitivity to be more improved.

The structural unit (III) is exemplified by a structural unit represented by the following formula (3) (hereinafter, may be also referred to as "structural unit (III-1)"), and the like.

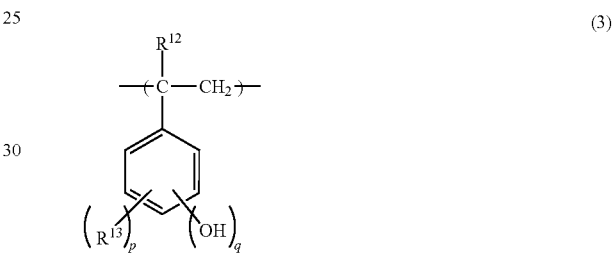

(3)

In the above formula (3), $R^{12}$ represents a hydrogen atom or a methyl group; $R^{13}$ represents a monovalent organic group having 1 to 20 carbon atoms; p is an integer of 0 to 3, wherein in a case in which p is 2 or 3, a plurality of R"s may be identical or different; and q is an integer of 1 to 3, wherein the sum, p+q, is no greater than 5.

In light of a degree of copolymerization of a monomer that gives the structural unit (III), $R^{12}$ represents preferably a hydrogen atom.

The monovalent organic group having 1 to 20 carbon atoms represented by $R^{13}$ is exemplified by: a monovalent chain hydrocarbon group having 1 to 20 carbon atoms; a monovalent alicyclic hydrocarbon group having 3 to 20 carbon atoms; a monovalent aromatic hydrocarbon group having 6 to 20 carbon atoms; a group that includes between two adjacent carbon atoms of these monovalent organic groups —CO—, —CS—, —O—, —S— or —NR"— or a group of a combination of at least two of the same; a group obtained from these groups by substituting a part or all of hydrogen atoms included therein with a substituent, and the like. R" represents a hydrogen atom or a monovalent organic group. Of these, the monovalent chain hydrocarbon group is preferred, an alkyl group is more preferred, and a methyl group is still more preferred.

In the above formula (3), p is preferably an integer of 0 to 2, more preferably 0 and 1, and still more preferably 0.

In the above formula (3), q is preferably 1 and 2, and more preferably 1.

Examples of the structural unit (III-1) include structural units represented by the following formulae (3-1) to (3-4) (hereinafter, may be also referred to as "structural units (III-1-1) to (III-1-4)"), and the like.

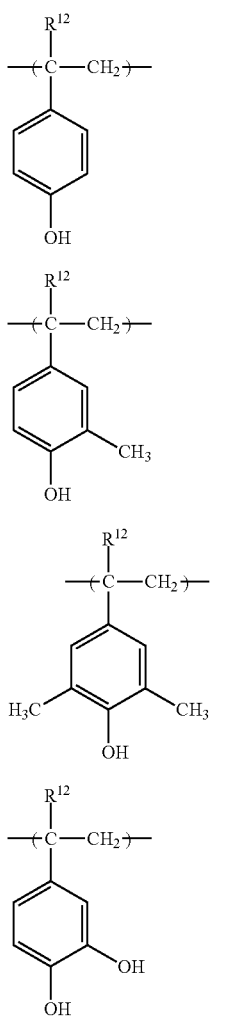

(3-1)

(3-2)

(3-3)

(3-4)

In the above formulae (3-1) to (3-4), $R^{12}$ is as defined in the above formula (3).

The structural unit (III) is preferably the structural unit (III-1), more preferably the structural unit (III-1-1) or the structural unit (III-1-2), and still more preferably the structural unit (III-1-1).

In a case in which the polymer (A) has the structural unit (III), the lower limit of the proportion of the structural unit (III) contained with respect to the total structural units constituting the polymer (A) is preferably 10 mol %, more preferably 20 mol %, still more preferably 30 mol %, and particularly preferably 40 mol %. The upper limit of the proportion is preferably 90 mol %, more preferably 80 mol %, still more preferably 70 mol %, and particularly preferably 60 mol %. When the proportion of the structural unit (III) falls within the above range, the radiation-sensitive resin composition enables the sensitivity to be further improved.

It is to be noted that the structural unit (III) may be formed by polymerizing, e.g., a monomer obtained by substituting a hydrogen atom of an —OH group in hydroxystyrene with an acetyl group or the like, and thereafter subjecting thus resulting polymer to a hydrolysis reaction in the presence of a base such as an amine.

Structural Unit (IV)

The structural unit (IV) includes an alcoholic hydroxyl group. Due to having the structural unit (IV), the polymer (A) enables the solubility in a developer solution to be more appropriately adjusted, and as a result, more improvements of the LWR performances, etc., of the radiation-sensitive resin composition are enabled. In addition, the adhesiveness of the resist pattern to the substrate can be more improved.

Examples of the structural unit (IV) include structural units represented by the following formulae, and the like.

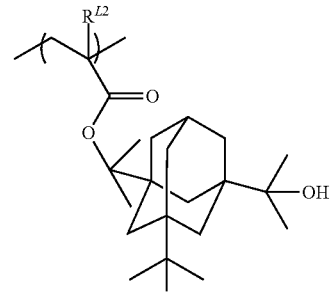

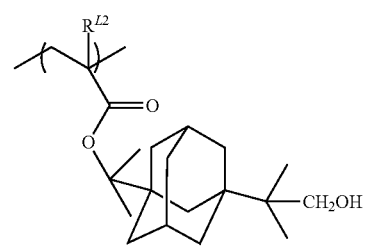

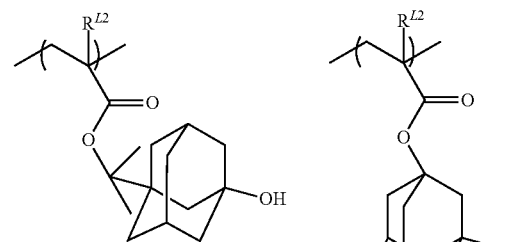

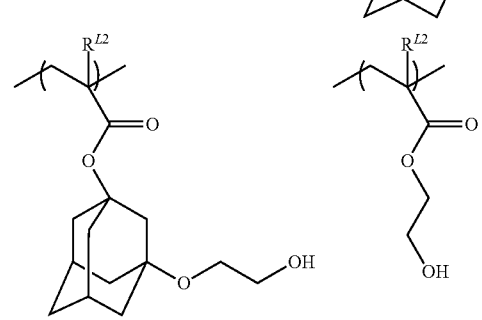

-continued

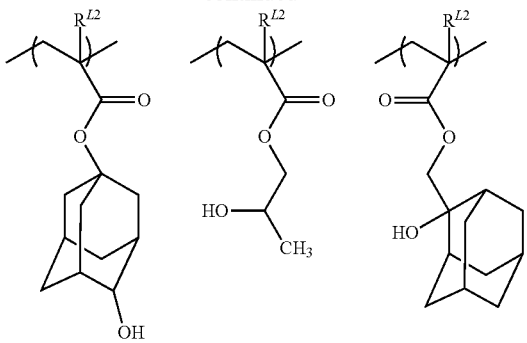
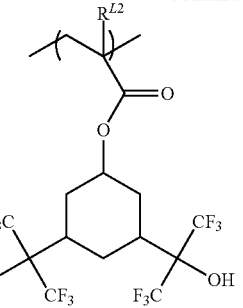
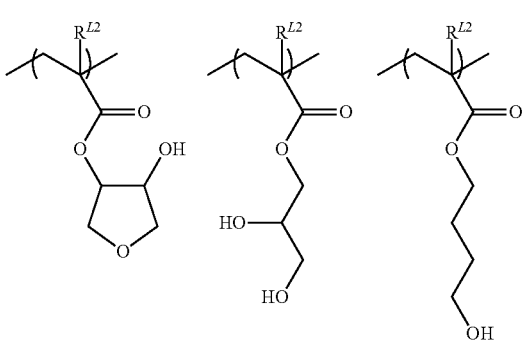
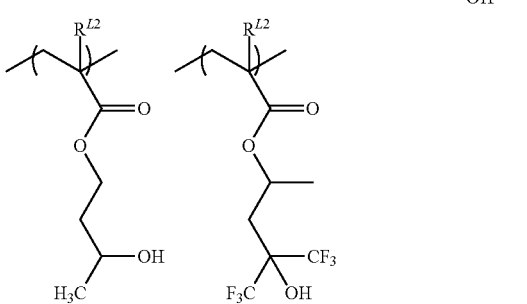
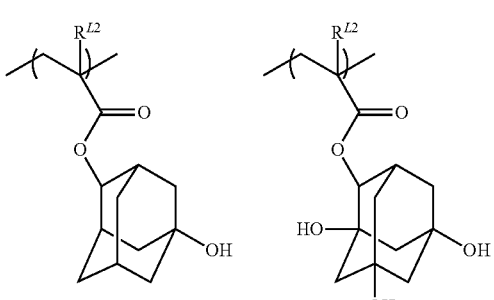
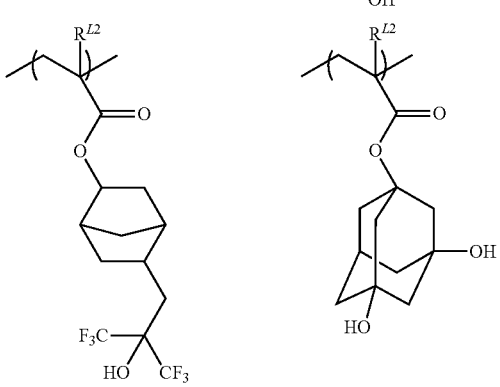

In the above formulae, $R^{L2}$ represents a hydrogen atom, a fluorine atom, a methyl group or a trifluoromethyl group.

The structural unit (IV) is preferably a structural unit that includes a hydroxyadamantyl group, and more preferably a structural unit derived from 3-hydroxyadamantyl (meth)acrylate.

In a case in which the polymer (A) has the structural unit (IV), the lower limit of the proportion of the structural unit (IV) contained with respect to the total structural units constituting the polymer (A) is preferably 5 mol %, more preferably 10 mol %, still more preferably 30 mol %, and particularly preferably 40 mol %. The upper limit of the proportion is preferably 70 mol %, more preferably 65 mol %, still more preferably 60 mol %, and particularly preferably 55 mol %. When the proportion of the structural unit (IV) falls within the above range, the polymer (A) enables the solubility in a developer solution to be further appropriately adjusted, and as a result, further improvements of the LWR performances, etc., of the radiation-sensitive resin composition are enabled. In addition, the adhesiveness of the resist pattern to the substrate can be further improved.

Other Structural Unit

The polymer (A) may have other structural unit in addition to the structural units (I) to (IV). The other structural unit is exemplified by a structural unit that includes a ketonic carbonyl group, a cyano group, a carboxy group, a nitro group, an amino group or a combination thereof, a structural unit derived from a (meth)acrylic acid ester that includes a nondissociable monovalent alicyclic hydrocarbon group, and the like. The upper limit of the proportion of the other structural unit contained with respect to the total structural units constituting the polymer (A) is preferably 20 mol %, and more preferably 10 mol %.

The lower limit of the content of the polymer (A) with respect to the total solid content of the radiation-sensitive resin composition is preferably 70% by mass, more preferably 80% by mass, and still more preferably 85% by mass. The "total solid content" as referred to herein means the sum of components other than the solvent (E) in the radiation-sensitive resin composition. The radiation-sensitive resin composition may contain one or two or more types of the polymer (A).

Synthesis Method of Polymer (A)

The polymer (A) may be synthesized by, for example, polymerization of a monomer that gives each structural unit using a radical polymerization initiator or the like in an adequate solvent.

Examples of the radical polymerization initiator include azo-based radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate;

peroxide-based radical initiators such as benzoyl peroxide, t-butyl hydroperoxide and cumene hydroperoxide; and the like. Of these, AIBN and dimethyl 2,2'-azobisisobutyrate are preferred, and AIBN is more preferred. These radical polymerization initiators may be used either alone, or as a mixture of two or more types thereof.

Examples of the solvent for use in the polymerization include:

linear or branched alkanes having 5 to 10 carbon atoms such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutane, bromohexane, dichloroethane, hexamethylene dibromide and chlorobenzene;

saturated carboxylic acid esters such as ethyl acetate, n-butyl acetate, i-butyl acetate and methyl propionate;

ketones such as acetone, methyl ethyl ketone, 4-methyl-2-pentanone and 2-heptanone;

ethers such as tetrahydrofuran, dimethoxyethane and diethoxyethane;

alcohols such as methanol, ethanol, 1-propanol, 2-propanol and 4-methyl-2-pentanol; and the like. These solvents for use in the polymerization may be used alone, or two or more types thereof may be used in combination.

The lower limit of the reaction temperature in the polymerization is preferably 40° C., and more preferably 50° C. The upper limit of the reaction temperature is preferably 150° C., and more preferably 120° C. The lower limit of the of the reaction time in the polymerization is preferably 1 hr, and more preferably 2 hrs. The upper limit of the reaction time is preferably 48 hrs, and more preferably 24 hrs.

The lower limit of the polystyrene equivalent weight average molecular weight (Mw) of the polymer (A) as determined by gel permeation chromatography (GPC) is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (A) falls within the above range, coating characteristics of the radiation-sensitive resin composition can be improved, and as a result, more improvements of LWR performances, etc., are enabled.

The lower limit of the ratio (Mw/Mn) of the Mw to the polystyrene equivalent number average molecular weight (Mn) as determined by GPC of the polymer (A) is typically 1, and preferably 1.1. The upper limit of the ratio is preferably 5, more preferably 3, still more preferably 2, and particularly preferably 1.5.

The Mw and the Mn of the polymer as referred to herein are values determined by using GPC under the following conditions.

GPC columns: for example, Tosoh Corporation, "G2000HXL"×2; "G3000HXL"×1; and "G4000HXL"×1
column temperature: 40° C.
elution solvent: tetrahydrofuran
flow rate: 1.0 mL/min
sample concentration: 1.0% by mass
amount of injected sample: 100 µL
detector: differential refractometer
standard substance: mono-dispersed polystyrene (B) Acid Generator The acid generator (B) is a substance that generates an acid upon an exposure. The acid thus generated allows the acid-labile group included in the polymer (A) or the like to be dissociated, thereby generating a carboxy group, a hydroxy group, etc. As a result, the solubility of the polymer (A) in the developer solution changes, and thus formation of a resist pattern from the radiation-sensitive resin composition is enabled. The acid generator (B) may be contained in the radiation-sensitive resin composition either in the form of a low-molecular-weight compound (hereinafter, may be also referred to as "(B) acid generating agent" or "acid generating agent (B)", as appropriate) or in the form of an acid generator incorporated as a part of the polymer, or may be in both of these forms.

The acid generating agent (B) is exemplified by an onium salt compound, an N-sulfonyloxyimide compound, a sulfonimide compound, a halogen-containing compound, a diazo ketone compound, and the like.

Exemplary onium salt compound includes a sulfonium salt, a tetrahydrothiophenium salt, an iodonium salt, a phosphonium salt, a diazonium salt, a pyridinium salt, and the like.

Specific examples of the acid generating agent (B) include compounds disclosed in paragraphs [0080] to [0113] of Japanese Unexamined Patent Application, Publication No. 2009-134088, and the like.

Example of the acid generated from the acid generator (B) include a sulfonic acid, an imide acid, an amide acid, a methide acid, a phosphinic acid, a carboxylic acid, and the like. Of these, the sulfonic acid, the imide acid, the amide acid and the methide acid are preferred.

The acid generating agent (B) is exemplified by a compound represented by the following formula (4) (hereinafter, may be also referred to as "(B1) acid generating agent" or "acid generating agent (B1)"), and the like.

$$A^-Z^+ \quad (4)$$

In the above formula (4), $A^-$ represents a monovalent sulfonic acid anion, a monovalent imide acid anion, a monovalent amide acid anion or a monovalent methide acid anion; and $Z^+$ represents a monovalent radiation-sensitive onium cation.

In a case in which $A^-$ in the above formula (4) represents the sulfonic acid anion, the sulfonic acid is generated from the acid generating agent (B1) (hereinafter, may be also referred to as "(B1a) acid generating agent"). In a case in which $A^-$ represents the imide acid anion, the imide acid is generated from the acid generating agent (B1) (hereinafter, may be also referred to as "(B1b) acid generating agent"). In a case in which $A^-$ represents the amide acid anion, the amide acid is generated from the acid generating agent (B1) (hereinafter, may be also referred to as "(B1c) acid generating agent"). In a case in which $A^-$ represents the methide acid anion, the methide acid is generated from the acid generating agent (B1) (hereinafter, may be also referred to as "(B1d) acid generating agent").

The acid generating agent (B1a) is exemplified by a compound represented by the following formula (4-1) (hereinafter, may be also referred to as "compound (4-1)"), and the like. When the acid generating agent (B1) has the following structure, it is expected that a diffusion length of the acid generated upon the exposure in the resist film will be more properly reduced through e.g., an interaction with the structural unit (I) of the polymer (A) or the like, and as a result, more improvements of the LWR performances, etc., of the radiation-sensitive resin composition are enabled.

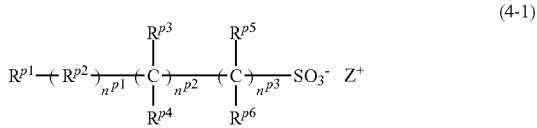

(4-1)

In the above formula (4-1), $R^{p1}$ represents a monovalent group that includes a ring structure having 5 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 0 to 10, wherein the sum of $n^{p1}$, $n^{p2}$ and $n^{p3}$ is no less than 1 and no greater than 30, and wherein in a case in which $n^{p1}$ is no less than 2, a plurality of $R^{p2}$s may be identical or different, in a case in which $n^{p2}$ is no less than 2, a plurality of $R^{p3}$s may be identical or different and a plurality of $R^{p4}$s may be identical or different, and in a case in which $n^{p3}$ is no less than 2, a plurality of $R^{p5}$s may be identical or different and a plurality of $R^{p6}$s may be identical or different; and $Z^+$ is as defined in the above formula (4).

The monovalent group that includes a ring structure having 5 or more ring atoms which is represented by $R^{p1}$ is exemplified by: a monovalent group that includes an alicyclic structure having 5 or more ring atoms; a monovalent group that includes an aliphatic heterocyclic structure having 5 or more ring atoms; a monovalent group that includes an aromatic ring structure having 5 or more ring atoms; a monovalent group that includes an aromatic heterocyclic structure having 5 or more ring atoms; and the like.

Examples of the alicyclic structure having 5 or more ring atoms include:

monocyclic saturated alicyclic structures such as a cyclopentane structure, a cyclohexane structure, a cycloheptane structure, a cyclooctane structure, a cyclononane structure, a cyclodecane structure and a cyclododecane structure;

monocyclic unsaturated alicyclic structures such as a cyclopentene structure, a cyclohexene structure, a cycloheptene structure, a cyclooctene structure and a cyclodecene structure;

polycyclic saturated alicyclic structures such as a norbornane structure, an adamantane structure, a tricyclodecane structure and a tetracyclododecane structure;

polycyclic unsaturated alicyclic structures such as a norbornene structure and a tricyclodecene structure; and the like.

Examples of the aliphatic heterocyclic structure having 5 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic ring structure having 5 or more ring atoms include a benzene structure, a naphthalene structure, a phenanthrene structure, an anthracene structure, and the like.

Examples of the aromatic heterocyclic structure having 5 or more ring atoms include:

oxygen atom-containing heterocyclic structures such as a furan structure, a pyran structure and a benzopyran structure;

nitrogen atom-containing heterocyclic structures such as a pyridine structure, a pyrimidine structure and an indole structure; and the like.

The lower limit of the number of ring atoms of the ring structure included in $R^{p1}$ is preferably 6, more preferably 8, still more preferably 9, and particularly preferably 10. The upper limit of the number of ring atoms is preferably 15, more preferably 14, still more preferably 13, and particularly preferably 12. When the number of ring atoms falls within the above range, the aforementioned diffusion length of the acid may be further properly reduced, and as a result, more improvements of the LWR performances, etc., of the radiation-sensitive resin composition are enabled.

A part or all of hydrogen atoms included in the ring structure of $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, the hydroxy group is preferred.

$R^{p1}$ represents preferably a monovalent group that includes an alicyclic structure having 5 or more ring atoms or a monovalent group that includes an aliphatic heterocyclic structure having 5 or more ring atoms, more preferably a monovalent group that includes an alicyclic structure having 9 or more ring atoms or a monovalent group that includes an aliphatic heterocyclic structure having 9 or more ring atoms, still more preferably an adamantyl group, a hydroxyadamantyl group, a norbornanelactone-yl group, a norbornanesultone-yl group and a 5-oxo-4-oxatricyclo[4.3.1.1$^{3,8}$]undecan-yl group, and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. Of these, the carbonyloxy group, the sulfonyl group, an alkanediyl group and a cycloalkanediyl group are preferred, the carbonyloxy group and the cycloalkanediyl group are more preferred, the carbonyloxy group and a norbornanediyl group are still more preferred, and the carbonyloxy group is particularly preferred.

The monovalent hydrocarbon group having 1 to 20 carbon atoms which may be represented by $R^{p3}$ or $R^{p4}$ is exemplified by an alkyl group having 1 to 20 carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent preferably a hydrogen atom, a fluorine atom or a fluorinated alkyl group, more preferably a fluorine atom or a perfluoroalkyl group, and still more preferably a fluorine atom or a trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

In the above formula (4-1), $n^{p1}$ is preferably an integer of 0 to 5, more preferably an integer of 0 to 3, still more preferably an integer of 0 to 2, and particularly preferably 0 or 1.

In the above formula (4-1), $n^{p2}$ is preferably an integer of 0 to 5, more preferably an integer of 0 to 2, still more preferably 0 or 1, and particularly preferably 0.

The lower limit of $n^{p3}$ is preferably 1, and more preferably 2. When $n^{p3}$ is no less than 1, the strength of the acid generated from the compound (4-1) may be increased, and consequently the LWR performances, etc. of the radiation-sensitive resin composition may be more improved. The upper limit of $n^{p3}$ is preferably 4, more preferably 3, and still more preferably 2.

The lower limit of the sum of $n^{p1}$, $n^{p2}$ and $n^{p3}$ is preferably 2, and more preferably 4. The upper limit of the sum of $n^{p1}$, $n^{p2}$ and $n^{p3}$ is preferably 20, and more preferably 10.

Examples of the monovalent radiation-sensitive onium cation represented by $Z^+$ include cations represented by the following formulae (Z-1) to (Z-3) (hereinafter, may be also referred to as "cations (Z-1) to (Z-3)"), and the like.

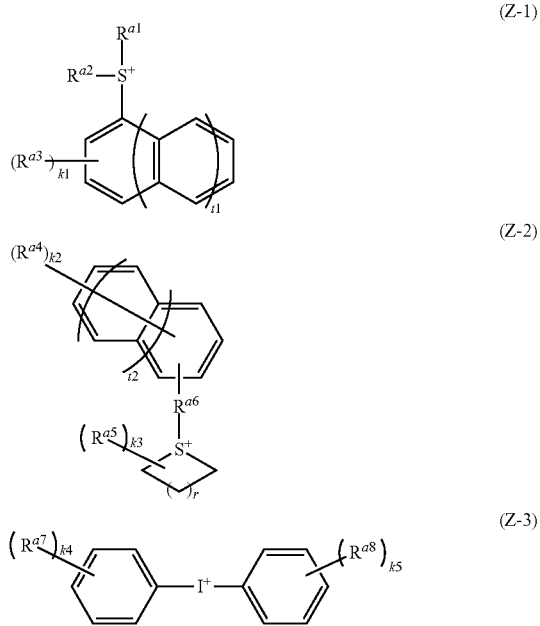

In the above formula (Z-1), $R^{a1}$ and $R^{a2}$ each independently represent a monovalent organic group having 1 to 20 carbon atoms; $R^{3a}$ represents a monovalent organic group having 1 to 20 carbon atoms, a hydroxy group, a nitro group or a halogen atom; k1 is each independently an integer of 0 to 5, wherein in a case in which $R^{a1}$ is present in a plurality of number, a plurality of $R^{a3}$s may be identical or different, and the plurality of $R^{a3}$s may taken together represent a ring structure; and t1 is an integer of 0 to 3.

The monovalent organic group having 1 to 20 carbon atoms which may be represented by $R^{a1}$, $R^{a2}$ or $R^{a3}$ is exemplified by a monovalent hydrocarbon group having 1 to 20 carbon atoms, a monovalent group (g) that includes a divalent hetero atom-containing group between two adjacent carbon atoms, or at the end of the atomic bonding side of the monovalent hydrocarbon group; a monovalent group obtained from the monovalent hydrocarbon group and the group (g) by substituting with a monovalent hetero atom-containing group a part or all of hydrogen atoms included therein; and the like.

$R^{a1}$ and $R^{a2}$ each represent preferably a monovalent unsubstituted hydrocarbon group or a hydrocarbon group having 1 to 20 carbon atoms obtained therefrom by substituting a hydrogen atom included therein with a substituent, more preferably a monovalent unsubstituted aromatic hydrocarbon group having 6 to 18 carbon atoms or an aromatic hydrocarbon group obtained therefrom by substituting a hydrogen atom included therein with a substituent, and still more preferably a phenyl group.

The substituent which may substitute for the hydrogen atom included in the monovalent hydrocarbon group having 1 to 20 carbon atoms which may be represented by $R^{a1}$ or $R^{a2}$ is preferably a substituted or unsubstituted monovalent hydrocarbon group having 1 to 20 carbon atoms, $-OSO_2-R^k$, $-SO_2-R^k$, $-OR^k$, $-COOR^k$, $-O-CO-R^k$, $-O-R^{kk}-COOR^k$, $-R^{kk}-CO-R^k$ and $-S-R^k$, wherein $R^k$ represents a monovalent hydrocarbon group having 1 to 10 carbon atoms; and $R^{kk}$ represents a single bond or a divalent hydrocarbon group having 1 to 10 carbon atoms.

$R^{a3}$ represents preferably a substituted or unsubstituted monovalent hydrocarbon group having 1 to 20 carbon atoms, $-OSO_2-R^k$, $-SO_2-R^k$, $-OR^k$, $-COOR^k$, $-O-CO-R^k$, $-O-R^{kk}-COOR^k$, $-R^{kk}-CO-R^k$ or $-S-R^k$, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (Z-2), $R^{a4}$ and $R^{a5}$ each independently represent a monovalent organic group having 1 to 20 carbon atoms, a hydroxy group, a nitro group or a halogen atom; k2 is an integer of 0 to 7, wherein in a case in which $R^{a4}$ is present in a plurality of number, a plurality of $R^{a4}$s may be identical or different, and the plurality of $R^{a4}$s may taken together represent a ring structure; k3 is an integer of 0 to 6, wherein in a case in which $R^{a5}$ is present in a plurality of number, a plurality of $R^{a5}$s may be identical or different, and the plurality of $R^{a5}$s may taken together represent a ring structure; r is an integer of 0 to 3; $R^{a6}$ represents a single bond or a divalent organic group having 1 to 20 carbon atoms; and t2 is an integer of 0 to 2.

$R^{a4}$ and $R^{a5}$ each represent preferably a substituted or unsubstituted monovalent hydrocarbon group having 1 to 20 carbon atoms, $-OR^k$, $-COOR^k$, $-O-CO-R^k$, $-O-R^{kk}-COOR^k$ or $-R^{kk}-CO-R^k$, wherein $R^k$ represents a monovalent hydrocarbon group having 1 to 10 carbon atoms; and $R^{kk}$ represents a single bond or a divalent hydrocarbon group having 1 to 10 carbon atoms.

In the above formula (Z-3), $R^{a7}$ and $R^{a8}$ each independently represent a monovalent organic group having 1 to 20 carbon atoms, a hydroxy group, a nitro group or a halogen atom; and k4 and k5 are each independently an integer of 0 to 5, wherein in a case in which $R^{a7}$ is present in a plurality of number, a plurality of $R^{a7}$s may be identical or different, and the plurality of $R^{a7}$s may taken together represent a ring structure, in a case in which $R^{a8}$ is present in a plurality of number, a plurality of $R^{a8}$s may be identical or different, and the plurality of $R^{a8}$s may taken together represent a ring structure.

$R^{a7}$ and $R^{a8}$ each represent preferably a substituted or unsubstituted monovalent hydrocarbon group having 1 to 20 carbon atoms, $-OSO_2-R^k$, $-SO_2-R^k$, $-OR^k$, $-CO-$ OR$^k$, —O—CO—R$^k$, —O—R$^{kk}$—COOR$^k$, —R$^{kk}$—CO—R$^k$, —S—R$^k$, or a ring structure taken together represented by at least two of R$^{a7}$ and R$^{a8}$, wherein R$^k$ represents a monovalent hydrocarbon group having 1 to 10 carbon atoms; and R$^{kk}$ represents a single bond or a divalent hydrocarbon group having 1 to 10 carbon atoms.

Examples of the monovalent hydrocarbon group having 1 to 20 carbon atoms which may be represented by R$^{a3}$, R$^{a4}$, R$^{a5}$, R$^{a7}$ r R$^{a8}$ include linear alkyl groups such as a methyl group, an ethyl group, a n-propyl group and a n-butyl group;

branched alkyl groups such as an i-propyl group, an i-butyl group, a sec-butyl group and a t-butyl group;

aryl groups such as a phenyl group, a tolyl group, a xylyl group, a mesityl group and a naphthyl group;

aralkyl groups such as a benzyl group and a phenethyl group; and the like.

Examples of the divalent organic group represented by R$^{a6}$ include groups obtained by removing one hydrogen atom from the monovalent organic group having 1 to 20 carbon atoms exemplified as R$^{a1}$, R$^{a2}$ and R$^{a3}$ in the above formula (Z-1), and the like.

Examples of the substituent which may substitute for the hydrogen atom included in the hydrocarbon group which may be represented by R$^{a3}$, R$^{a4}$, R$^{a5}$, R$^{a7}$ or R$^{a8}$ include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, the halogen atom is preferred, and a fluorine atom is more preferred.

R$^{a3}$, R$^{a4}$, R$^{a5}$, R$^{a7}$ and R$^{a8}$ each represent preferably an unsubstituted linear or branched monovalent alkyl group, a monovalent fluorinated alkyl group, an unsubstituted monovalent aromatic hydrocarbon group, —OSO$_2$—R$^k$, —SO$_2$—R$^k$ or —OR$^k$, more preferably a fluorinated alkyl group, an unsubstituted monovalent aromatic hydrocarbon group or an alkoxy group, and still more preferably a fluorinated alkyl group or an alkoxy group.

In the formula (Z-1), k1 is preferably an integer of 0 to 2, more preferably 0 and 1, and still more preferably 0; and t1 is preferably 0 and 1, and more preferably 0. In the formula (Z-2), k2 is preferably an integer of 0 to 2, more preferably 0 and 1, and still more preferably 1; k3 is preferably an integer of 0 to 2, more preferably 0 and 1, and still more preferably 0; r is preferably 2 and 3, and more preferably 2; and t2 is preferably 0 and 1, and more preferably 1. In the formula (Z-3), k4 and k5 are each preferably an integer of 0 to 2, more preferably 0 and 1, and still more preferably 0.

Of these, Z$^+$ represents preferably the cation (Z-1) or the cation (Z-2), and more preferably a triphenylsulfonium cation or a 4-butoxynaphthalen-1-yltetrahydrothiophenium cation.

Examples of the acid generating agent (B1a) include compounds represented by the following formulae (4-1-1) to (4-1-19) (hereinafter, may be also referred to as "compounds (4-1-1) to (4-1-19)"), and the like. Examples of the acid generating agent (B1b) include compounds represented by the following formulae (4-2-1) to (4-2-3) (hereinafter, may be also referred to as "compounds (4-2-1) to (4-2-3)"), and the like. Examples of the acid generating agent (B1c) include compounds represented by the following formulae (4-3-1) to (4-3-2) (hereinafter, may be also referred to as "compounds (4-3-1) to (4-3-2)"), and the like. Examples of the acid generating agent (B1d) include compounds represented by the following formulae (4-4-1) to (4-4-2) (hereinafter, may be also referred to as "compounds (4-4-1) to (4-4-2)"), and the like.

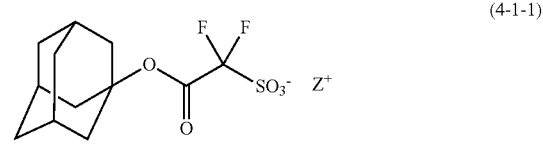
(4-1-1)

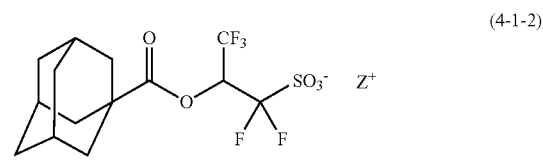
(4-1-2)

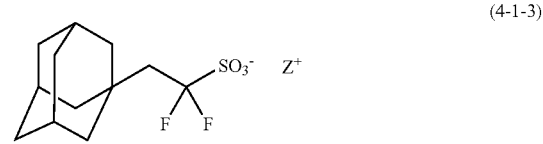
(4-1-3)

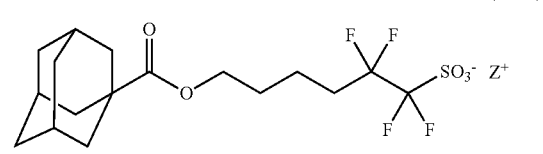
(4-1-4)

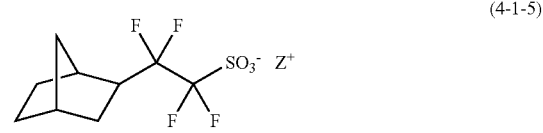
(4-1-5)

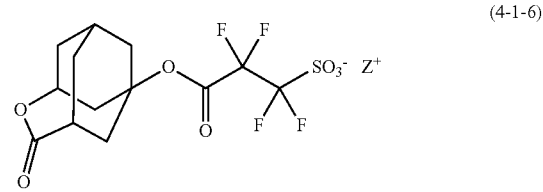
(4-1-6)

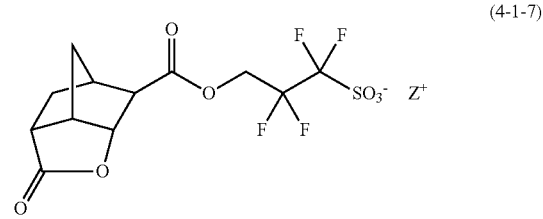
(4-1-7)

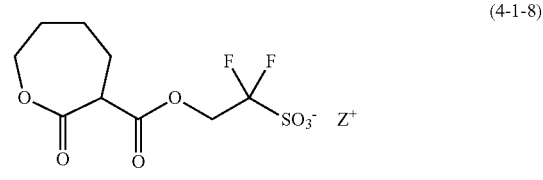
(4-1-8)

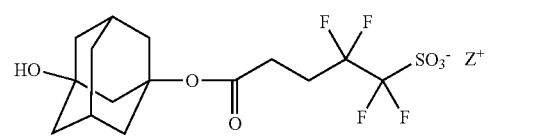
(4-1-9)

(4-1-10) 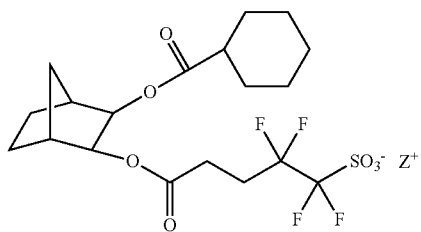
(4-1-11) 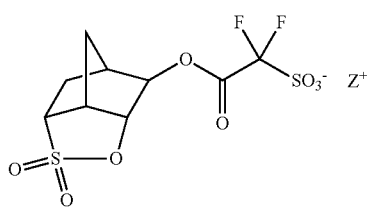
(4-1-12) 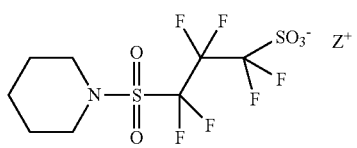
(4-1-13) 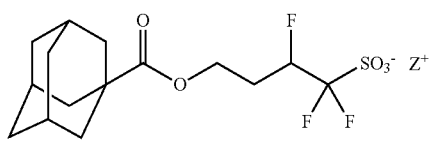
(4-1-14) 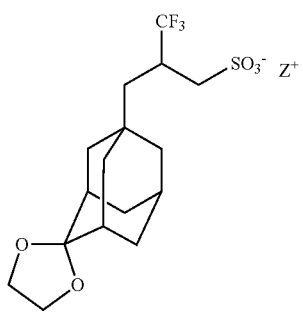
(4-1-15) 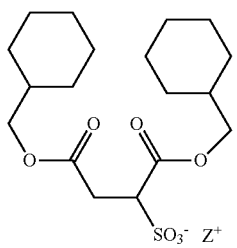
(4-1-16) 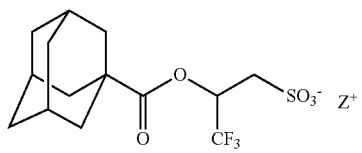
(4-1-17) 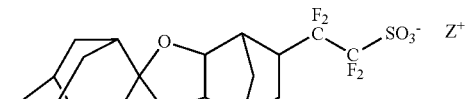
(4-1-18) 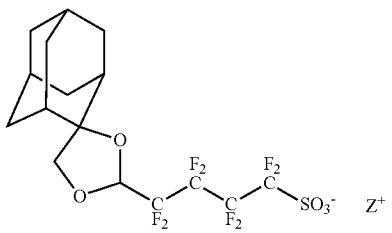
(4-1-19) 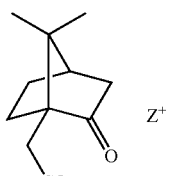
(4-2-1) 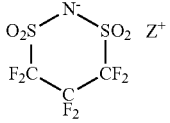
(4-2-2) 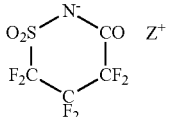
(4-2-3) 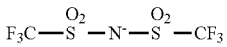
(4-3-1) 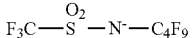
(4-3-2) 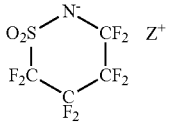
(4-4-1) 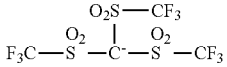
(4-4-2) 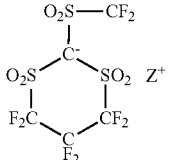
In the above formulae (4-1-1) to (4-1-19), (4-2-1) to (4-2-3), (4-3-1), (4-3-2), (4-4-1) and (4-4-2), $Z^+$ represents a monovalent onium cation.
The acid generating agent (B1) is preferably the acid generating agent (B1a) or the acid generating agent (B1b), more preferably any of the compounds (4-1-1), (4-1-3), (4-1-13) and (4-1-16) to (4-1-19), and still more preferably the compound (4-2-1).

The acid generating agent (B1) is preferably the onium salt compound, more preferably a sulfonium salt or a tetrahydrothiophenium salt, and still more preferably a triphenylsulfonium salt or a 4-butoxynaphthalen-1-yltetrahydrothiophenium salt.

In addition, a polymer having the structure of the acid generator incorporated thereinto as a part of the polymer, e.g., a polymer that has a structural unit represented by the following formula (4-1'), is also preferred as the acid generator (B).

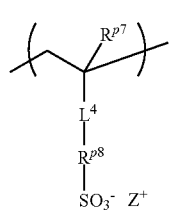

(4-1')

In the above formula (4-1'), $R^{p7}$ represents a hydrogen atom or a methyl group; $L^4$ represents a single bond, —COO— or a divalent carbonyloxyhydrocarbon group; $R^{p8}$ represents a fluorinated alkanediyl group having 1 to 10 carbon atoms; and $Z^+$ is as defined in the above formula (4).

In light of the copolymerizability of a monomer that gives the structural unit represented by the above formula (4-1'), $R^{p7}$ represents preferably a hydrogen atom or a methyl group, and more preferably a methyl group.

$L^4$ represents preferably a divalent carbonyloxyhydrocarbon group, and more preferably a carbonyloxyalkanediyl group or a carbonyl alkanediylarenediyl group.

$R^{p8}$ represents preferably a fluorinated alkanediyl group having 1 to 4 carbon atoms, more preferably a perfluoroalkanediyl group having 1 to 4 carbon atoms, and still more preferably a hexafluoropropanediyl group.

In a case in which the acid generator (B) is the acid generating agent (B), the lower limit of the content of the acid generating agent (B) with respect to 100 parts by mass of the polymer (A) is preferably 0.1 parts by mass, more preferably 0.5 parts by mass, still more preferably 1 part by mass, particularly preferably 2 parts by mass, further particularly preferably 3 parts by mass, and most preferably 5 parts by mass. The upper limit of the aforementioned content is preferably 50 parts by mass, more preferably 40 parts by mass, still more preferably 30 parts by mass, and particularly preferably 20 parts by mass.

Moreover, the lower limit of the content of the acid generating agent (B) in terms of solid content equivalent, i.e., with respect to the total solid content of the radiation-sensitive resin composition, is preferably 0.1% by mass, more preferably 0.5% by mass, still more preferably 1% by mass, particularly preferably 5% by mass, further particularly preferably 10% by mass, and most preferably 15% by mass. The upper limit of the aforementioned content is preferably 50% by mass, more preferably 40% by mass, still more preferably 30% by mass, and particularly preferably 20% by mass.

When the content of the acid generating agent (B) falls within the above range, the sensitivity and the developability of the radiation-sensitive resin composition may be improved, and consequently LWR performances, etc. may be improved. In particular, in a case in which the exposure light is an electron beam or EUV, in light of a more improvement of the sensitivity of the radiation-sensitive resin composition, the lower limit of the content of the acid generating agent (B) with respect to 100 parts by mass of the polymer (A) is preferably 10 parts by mass, more preferably 15 parts by mass, and still more preferably 18 parts by mass. Also, the lower limit of the content of the acid generating agent (B) with respect to the total solid content of the radiation-sensitive resin composition is preferably 10% by mass, more preferably 15 parts by mass, and still more preferably 18 parts by mass. The radiation-sensitive resin composition may contain one or two or more types of the acid generator (B).

(C) Compound

The compound (C) is capable of forming a salt through a structural change in a molecule thereof upon irradiation with a radioactive ray. More specifically, the compound (C) changes its molecular structure by an action of a radioactive ray to be a salt. Examples of the radioactive ray include electromagnetic waves e.g., visible light rays, ultraviolet rays, far ultraviolet rays such as an ArF excimer laser beam (wavelength: 193 nm) and a KrF excimer laser beam (wavelength: 248 nm), extreme ultraviolet rays (EUV; 13.5 nm), X-rays, etc., and charged particle rays such as an electron beam and an α-ray, and the like. The radioactive ray is preferably exposure light employed in resist pattern formation.

The compound (C) is a compound not being a salt. Moreover, the compound (C) is typically a basic compound.

Due to containing the compound (C) in addition to the polymer (A) and the acid generator (B), the radiation-sensitive resin composition leads to superior LWR performance, resolutions, depth of focus, inhibitory ability of defects, inhibitory ability of contraction during PEB and storage stability. Although not necessarily clarified and without wishing to be bound by any theory, the reason for achieving the effects described above due to the radiation-sensitive resin composition having the aforementioned constitution is inferred as in the following, for example. The compound (C) captures in light-unexposed regions the acid having been generated from the acid generator (B) in light-exposed regions, whereas the acid-capturing function decreases in light-exposed regions due to the change into the salt by an action of the radioactive ray. As a result, an enhancement of the contrast between the light-exposed regions and the light-unexposed regions is enabled, whereby the LWR performance, the developability and the depth of focus can be more improved. Unlike radiation-sensitive acid diffusion control agents such as photodegradable bases, the compound (C) exhibits a superior inhibitory ability of defects since the solubility in a developer solution changes similarly to the polymer (A). In addition, the compound (C) is less volatile due to the change into the salt in light-exposed regions, thereby leading to a superior inhibitory ability of contraction during PEB. Furthermore, since the basicity of the compound (C) is low as compared with that of the conventional acid diffusion control agent, the radiation-sensitive resin composition containing this compound is believed to be superior in storage stability.

Typically, basicity of the compound (C) changes upon irradiation with a radioactive ray. Furthermore, the compound (C) typically generates an acid upon irradiation with a radioactive ray, and the acid forms a salt through bonding to a basic site of the compound (C), thereby leading to a decrease in the basicity.

The compound (C) is exemplified by a compound represented by the following formula (1) (hereinafter, may be also referred to as "compound (I-1)"), and the like.

(1)

In the above formula (1), $Ar^1$ represents a substituted or unsubstituted heteroarenediyl group having 4 to 30 ring atoms and having at least one nitrogen atom as a ring-constituting atom; $Ar^2$ represents a substituted or unsubstituted aryl group having 6 to 30 ring atoms in which at least one hydrogen atom bonds to a carbon atom of an aromatic ring or a substituted or unsubstituted heteroaryl group having 4 to 30 ring atoms in which at least one hydrogen atom bonds to a carbon atom of an aromatic ring; $Ar^3$ represents an aryl group having 6 to 30 ring atoms in which at least one leaving group bonds to a carbon atom of an aromatic ring and having or not having a substituent other than the leaving group or a heteroaryl group having 4 to 30 ring atoms in which at least one leaving group bonds to a carbon atom of an aromatic ring and having or not having a substituent other than the leaving group, wherein number of covalent bonds constituting a shortest bond path between the carbon atom to which the hydrogen atom bonds in $Ar^2$ and the carbon atom to which the leaving group bonds in $Ar^3$ is no less than 4 and no greater than 7.

The compound (I-1) absorbs the radioactive ray by, for example, the heteroarenediyl group represented by $Ar^1$, and the hydrogen atom of the aryl group or the heteroaryl group represented by $Ar^2$ joins the leaving group bonded to the aromatic ring represented of $Ar^3$, thereby generating the acid which then leaves. Formation of the salt is then enabled through bonding between $Ar^2$ and $Ar^3$, along with bonding of the acid thus generated to the nitrogen atom of $Ar^1$.

Examples of the heteroarenediyl group having 4 to 30 ring atoms and having at least one nitrogen atom as a ring-constituting atom represented by $Ar^1$ include:

groups having one nitrogen atom as the ring-constituting atom, such as a pyrrolediyl group and a pyridinediyl group;

groups having two nitrogen atoms as the ring-constituting atom, such as an imidazolediyl group, a pyrazolediyl group, a pyrazinediyl group, a pyrimidinediyl group and a pyridazinediyl group; and the like. Of these, in light of improvements of the LWR performances, etc., the groups having two nitrogen atoms as the ring-constituting atom are preferred, and the imidazolediyl group is more preferred.

The substituent of the heteroarenediyl group is exemplified by a monovalent organic group, and the like. Alternatively, the substituent of the heteroarenediyl group may be a group that forms a ring structure, such as an aromatic ring or an alicyclic ring, that is to be fused with the heteroarene ring.

Examples of the aryl group having 6 to 30 ring atoms which may be represented by $Ar^2$ in which at least one hydrogen atom bonds to the carbon atom of the aromatic ring include a phenyl group, a naphthyl group, an anthryl group, and the like. Of these, a phenyl group is preferred.

Examples of the heteroaryl group having 4 to 30 ring atoms which may be represented by $Ar^2$ in which at least one hydrogen atom bonds to the carbon atom of the aromatic ring include a pyrrolyl group, a pyridyl group, a furyl group, a thiophenyl group, and the like. Of these, a pyridyl group is preferred.

Examples of the substituent of the aryl group having 6 to 30 ring atoms which may be represented by $Ar^2$ in which at least one hydrogen atom bonds to the carbon atom of the aromatic ring, and the heteroaryl group having 4 to 30 ring atoms which may be represented by $Ar^2$ in which at least one hydrogen atom bonds to the carbon atom of the aromatic ring include a monovalent organic group, a halogen atom, a hydroxy group, a nitro group, and the like. Of these, a fluorine atom, an amino group, a nitro group, a fluorinated alkyl group, an alkyl group and alkoxy group are preferred.

The leaving group that bonds to the carbon atom of the aromatic ring of the aryl group or the heteroaryl group in $Ar^3$ is exemplified by a group obtained by removing an acidic hydrogen atom from an acid, and the like.

Examples of the acid include:

hydrohalogenic acids such as hydrofluoric acid, hydrochloric acid, hydrobromic acid and hydroiodic acid;

oxo acids such as sulfonic acid, phosphoric acid and carboxylic acid; and the like. Of these, in light of easy formation of the salt by the radioactive ray, sulfonic acid and hydrobromic acid are preferred, sulfonic acid is more preferred, trifluoromethanesulfonic acid and toluenesulfonic acid are still more preferred, and trifluoromethanesulfonic acid is particularly preferred.

In light of easy leaving of the acid in the compound (I-1), the upper limit of pKa of the acid generated from the leaving group is preferably 3, more preferably 1, still more preferably 0, and particularly preferably −1.

Examples of the aryl group in the aryl group having 6 to 30 ring atoms which may be represented by $Ar^3$ in which at least one leaving group bonds to the carbon atom of the aromatic ring include a phenyl group, a naphthyl group, an anthryl group, and the like. Of these, a phenyl group and a naphthyl group are preferred, and a phenyl group is more preferred.

Examples of the heteroaryl group in the heteroaryl group having 4 to 30 ring atoms represented by $Ar^3$ in which at least one leaving group bonds to the carbon atom of the aromatic ring include a pyridyl group, a pyrrolyl group, a furyl group, a thiophenyl group, and the like. Of these, a pyridyl group is preferred.

Examples of the substituent which may be included in the aryl group having 6 to 30 ring atoms which may be represented by $Ar^2$ in which at least one leaving group bonds to the carbon atom of the aromatic ring, and the heteroaryl group having 4 to 30 ring atoms which may be represented by $Ar^2$ in which at least one leaving group bonds to the carbon atom of the aromatic ring include a monovalent organic group, a halogen atom, a hydroxy group, a nitro group, and the like. Of these, a fluorine atom, an amino group, a nitro group, a fluorinated alkyl group, an alkyl group and alkoxy group are preferred.

In light of easy leaving of the acid in the compound (I-1), the lower limit of the number of covalent bonds constituting a shortest bond path between the carbon atom to which the hydrogen atom bonds in $Ar^2$ and the carbon atom to which the leaving group bonds in $Ar^3$ is preferably 5. The upper limit of the number of the aforementioned covalent bonds is preferably 6.

The compound (I-1) is exemplified by a compound represented by the following formula (1-1) (hereinafter, may be also referred to as "compound (I-1-1)"), and the like.

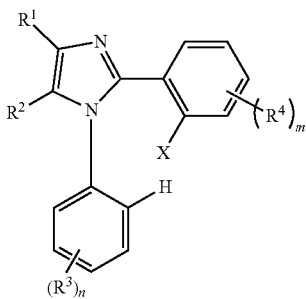

(1-1)

In the above formula (1-1), $R^1$ and $R^2$ each independently represent a hydrogen atom or a monovalent organic group having 1 to 20 carbon atoms, or $R^1$ and $R^2$ taken together represent a ring structure having 4 to 20 ring atoms together with the carbon atom to which $R^1$ and $R^2$ bond; $R^3$ represents a monovalent organic group having 1 to 20 carbon atoms; n is an integer of 0 to 4, wherein in a case in which n is no less than 2, a plurality of $R^3$s may be identical or different, and a plurality of $R^3$s may taken together represent a ring structure having 4 to 20 ring atoms together with the carbon chain to which $R^3$s bond; $R^4$ represents a monovalent organic group having 1 to 20 carbon atoms other than the leaving group; m is an integer of 0 to 4, wherein in a case in which m is no less than 2, a plurality of $R^4$s may be identical or different, and a plurality of $R^4$s may taken together represent a ring structure having 4 to 20 ring atoms together with the carbon chain to which $R^4$s bond; and X represents a monovalent leaving group described above.

The monovalent organic group having 1 to 20 carbon atoms which may be represented by $R^1$ or $R^2$ is exemplified by: a monovalent hydrocarbon group having 1 to 20 carbon atoms; a group (α) that includes a divalent hetero atom-containing group between two adjacent carbon atoms of the monovalent hydrocarbon group; a group obtained from the monovalent hydrocarbon group and the group (α) by substituting with a monovalent hetero atom-containing group a part or all of hydrogen atoms included therein; and the like.

Examples of the monovalent hydrocarbon group having 1 to 20 carbon atoms include similar groups to those exemplified as the hydrocarbon group which may be represented by $R^6$, $R^7$ or $R^8$ in the above formula (2), and the like.

Examples of the hetero atom constituting the monovalent and divalent hetero atom-containing group include an oxygen atom, a nitrogen atom, a sulfur atom, a phosphorus atom, a silicon atom, a halogen atom, and the like. Examples of the halogen atom include a fluorine atom, a chlorine atom, a bromine atom, an iodine atom, and the like.

Examples of the divalent hetero atom-containing group include —O—, —CO—, —S—, —CS—, —SO—, —SO$_2$—, groups obtained by combining at least two of the same, and the like, wherein R' represents a hydrogen atom or a monovalent hydrocarbon group. Of these, —O—, —S— and —NR'— are preferred.

Examples of the monovalent hetero atom-containing group include: halogen atoms such as a fluorine atom, a chlorine atom, a bromine atom and an iodine atom; a hydroxy group, a carboxy group, a cyano group, an amino group, a sulfanyl group (—SH), and the like. Of these, a hydroxy group and a cyano group are preferred.

Examples of the ring structure having 4 to 20 ring atoms which may be taken together represented by $R^1$ and $R^2$ together with the carbon atom to which $R^1$ and $R^2$ bond include:

aromatic carbon ring structures such as a benzene structure, a naphthalene structure, an anthracene structure and a phenanthrene structure;

aromatic heterocycle structures such as a pyridine structure, a quinoline structure, a thiophene structure and a furan structure;

alicyclic structures such as a cyclopentane structure and a cyclohexane structure;

aliphatic heterocycle structures such as an azacyclopentane structure and an azacyclohexane structure; and the like. Of these, the aromatic carbon ring structures are preferred, a benzene structure, a naphthalene structure and a phenanthrene structure are more preferred, and a phenanthrene structure is still more preferred.

Examples of the monovalent organic group having 1 to 20 carbon atoms represented by $R^3$ include monovalent organic groups similar to those exemplified in connection with $R^1$ and $R^2$, and the like.

In the formula (1-1), n is preferably 0 to 2, more preferably 0 and 1, and still more preferably 0.

Examples of the ring structure having 4 to 20 ring atoms which may be taken together represented by a plurality of $R^3$s together with the carbon chain to which the plurality of $R^3$s bond include ring structures similar to those exemplified in connection with the ring structure which may be taken together represented by $R^1$ and $R^2$, and the like.

Examples of the monovalent organic group having 1 to 20 carbon atoms other than the leaving group represented by $R^4$ include monovalent organic groups similar to those exemplified in connection with $R^1$ and $R^2$, and the like.

In the formula (1-1), m is preferably 0 to 2, more preferably 0 and 1, and still more preferably 0.

Examples of the ring structure having 4 to 20 ring atoms which may be taken together represented by a plurality of $R^4$s together with the carbon chain to which the plurality of $R^4$s bond include ring structures similar to those exemplified in connection with the ring structure which may be taken together represented by $R^1$ and $R^2$, and the like.

Examples of the monovalent leaving group represented by X include the monovalent groups among those exemplified as the leaving group that bonds to $Ar^3$ in the above formula (1), and the like. Of these, groups obtained by removing an acidic hydrogen atom from an oxo acid such as sulfonic acid, phosphoric acid or carboxylic acid are preferred, groups obtained by removing an acidic hydrogen atom from sulfonic acid are more preferred, groups obtained by removing an acidic hydrogen atom from trifluoromethanesulfonic acid or toluenesulfonic acid are still more preferred, and groups obtained by removing an acidic hydrogen atom from trifluoromethanesulfonic acid are particularly preferred.

Examples of the compound (I-1) include compounds represented by the following formulae (1-1-1) to (1-1-60) (hereinafter, may be also referred to as "compounds (I-1-1) to (I-1-60)"), and the like.

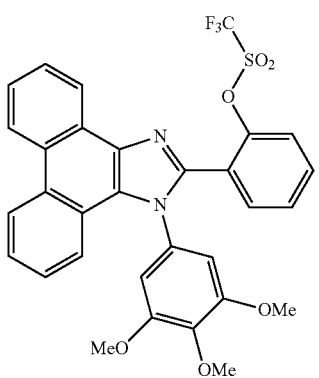 (1-1-1)
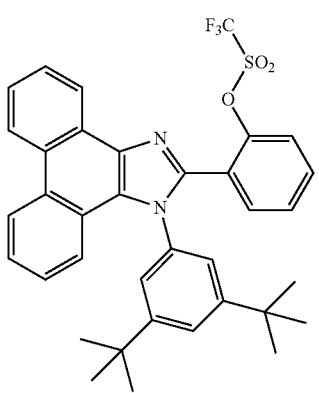 (1-1-2)
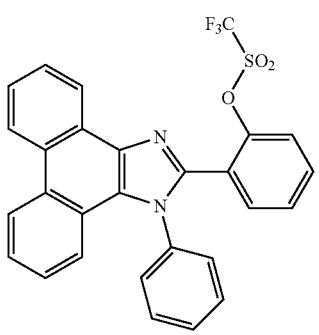 (1-1-3)
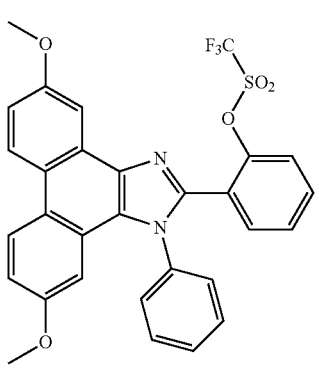 (1-1-4)
-continued
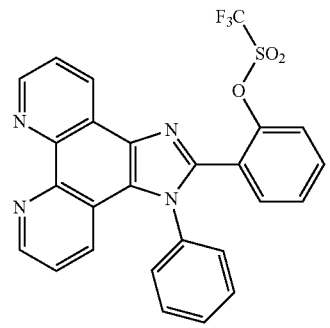 (1-1-5)
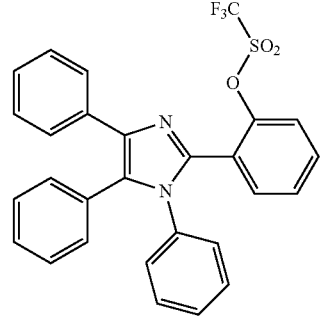 (1-1-6)
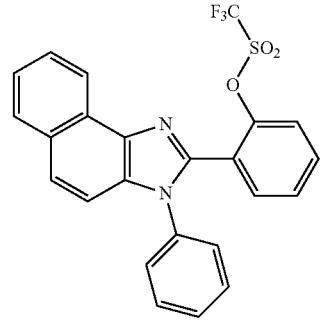 (1-1-7)
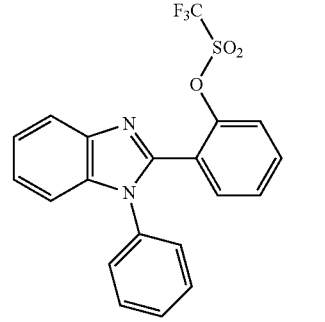 (1-1-8)
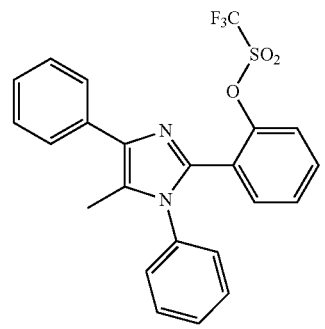 (1-1-9)

(1-1-10)
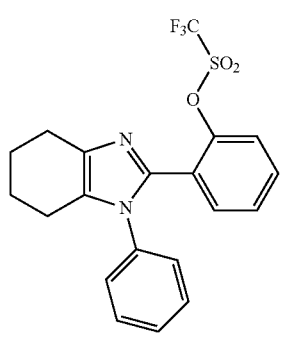
(1-1-14)
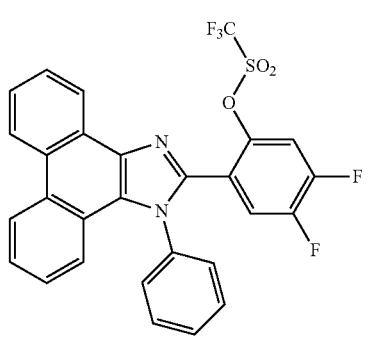
(1-1-11)
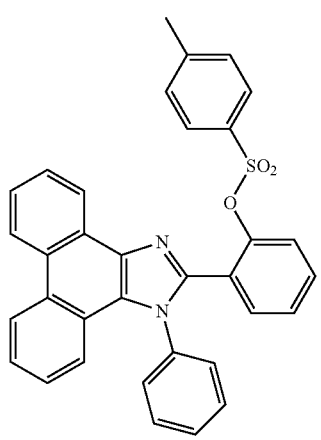
(1-1-15)
(1-1-12)
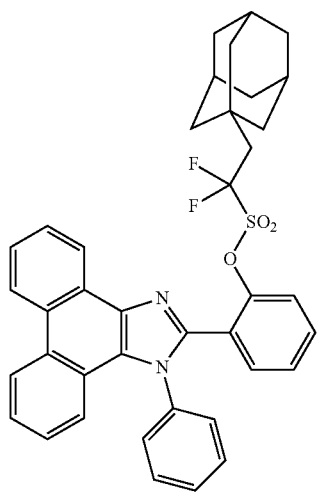
(1-1-16)
(1-1-13)
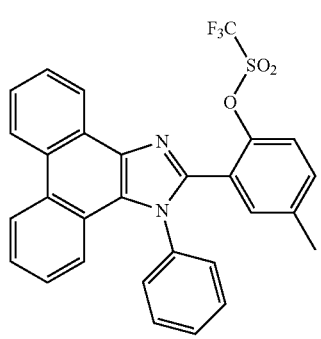
(1-1-17)

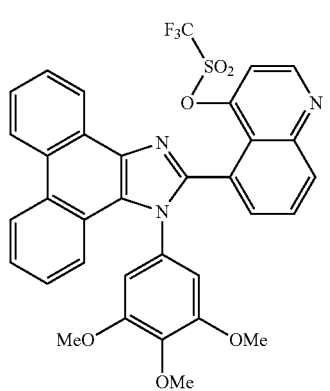
(1-1-18)
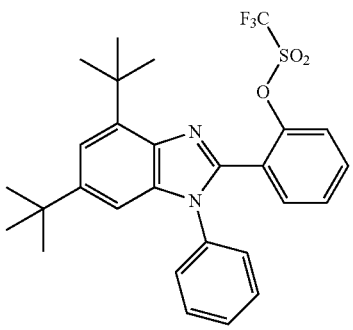
(1-1-22)
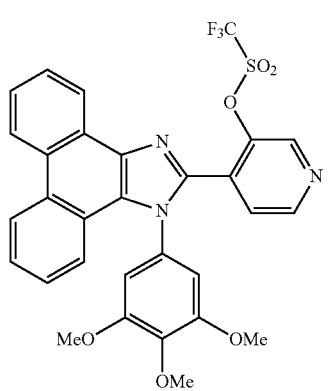
(1-1-19)
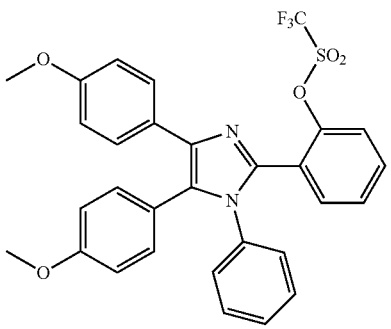
(1-2-23)
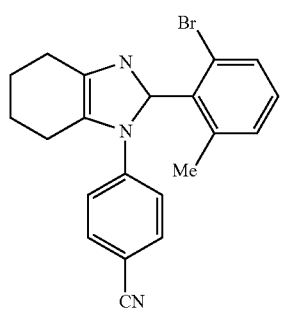
(1-1-20)
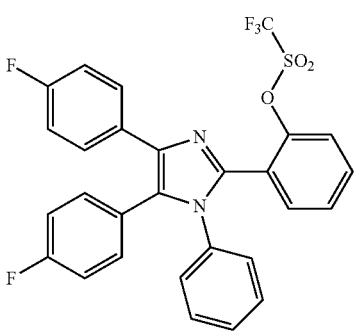
(1-1-24)
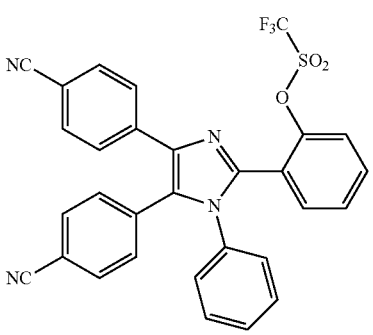
(1-1-25)
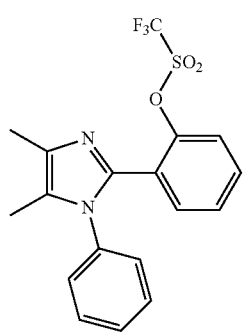
(1-1-21)
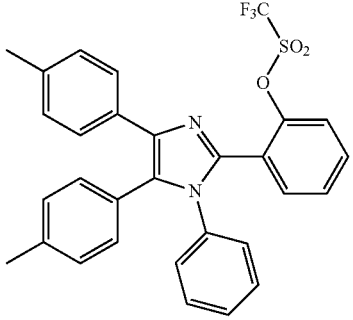
(1-1-26)

(1-1-27)
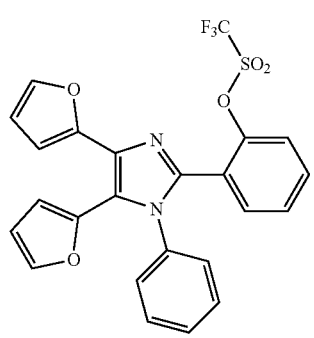
(1-1-28)
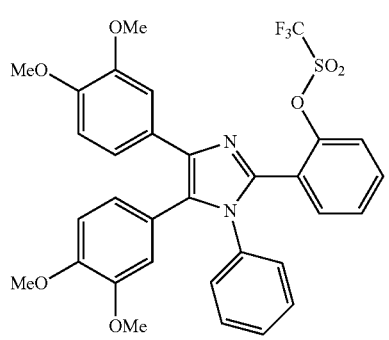
(1-1-29)
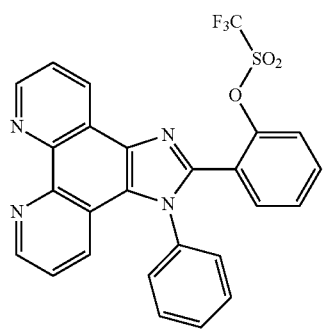
(1-1-30)
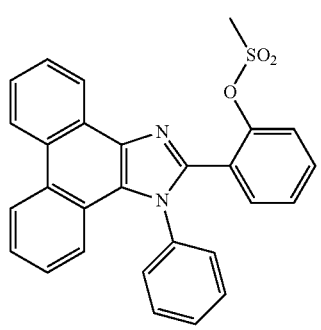
(1-1-31)
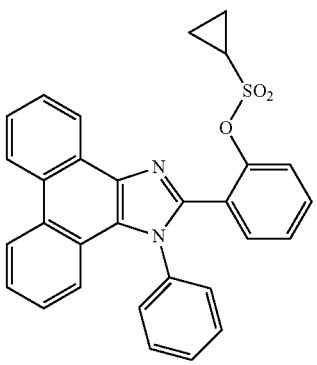
(1-1-32)
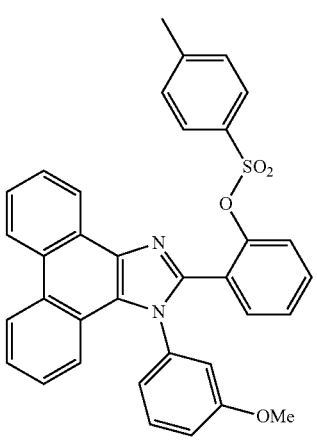
(1-1-33)
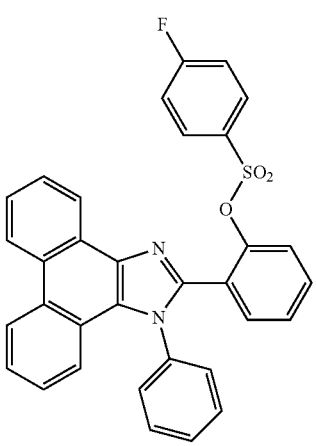

(1-1-34)
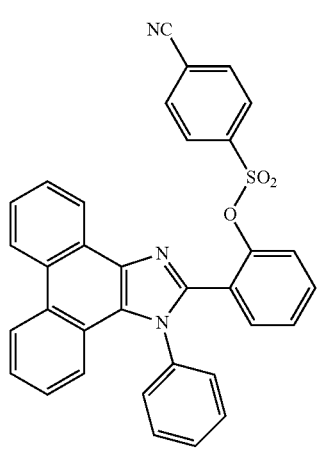
(1-1-35)
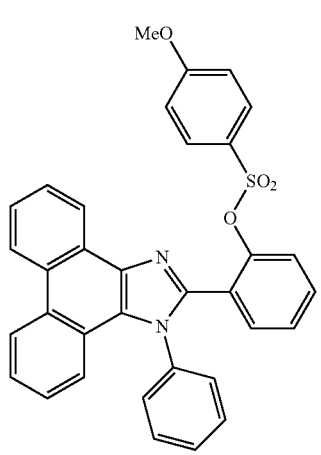
(1-1-36)
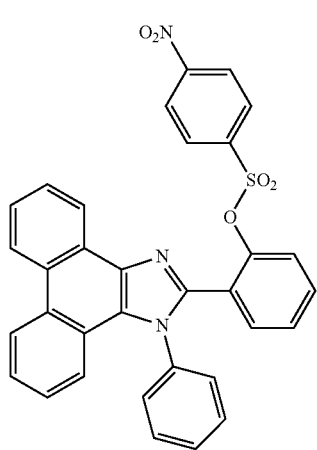
(1-1-37)
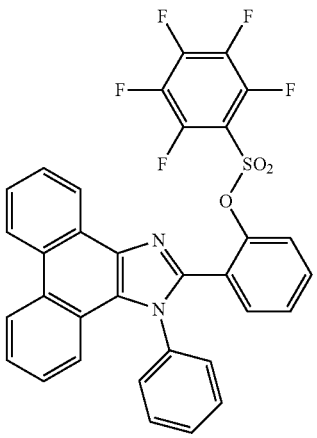
(1-1-38)
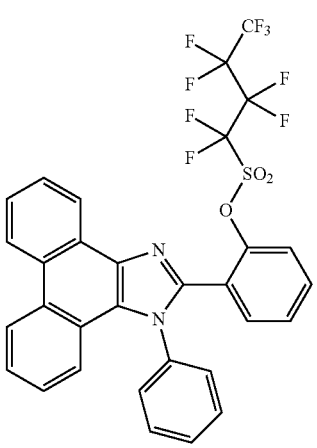
(1-1-39)
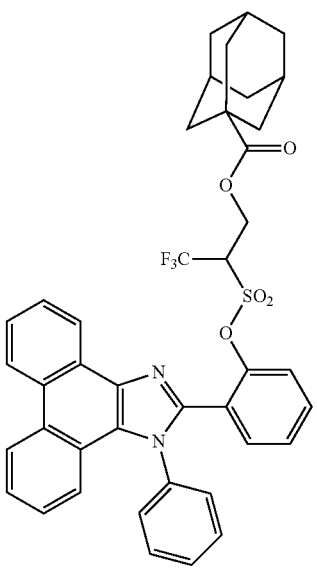

(1-1-40)
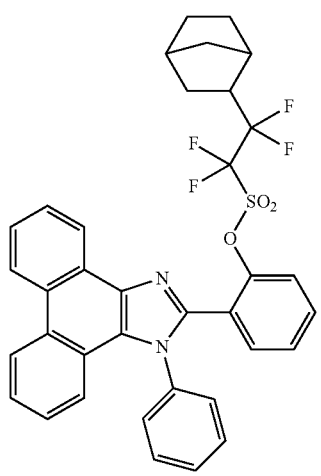
(1-1-41)
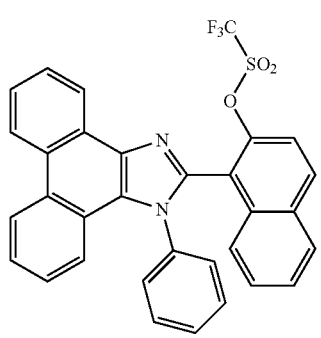
(1-1-42)
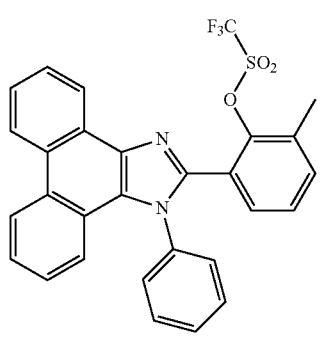
(1-1-43)
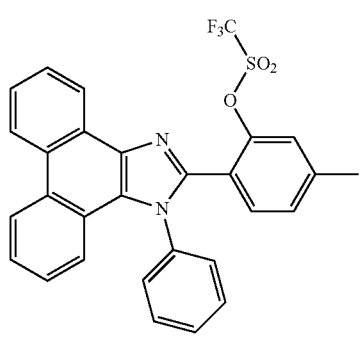
(1-1-44)
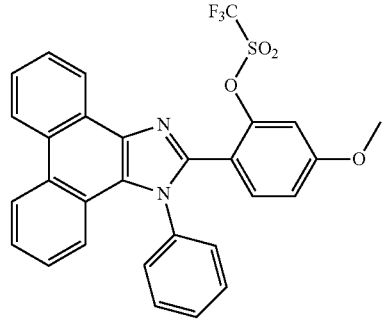
(1-1-45)
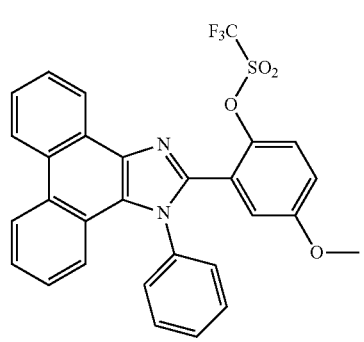
(1-1-46)
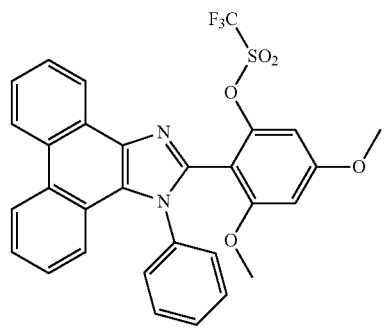
(1-1-47)
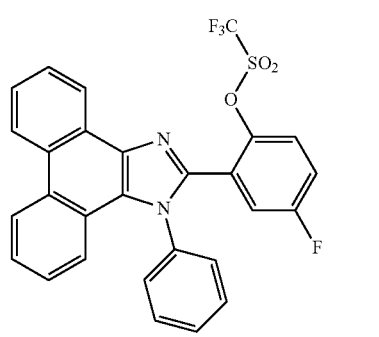
(1-1-48)
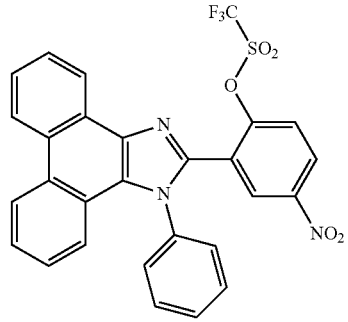

(1-1-49)
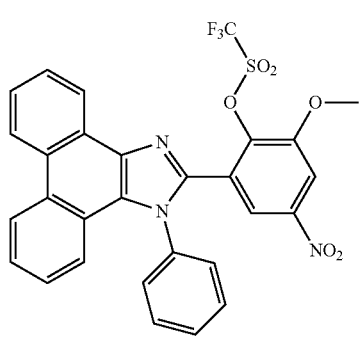
(1-1-50)
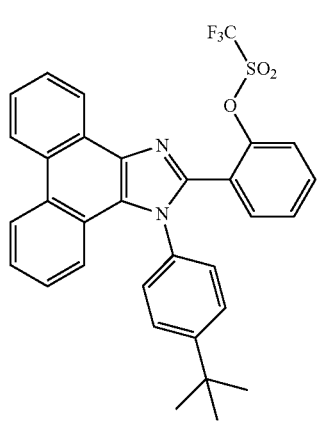
(1-1-51)
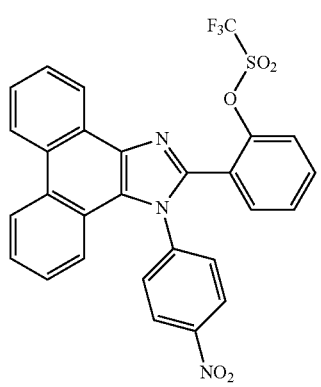
(1-1-52)
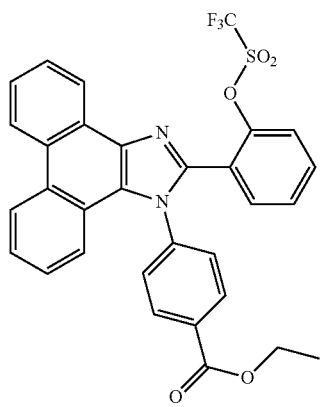
(1-1-53)
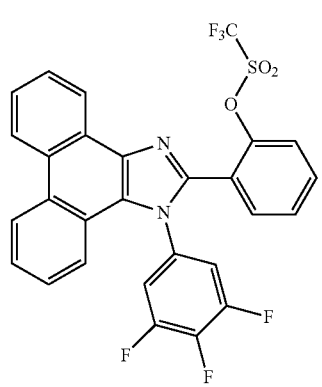
(1-1-54)
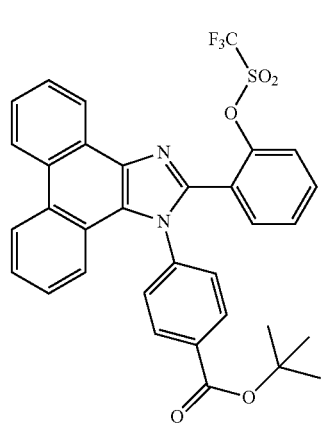
(1-1-55)
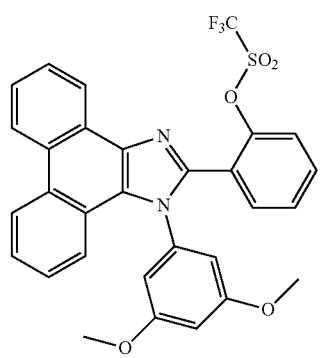
(1-1-56)
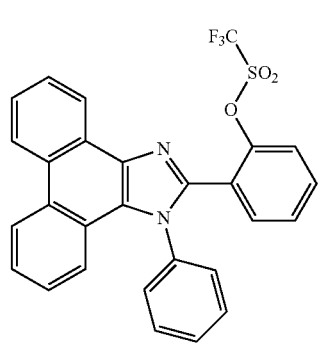

-continued

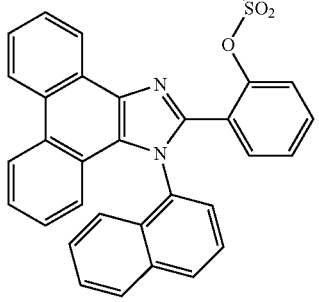
(1-1-57)

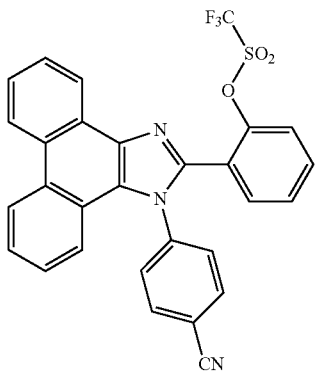
(1-1-58)

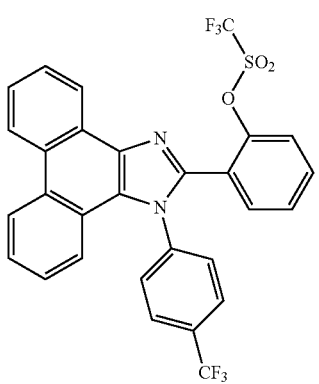
(1-1-59)

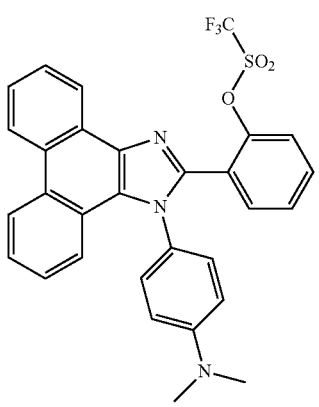
(1-1-60)

Of the compounds (C), as shown by the following schema, the compound (I-1-1) may be synthesized by allowing a compound represented by the following formula (a), a compound represented by the following formula (b) and a compound represented by the following formula (c) to react in a solvent such as acetic acid in the presence of ammonium acetate, for example. The compounds (C) other than the compound (I-1-1) may be also synthesized in a similar manner.

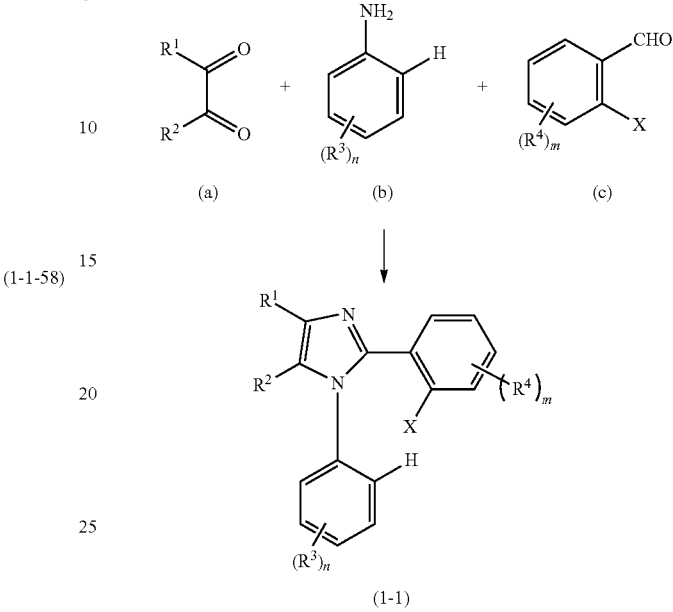

The lower limit of the content of the compound (C) with respect to 100 parts by mass of the polymer (A) is preferably 0.1 parts by mass, more preferably 0.2 parts by mass, still more preferably 0.5 parts by mass, and particularly preferably 1 part by mass. The upper limit of the aforementioned content is preferably 20 parts by mass, more preferably 10 parts by mass, still more preferably 5 parts by mass, and particularly preferably 3 parts by mass. When the content of the compound (C) falls within the above range, more improvements of the LWR performances, etc., of the radiation-sensitive resin composition are enabled. The radiation-sensitive resin composition may contain one or two or more types of the compound (C).

(D) Polymer

The polymer (D) has a greater mass percentage content of fluorine atoms than that of the polymer (A). Since the polymer (D) has a greater mass percentage content of fluorine atoms than that of the polymer (A), when a resist film is formed, oil repellent characteristics of the polymer (D) tend to allow the polymer (D) to be localized in the surface region of the resist film. Consequently, according to the radiation-sensitive resin composition, elution of an acid generating agent, an acid diffusion controller and the like into a liquid immersion medium may be inhibited in liquid immersion lithography. In addition, according to the radiation-sensitive resin composition, due to water repellent characteristics of the polymer (D), an advancing contact angle of a liquid immersion medium on the resist film can be controlled to fall within a desired range, thereby enabling generation of bubble defects to be inhibited. Further, according to the radiation-sensitive resin composition, a greater receding contact angle of the liquid immersion medium on the resist film is attained, whereby an exposure by high speed scanning without being accompanied by residual water beads is enabled. Due to thus containing the polymer (D), the radiation-sensitive resin composition is capable of forming a resist film suited for liquid immersion lithography processes.

The lower limit of the mass percentage content of fluorine atoms of the polymer (D) is preferably 1% by mass, more preferably 2% by mass, still more preferably 4% by mass, and particularly preferably 7% by mass. The upper limit of the aforementioned mass percentage content is preferably 60% by mass, more preferably 50% by mass, still more preferably 40% by mass, and particularly preferably 30% by mass. When the mass percentage content of fluorine atoms falls within the above range, the localization of the polymer (D) in the resist film can be regulated more appropriately. It is to be noted that the mass percentage content of fluorine atoms of the polymer may be calculated based on the structure of the polymer determined by $^{13}$C-NMR spectroscopy.

The mode of the incorporation of the fluorine atom in the polymer (D) is not particularly limited, and the fluorine atom may bond to any of the main chain, a side chain or the end of the polymer (D). The polymer (D) preferably has a structural unit that includes a fluorine atom (hereinafter, may be also referred to as "structural unit (F)"). In light of an improvement of the inhibitory ability of defects of the radiation-sensitive resin composition, the polymer (D) preferably has, in addition to the structural unit (F), a structural unit that includes an acid-labile group. The structural unit that includes an acid-labile group is exemplified by the structural unit (I) in the polymer (A), and the like.

Moreover, the polymer (D) preferably has an alkali-labile group. When the polymer (D) has the alkali-labile group, the surface of the resist film can be changed effectively from hydrophobic to hydrophilic in a development with an alkali, whereby the inhibitory ability of defects of the radiation-sensitive resin composition may be more improved. The "alkali-labile group" as referred to herein means a group that substitutes for the hydrogen atom of a carboxy group, a hydroxy group or the like and may be dissociated in an alkaline aqueous solution (for example, a 2.38% by mass aqueous tetramethylammonium hydroxide solution at 23° C.).

The structural unit (F) is preferably a structural unit represented by the following formula (f-1) (hereinafter, may be also referred to as "structural unit (F-1)") or a structural unit represented by the following for (f-2) (hereinafter, may be also referred to as "structural unit (F-2)"). The structural unit (F) may contain one or two or more types of each of the structural unit (F-1) and the structural unit (F-2).

Structural Unit (F-1)

The structural unit (F-1) is represented by the following formula (f-1). When the polymer (D) has the structural unit (F-1), the mass percentage content of fluorine atoms can be adjusted.

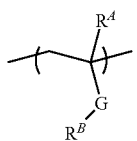

(f-1)

In the above formula (f-1), $R^A$ represents a hydrogen atom, a fluorine atom, a methyl group or a trifluoromethyl group; G represents a single bond, an oxygen atom, a sulfur atom, —COO—, —SO$_2$ONH—, —CONH— or —OCONH—; and $R^B$ represents a monovalent fluorinated chain hydrocarbon group having 1 to 6 carbon atoms or a monovalent fluorinated alicyclic hydrocarbon group having 4 to 20 carbon atoms.

In light of the copolymerizability of a monomer that gives the structural unit (F-1), $R^A$ represents preferably a hydrogen atom or a methyl group, and more preferably a methyl group.

G represents preferably —COO—, —SO$_2$ONH—, —CONH— or —OCONH—, and more preferably —COO—.

Examples of the monovalent fluorinated chain hydrocarbon group having 1 to 6 carbon atoms which may be represented by $R^B$ include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the monovalent fluorinated alicyclic hydrocarbon group having 4 to 20 carbon atoms which may be represented by $R^B$ include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

$R^B$ represents preferably a fluorinated chain hydrocarbon group, more preferably a 2,2,2-trifluoroethyl group or a 1,1,1,3,3,3-hexafluoro-2-propyl group, and still more preferably a 2,2,2-trifluoroethyl group.

In a case in which the polymer (D) has the structural unit (F-1), the lower limit of the proportion of the structural unit (F-1) with respect to the total structural units constituting the polymer (D) is preferably 10 mol %, and more preferably 20 mol %. The upper limit of the aforementioned proportion is preferably 90 mol %, more preferably 70 mol %, and still more preferably 50 mol %. When the proportion of the structural unit (F-1) falls within the above range, the mass percentage content of fluorine atoms of the polymer (D) can be adjusted further appropriately.

Structural Unit (F-2)

The structural unit (F-2) is represented by the following formula (f-2). When the polymer (D) has the structural unit (F-2), the solubility in an alkaline developer solution is improved, thereby enabling the occurrence of development defects to be inhibited. The structural unit (F-2) is generally classified into two forms: (x) a structural unit having an alkali-soluble group; and (y) a structural unit having a group that is to be dissociated by an action of an alkali to increase the solubility in an alkaline developer solution (hereinafter, may be also referred to as "alkali-labile group").

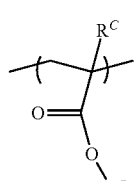

(f-2)

For both the forms (x) and (y), in the above formula (f-2), $R^C$ represents a hydrogen atom, a fluorine atom, a methyl group or a trifluoromethyl group; $R^D$ represents a single bond, a hydrocarbon group having 1 to 20 carbon atoms and having a valency of (s+1), a structure obtained by incorporating an oxygen atom, a sulfur atom, —NR'—, a carbonyl group, —COO— or —CONH— bonded to the end on the $R^E$ side of this hydrocarbon group, or a structure obtained by substituting with an organic group having a hetero atom a part of the hydrogen atoms included in this hydrocarbon group; R' represents a hydrogen atom or a monovalent hydrocarbon group having 1 to 10 carbon atoms; and s is an integer of 1 to 3, wherein in a case in which s is 1, $R^D$ is other than a single bond.

In a case in which the structural unit (F-2) has the alkali-soluble group (x), $R^F$ represents a hydrogen atom; $A^1$ represents an oxygen atom, —COO—* or —SO$_2$O—*, wherein * denotes a site bonded to $R^F$; $W^1$ represents a single bond, a hydrocarbon group having 1 to 20 carbon atoms or a divalent fluorinated hydrocarbon group, wherein in a case in which $A^1$ represents an oxygen atom, $W^1$ represents a fluorinated hydrocarbon group having a fluorine atom or a fluoroalkyl group at the carbon atom bonded to $A^1$; and $R^E$ represents a single bond or a divalent organic group having 1 to 20 carbon atoms, wherein in a case in which s is 2 or 3, a plurality of $R^E$s may be identical or different, a plurality of $W^1$s may be identical or different, a plurality of A's may be identical or different and a plurality of $R^E$s may be identical or different. When the structural unit (F-2) has the alkali-soluble group (x), affinity to alkaline developer solutions are increased, thereby enabling development defects to be prevented. In the structural unit (F-2) having the alkali-soluble group (x), it is particularly preferred that: $A^1$ represents an oxygen atom; and $W^1$ represents a 1,1,1,3,3,3-hexafluoro-2,2-propanediyl group.

In a case in which the structural unit (F-2) has the alkali-labile group (y), $R^F$ represents a monovalent organic group having 1 to 30 carbon atoms; $A^1$ represents an oxygen atom, —NR$^{aa}$—, —COO—* or —SO$_2$O—*; $R^{aa}$ represents a hydrogen atom or a monovalent hydrocarbon group having 1 to 10 carbon atoms, wherein * denotes a site bonded to $R^F$; $W^1$ represents a single bond or divalent fluorinated hydrocarbon group having 1 to 20 carbon atoms; and $R^E$ represents a single bond or a divalent organic group having 1 to 20 carbon atoms, wherein in a case in which $A^1$ represents —COO—* or —SO$_2$O—*, $W^1$ or $R^F$ has a fluorine atom on the carbon atom bonded to $A^1$ or on the carbon atom adjacent thereto, and in a case in which $A^1$ represents an oxygen atom, $W^1$ and $R^E$ each represent a single bond, $R^D$ represents a structure in which a carbonyl group bonds to the end on the $R^E$ side of the hydrocarbon group having 1 to 20 carbon atoms, $R^F$ represents an organic group having a fluorine atom, and wherein in a case in which s is 2 or 3, a plurality of $R^E$s may be identical or different, a plurality of $W^1$s may be identical or different, a plurality of A's may be identical or different and a plurality of $R^F$s may be identical or different. When the structural unit (F-2) has the alkali-labile group (y), the surface of the resist film can be changed from hydrophobic to hydrophilic in a development step with an alkali. As a result, the affinity to developer solution is greatly increased, whereby more efficient inhibition of development defects is enabled. In the structural unit (F-2) having the alkali-labile group (y) it is particularly preferred that: $A^1$ represents —COOO—*; and $R^F$ or V, or both $R^F$ and $W^1$ has/have a fluorine atom.

In light of the copolymerizability of a monomer that gives the structural unit (F-2), and the like, $R^C$ represents preferably a hydrogen atom or a methyl group, and more preferably a methyl group.

Examples of the hydrocarbon group having 1 to 20 carbon atoms and having a valency of (s+1) which may be represented by $R^D$ include groups derived from the monovalent hydrocarbon group having 1 to 20 carbon atoms exemplified in connection with $R^6$ to $R^8$ in the above formula (2) by removing s hydrogen atom(s) therefrom, and the like.

In the above formula (f-2), s is preferably 1 and 2, and more preferably 1.

In the case in which s is 1, $R^D$ represents preferably a single bond or a divalent hydrocarbon group, more preferably a single bond or an alkanediyl group, still more preferably a single bond or an alkanediyl group having 1 to 4 carbon atoms, and particularly preferably a single bond, a methanediyl group or a propanediyl group.

Examples of the divalent organic group having 1 to 20 carbon atoms which may be represented by $R^E$ include groups similar to those exemplified as the divalent organic group having 1 to 20 carbon atoms which may be represented by $L^1$ in the above formula (2'), and the like.

$R^E$ represents preferably a single bond or a group that has a lactone structure, more preferably a single bond or a group that has a polycyclic lactone structure, and more preferably a single bond or a group that has a norbornanelactone structure.

Examples of the divalent fluorinated chain hydrocarbon group having 1 to 20 carbon atoms, which may be represented by $W^1$, include:

fluorinated alkanediyl groups such as a fluoromethanediyl group, a difluoromethanediyl group, a fluoroethanediyl group, a difluoroethanediyl group, a tetrafluoroethanediyl group, a hexafluoropropanediyl group and an octafluorobutanediyl group;

fluorinated alkenediyl groups such as a fluoroethenediyl group and a difluoroethenediyl group; and the like. Of these, the fluorinated alkanediyl group is preferred, and the difluoromethanediyl group is more preferred.

$A^1$ represents preferably an oxygen atom, —COO—* or —SO$_2$O—*, and more preferably —COO—*.

The monovalent organic group having 1 to 30 carbon atoms, which may be represented by $R^F$, is exemplified by an alkali-labile group, an acid-labile group, a hydrocarbon group having 1 to 30 carbon atoms, and the like. Of these, $R^F$ represents preferably the alkali-labile group. When $R^F$ represents the alkali-labile group, the surface of the resist film can be changed from hydrophobic to hydrophilic more effectively in the development with an alkali, whereby the inhibitory ability of defects may be further improved.

In a case in which $R^F$ represents the alkali-labile group, $R^F$ is preferably represented by any of the following formulae (iii) to (v) (hereinafter, may be also referred to as "groups (iii) to (v)").

(iii)

In the above formula (iii), $R^{5a}$ and $R^{5b}$ each independently represent a monovalent organic group having 1 to 20 carbon atoms, or $R^{5a}$ and $R^{5b}$ taken together represent an alicyclic structure having 3 to 20 ring atoms, together with the carbon atom to which $R^{5a}$ and $R^{5b}$ bond.

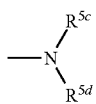 (iv)

In the above formula (iv), $R^{5c}$ and $R^{5d}$ each independently represent a monovalent organic group having 1 to 20 carbon atoms, or $R^{5c}$ and $R^{5d}$ taken together represent a heterocyclic structure having 3 to 20 ring atoms, together with the nitrogen atom to which $R^{5c}$ and $R^{5d}$ bond.

 (v)

In the above formula (v), $R^{5e}$ represents a monovalent hydrocarbon group having 1 to 20 carbon atoms or a monovalent fluorinated hydrocarbon group having 1 to 20 carbon atoms.

Examples of the monovalent organic group having 1 to 20 carbon atoms and the monovalent hydrocarbon group having 1 to 20 carbon atoms include groups similar to those exemplified in connection with $R^2$ in the above formula (I), and the like.

The monovalent fluorinated hydrocarbon group having 1 to 20 carbon atoms is exemplified by groups derived from the groups exemplified as the monovalent hydrocarbon group having 1 to 20 carbon atoms by substituting a part or all of hydrogen atoms included therein with a fluorine atom, and the like.

As the group (iii), groups represented by the following formulae (iii-1) to (iii-4) (hereinafter, may be also referred to as "groups (iii-1) to (iii-4)") are preferred. As the group (iv), a group represented by the following formula (iv-1) (hereinafter, may be also referred to as "group (iv-1)") is preferred. As the group (v), groups represented by the following formulae (v-1) to (v-5) (hereinafter, may be also referred to as "groups (v-1) to (v-5)") are preferred.

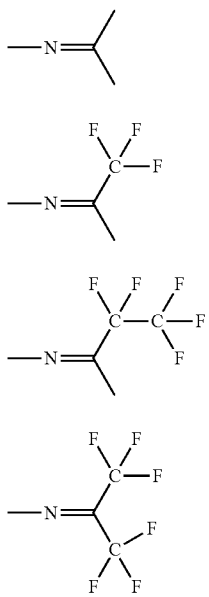

(iii-1)
(iii-2)
(iii-3)
(iii-4)

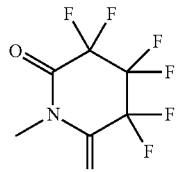 (iv-1)

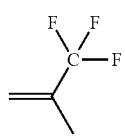 (v-1)

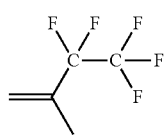 (v-2)

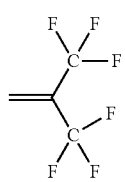 (v-3)

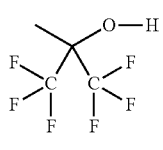 (v-4)

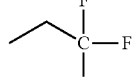 (v-5)

Of these, the groups (v-3) and (v-5) are preferred.

In addition, it is preferred that $R^F$ represents a hydrogen atom, since the affinity of the polymer (D) for an alkaline developer solution may be improved. In this case, when $A^1$ represents an oxygen atom and $W^1$ represents a 1,1,1,3,3,3-hexafluoro-2,2-propanediyl group, the aforementioned affinity may be further improved.

In a case in which the polymer (D) has the structural unit (F-2), the lower limit of the proportion of the structural unit (F-2) contained with respect to the total structural units constituting the polymer (D) is preferably 10 mol %, more preferably 20 mol %, and still more preferably 40 mol %. The upper limit of the aforementioned proportion is preferably 90 mol %, more preferably 85 mol %, and still more preferably 80 mol %. When the proportion of the structural unit (F-2) falls within the above range, a more appropriate change of the surface property of a resist film formed from the radiation-sensitive resin composition is enabled from water repellent to hydrophilic through the development with an alkali.

The lower limit of the proportion of the structural unit (F) contained with respect to the total structural units constituting the polymer (D) is preferably 10 mol %, more preferably 20 mol %, and still more preferably 25 mol %. The upper limit of the aforementioned proportion is preferably 90 mol %, more preferably 85 mol %, and still more preferably 80 mol %.

The lower limit of the proportion of the structural unit that includes an acid-labile group in the polymer (D) with respect to the total structural units constituting the polymer (D) is preferably 10 mol %, more preferably 20 mol %, and still more preferably 50 mol %. The upper limit of the aforementioned proportion is preferably 90 mol %, more preferably 80 mol %, and still more preferably 75 mol %. When the proportion of the structural unit that includes an acid-labile group falls within the above range, the inhibitory ability of defects of the radiation-sensitive resin composition may be further improved.

In a case in which the radiation-sensitive resin composition contains the polymer (D), the lower limit of the content of the polymer (D) with respect to 100 parts by mass of the polymer (A) is preferably 0.1 parts by mass, more preferably 0.5 parts by mass, still more preferably 1 part by mass, and particularly preferably 2 parts by mass. The upper limit of the aforementioned content is preferably 30 parts by mass, more preferably 20 parts by mass, still more preferably 15 parts by mass, and particularly preferably 10 parts by mass. The radiation-sensitive resin composition may contain one or two or more types of the polymer (D).

The polymer (D) may be synthesized according to a method similar to the aforementioned method for the polymer (A).

The lower limit of the Mw as determined by GPC of the polymer (D) is preferably 1,000, more preferably 3,000, still more preferably 4,000, and particularly preferably 5,000. The upper limit of the Mw is preferably 50,000, more preferably 30,000, still more preferably 20,000, and particularly preferably 10,000. When the Mw of the polymer (D) falls within the above range, the coating characteristics and the inhibitory ability of defects of the radiation-sensitive resin composition may be improved.

The lower limit of the ratio (Mw/Mn) of the Mw to the Mn as determined by GPC of the polymer (D) is typically 1, and preferably 1.2. The upper limit of the aforementioned ratio is preferably 5, more preferably 3, and still more preferably 2.

(E) Solvent

The radiation-sensitive resin composition typically contains the solvent (E). The solvent (E) is not particularly limited as long as the solvent (E) is capable of dissolving or dispersing at least the polymer (A), the acid generator (B) and the compound (C), as well as optional components and the like which are contained as needed.

The solvent (E) is exemplified by an alcohol solvent, an ether solvent, a ketone solvent, an amide solvent, an ester solvent, a hydrocarbon solvent, and the like.

Examples of the alcohol solvent include:

aliphatic monohydric alcohol solvents having 1 to 18 carbon atoms such as 4-methyl-2-pentanol and n-hexanol;

alicyclic monohydric alcohol solvents having 3 to 18 carbon atoms such as cyclohexanol;

polyhydric alcohol solvents having 2 to 18 carbon atoms such as 1,2-propylene glycol;

polyhydric alcohol partial ether solvents having 3 to 19 carbon atoms such as propylene glycol monomethyl ether; and the like.

Examples of the ether solvent include:

dialkyl ether solvents such as diethyl ether, dipropyl ether, dibutyl ether, dipentyl ether, diisoamyl ether, dihexyl ether and diheptyl ether;

cyclic ether solvents such as tetrahydrofuran and tetrahydropyran;

aromatic ring-containing ether solvents such as diphenyl ether and anisole; and the like.

Examples of the ketone solvent include:

chain ketone solvents such as acetone, methyl ethyl ketone, methyl n-propyl ketone, methyl n-butyl ketone, diethyl ketone, methyl iso-butyl ketone, 2-heptanone, ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonylacetone and acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

monocarboxylic acid ester solvents such as n-butyl acetate and ethyl lactate;

polyhydric alcohol carboxylate solvents such as propylene glycol acetate;

polyhydric alcohol partial ether carboxylate solvents such as propylene glycol monomethyl ether acetate;

polyhydric carboxylic acid diester solvents such as diethyl oxalate;

lactone solvents such as γ-butyrolactone and δ-valerolactone;

carbonate solvents such as dimethyl carbonate, diethyl carbonate, ethylene carbonate and propylene carbonate; and the like.

Examples of the hydrocarbon solvent include:

aliphatic hydrocarbon solvents having 5 to 12 carbon atoms such as n-pentane and n-hexane;

aromatic hydrocarbon solvents having 6 to 16 carbon atoms such as toluene and xylene; and the like.

As the solvent (E), the ester solvent and the ketone solvent are preferred, the polyhydric alcohol partial ether carboxylate solvent, the lactone solvent, the monocarboxylic acid ester solvent and the cyclic ketone solvent are more preferred, polyhydric alcohol partial alkyl ether acetate, butyrolactone, a lactic acid ester and cycloalkanone are still more preferred, and propylene glycol monomethyl ether acetate, γ-butyrolactone, ethyl lactate and cyclohexanone are particularly preferred. The radiation-sensitive resin composition may contain one or two or more types of the solvent (E).

Other Optional Component

The radiation-sensitive resin composition may contain other optional component than the components (A) to (E). The other optional component is exemplified by an acid diffusion controller other than the compound (C) (hereinafter, may be also referred to as "other acid diffusion controller"), a surfactant, an alicyclic skeleton-containing compound, a sensitizing agent, and the like. These other optional components each may be used either alone of one type, or in combination of two or more types thereof.

Other Acid Diffusion Control Agent

The radiation-sensitive resin composition may contain other acid diffusion controller than the compound (C) within a range not leading to impairment of the effects of the present invention. The other acid diffusion controller may be contained in the radiation-sensitive resin composition either in the form of a free compound (hereinafter, may be referred to as "other acid diffusion control agent" as appropriate), in the form incorporated as a part of the polymer, or may be in both of these forms.

The other acid diffusion control agent is exemplified by a compound represented by the following formula (5) (hereinafter, may be also referred to as "nitrogen-containing compound (I)"), a compound having two nitrogen atoms in a single molecule (hereinafter, may be also referred to as "nitrogen-containing compound (II)"), a compound having three nitrogen atoms (hereinafter, may be also referred to as "nitrogen-containing compound (III)"), an amide group-containing compound, a urea compound, a nitrogen-containing heterocyclic compound, and the like.

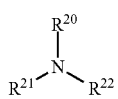
(5)

In the above formula (5), $R^{20}$, $R^{21}$ and $R^{22}$ each independently represent a hydrogen atom, a substituted or unsubstituted alkyl group, a substituted or unsubstituted monovalent alicyclic saturated hydrocarbon group, a substituted or unsubstituted aryl group or a substituted or unsubstituted aralkyl group.

Examples of the nitrogen-containing compound (I) include: monoalkylamines such as n-hexylamine; dialkylamines such as di-n-butylamine; trialkylamines such as triethylamine; aromatic amines such as aniline and 2,6-di-i-propylaniline, and the like.

Examples of the nitrogen-containing compound (II) include ethylene diamine, N,N,N',N'-tetramethylethylenediamine, and the like.

Examples of the nitrogen-containing compound (III) include: polyamine compounds such as polyethyleneimine and polyallylamine; polymers of dimethylaminoethylacrylamide, etc.; and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include: pyridines such as pyridine and 2-methylpyridine; morpholines such as N-propylmorpholine and N-(undecylcarbonyloxyethyl)morpholine; pyrazine; pyrazole; imidazoles such as benzimidazole and 2-phenylbenzimidazole; and the like.

As a nitrogen-containing organic compound, a compound having an acid-labile group may be also used. Examples of the nitrogen-containing organic compound having an acid-labile group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-t-butoxycarbonyl-4-hydroxypiperidine, N-t-amyloxycarbonyl-4-hydroxypiperidine, and the like.

Alternatively, a photolabile base which is sensitized upon an exposure to generate an acid may also be used as the other acid diffusion control agent. The photolabile base is exemplified by an onium salt compound that loses acid diffusion controllability through degradation upon an exposure, and the like. Examples of the onium salt compound include a sulfonium salt compound represented by the following formula (6-1), an iodonium salt compound represented by the following formula (6-2), and the like.

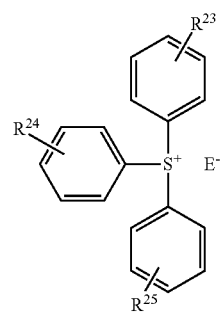
(6-1)

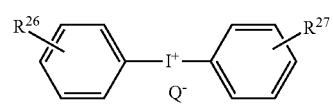
(6-2)

In the above formulae (6-1) and (6-2), $R^{23}$ to $R^{27}$ each independently represent a hydrogen atom, an alkyl group, an alkoxy group, a hydroxy group or a halogen atom; $E^-$ and $Q^-$ each independently represent $OH^-$, $R^{\beta}-COO^-$, $R^{\gamma}-SO_3^-$; or an anion represented by the following formula (6-3); $R^{\beta}$ represents an alkyl group, an aryl group or an aralkyl group; and $R^{\gamma}$ represents an alkyl group or an aralkyl group.

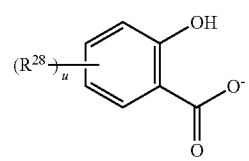
(6-3)

In the above formula (6-3), $R^{28}$ represents a linear or branched alkyl group having 1 to 12 carbon atoms, a linear or branched fluorinated alkyl group having 1 to 12 carbon atoms or a linear or branched alkoxy group having 1 to 12 carbon atoms; and u is an integer of 0 to 2, wherein in a case in which u is 2, two $R^{28}$s may be identical or different.

Examples of the photodegradable base include compounds represented by the following formulae, and the like.

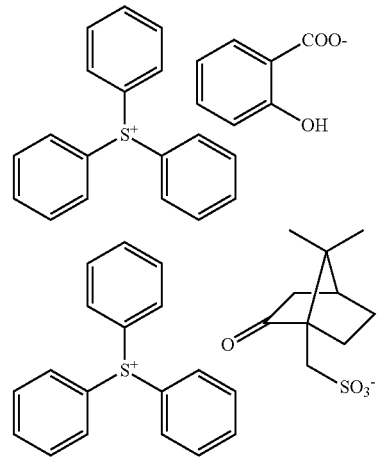

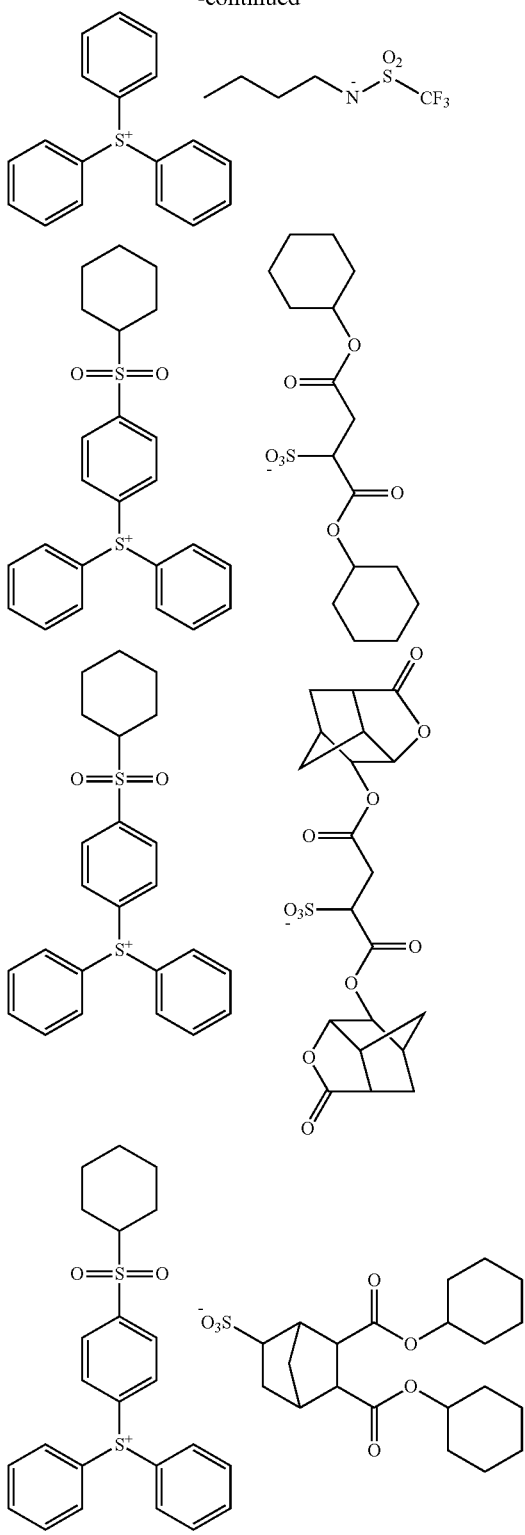

Of these, as the photodegradable base, a sulfonium salt is preferred, a triarylsulfonium salt is more preferred, and triphenylsulfonium salicylate and triphenylsulfonium 10-camphorsulfonate are still more preferred.

In a case in which the radiation-sensitive resin composition contains the other acid diffusion control agent, the lower limit of the content of the other acid diffusion control agent with respect to 100 parts by mass of the compound (C) is preferably 100 parts by mass, more preferably 50 parts by mass, and still more preferably 20 parts by mass. Whereas, the upper limit of the content of the other acid diffusion control agent with respect to 100 parts by mass of the polymer (A) is preferably 20 parts by mass, more preferably 10 parts by mass, and still more preferably 5 parts by mass.

Surfactant

The surfactant achieves the effect of improving the coating characteristics, striation, developability, and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; commercially available products such as "KP341" available from Shin-Etsu Chemical Co., Ltd., "Polyflow No. 75" and "Polyflow No. 95" available from Kyoeisha Chemical Co., Ltd., "EFTOP EF301", "EFTOP EF303" and "EFTOP EF352" available from Tochem Products Co. Ltd., "Megaface F171" and "Megaface F173" available from DIC, "Fluorad FC430" and "Fluorad FC431" available from Sumitomo 3M Limited, "ASAHI GUARD AG710", "Surflon S-382", "Surflon SC-101", "Surflon SC-102", "Surflon SC-103", "Surflon SC-104", "Surflon SC-105" and "Surflon SC-106" available from Asahi Glass Co., Ltd.; and the like. The upper limit of the content of the surfactant with respect to 100 parts by mass of the polymer (A) is preferably 2 parts by mass, and more preferably 1 part by mass.

Alicyclic Skeleton-Containing Compound

The alicyclic skeleton-containing compound achieves the effect of improving dry-etching resistance, a pattern configuration, adhesiveness to a substrate, and the like.

Sensitizing Agent

The sensitizing agent exhibits the action of increasing the amount of the acid generated from the acid generating agent (B) or the like, and achieves the effect of improving "apparent sensitivity" of the radiation-sensitive resin composition.

Examples of the sensitizing agent include carbazoles, acetophenones, benzophenones, naphthalenes, phenols, biacetyl, eosin, rose bengal, pyrenes, anthracenes, phenothiazines, and the like. These sensitizing agents may be used either alone, or two or more types thereof may be used in combination. The upper limit of the content of the sensitizing agent with respect to 100 parts by mass of the polymer (A) is preferably 2 parts by mass, and more preferably 1 part by mass.

Preparation Method of Radiation-Sensitive Resin Composition

The radiation-sensitive resin composition of the embodiment of the present invention may be prepared, for example, by mixing the polymer (A), the acid generator (B) and the compound (C), as well as the polymer (D), the solvent (E) and other optional component(s) which are contained as needed, at a predetermined ratio, and preferably filtering the resulting mixture through a filter having a pore size of about 0.2 μm, for example. The lower limit of the solid content concentration of the radiation-sensitive resin composition is preferably 0.1% by mass, more preferably 0.5 parts by mass, and still more preferably 1% by mass. The upper limit of the aforementioned solid content concentration is preferably 50% by mass, more preferably 30% by mass, and still more preferably 20% by mass.

The radiation-sensitive resin composition of the embodiment of the present invention may be used for formation of positive tone patterns by using an alkaline developer solution, and formation of negative tone patterns by using a developer solution containing an organic solvent. Of these, when used for the formation of negative tone patterns by using the developer solution containing the organic solvent, the radiation-sensitive resin composition may exhibit more superior resolution.

Resist Pattern-Forming Method

The resist pattern-forming method according to another embodiment of the present invention includes: the step of applying on one face side of a substrate the radiation-sensitive resin composition of the embodiment of the invention (hereinafter, may be also referred to as "applying step"); the step of exposing the resist film obtained after the applying (hereinafter, may be also referred to as "exposure step"); and the step of developing the resist film exposed (hereinafter, may be also referred to as "development step").

Since the radiation-sensitive resin composition is used in the resist pattern-forming method, formation of a resist pattern accompanied by less LWR, higher resolution, and fewer defects is enabled, with the superior depth of focus, inhibitory ability of contraction during PEB and storage stability attained. Each step will be described below.

Applying Step

In this step, the radiation-sensitive resin composition is applied on one face side (directly or indirectly on a face) of a substrate. Thus, a resist film is formed. The substrate onto which the radiation-sensitive resin composition is applied is exemplified by a silicon wafer, a wafer coated with aluminum, and the like. The application procedure of the radiation-sensitive resin composition is not particularly limited, and is exemplified by a well-known procedure such as spin coating. When the radiation-sensitive resin composition is applied, the amount of the radiation-sensitive resin composition applied is adjusted such that the resist film formed has a desired thickness. It is to be noted that after the radiation-sensitive resin composition is applied on the substrate, prebaking (hereinafter, may be also referred to as "PB") may be carried out to evaporate the solvent. The lower limit of the temperature of PB is preferably 30° C., and more preferably 50° C. The upper limit of the aforementioned temperature is preferably 200° C., and more preferably 150° C. The lower limit of the time period of PB is preferably 10 sec, and more preferably 30 sec. The upper limit of the time period is preferably 600 sec, and more preferably 300 sec. The lower limit of the average thickness of the resist film is preferably 10 nm, more preferably 20 nm, and still more preferably 50 nm. The upper limit of the aforementioned average thickness is preferably 1,000 nm, more preferably 200 nm, and still more preferably 150 nm.

Exposure Step

In this step, the resist film obtained after the applying is exposed. The exposure may be carried out by irradiation with a radioactive ray through a mask having a predetermined pattern, and through a liquid for liquid immersion lithography such as water, as needed.

A liquid having a refractive index greater than that of air is typically used as the liquid for liquid immersion lithography. Specific examples of such a liquid include pure water, long chain or cyclic aliphatic compounds, and the like. The resist film is irradiated with the radioactive ray emitted from a lithography device through the liquid for liquid immersion lithography, i.e., with a space between a lens and the resist film being filled with the liquid for liquid immersion lithography, whereby the resist film is exposed through a mask having a predetermined pattern.

The radioactive ray employed may be appropriately selected in accordance with the type of the radiation-sensitive acid generator used, from among electromagnetic waves e.g., visible light rays, ultraviolet rays, far ultraviolet rays such as an ArF excimer laser beam (wavelength: 193 nm) and a KrF excimer laser beam (wavelength: 248 nm), extreme ultraviolet rays (EUV; 13.5 nm), X-rays, etc., and charged particle rays such as an electron beam and an α-ray, and the like. Of these, an ArF excimer laser beam, a KrF excimer laser beam, EUV, X-ray and an electron beam are preferred, and an ArF excimer laser beam, EUV and an electron beam are more preferred. It is to be noted that exposure conditions such as an exposure dose may be appropriately selected in accordance with the blend composition of the radiation-sensitive resin composition, the type of an additive, and the like.

The exposed resist film is preferably subjected to a baking treatment (hereinafter, may be also referred to as "post exposure baking (PEB)"). The PEB enables the dissociation reaction of the acid-labile group included in the polymer (A) or the like to smoothly proceed. The baking conditions for the PEB may be appropriately adjusted in accordance with the blend composition of the radiation-sensitive resin composition, and the lower limit of the temperature of PEB is preferably 30° C., more preferably 50° C., and still more preferably 70° C. The upper limit of the aforementioned temperature is preferably 200° C., more preferably 150° C., and still more preferably 120° C. The lower limit of the time period of PEB is preferably 10 sec, and more preferably 30 sec. The upper limit of the time period is preferably 600 sec, and more preferably 300 sec.

In addition, in order to maximally utilize the potential of the radiation-sensitive resin composition, an organic or inorganic antireflective film may also be formed on the substrate employed, as disclosed in, for example, Japanese Examined Patent Application, Publication No. H6-12452, Japanese Unexamined Patent Application, Publication No. S59-93448, and the like. Moreover, in order to avoid the influence of basic impurities and the like contained in an environment atmosphere, a protective film may be provided on the resist film, as disclosed in, for example, Japanese Unexamined Patent Application, Publication No. H5-188598, and the like.

Development Step

In this step, the resist film exposed in the exposure step is developed. The developer solution for use in this development is exemplified by an alkaline aqueous solution (alkaline developer solution), a liquid containing an organic solvent (organic solvent developer solution), and the like. Thus, a predetermined resist pattern is formed.

The alkaline developer solution is exemplified by alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyl dimethyl amine, triethanolamine, tetramethylammonium hydroxide (TMAH), pyrrole, piperidine, choline, 1,8-diazabicyclo-[5.4.0]-7-undecene, 1,5-diazabicyclo-[4.3.0]-5-nonene, etc., and the like. Of these, an aqueous TMAH solution is preferred, and a 2.38% by mass aqueous TMAH solution is more preferred.

The organic solvent developer solution is exemplified by organic solvents such as hydrocarbon solvents, ether solvents, ester solvents, ketone solvents and alcohol solvents, or liquids containing an organic solvent. Examples of the organic solvent include one type, or two or more types of the solvents exemplified in connection with the solvent (E) of the aforementioned radiation-sensitive resin composition, and the like. Of these, the ester solvents and the ketone solvents are preferred. As the ester solvent, acetic acid ester solvents are preferred, and n-butyl acetate is more preferred. As the ketone solvent, chain ketones are preferred, and 2-heptanone is more preferred. The lower limit of the content of the organic solvent in the organic solvent developer solution is preferably 80% by mass, more preferably 90% by mass, still more preferably 95% by mass, and particularly preferably 99% by mass. Components other than the organic solvent in the organic solvent developer solution are exemplified by water, silicone oil, and the like.

These developer solutions may be used either alone, or in combination of two or more types thereof. It is to be noted that washing with water or the like, followed by drying, is generally carried out after the development.

Acid Diffusion Control Agent

The acid diffusion control agent includes a compound capable of forming a salt through a structural change in a molecule thereof upon irradiation with a radioactive ray. Due to having the aforementioned properties, the acid diffusion control agent may be suitably used as a component for the acid diffusion control agent in the radiation-sensitive resin composition, thereby enabling the LWR performance, the resolution, the depth of focus, the inhibitory ability of defects, the inhibitory ability of contraction during PEB and the storage stability of the radiation-sensitive resin composition to be improved. The acid diffusion control agent is as described in the above section of (C) Compound.

EXAMPLES

Hereinafter, the present invention is explained in detail by way of Examples, but the present invention is not in any way limited to these Examples. Measuring methods for various types of physical properties are shown below.

Weight Average Molecular Weight (Mw), Number Average Molecular Weight (Mn) and Dispersity Index (Mw/Mn)

The Mw and the Mn of the polymer were determined by gel permeation chromatography (GPC) by using GPC columns manufactured by Tosoh Corporation ("G2000HXL"×2, "G3000HXL"×1 and "G4000HXL"×1) under the following conditions. Moreover, the dispersity index (Mw/Mn) was calculated from the results of the determination of the Mw and the Mn.

elution solvent: tetrahydrofuran flow rate: 1.0 mL/min sample concentration: 1.0% by mass amount of injected sample: 100 μL column temperature: 40° C.

detector: differential refractometer standard substance: mono-dispersed polystyrene $^1$H-NMR Analysis and $^{13}$C-NMR Analysis In a $^1$H-NMR analysis of the compound and a $^{13}$C-NMR analysis for determining the proportion of each structural unit contained in the polymer, measurements were carried out using a nuclear magnetic resonance apparatus ("JNM-ECX400" available from JEOL, Ltd.), with deutero chloroform as a measurement solvent.

Synthesis of Compound

As the compound (C), compounds represented by the following formulae (C-1) to (C-16) were synthesized.

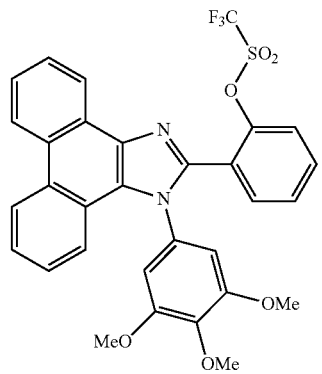

(C-1)

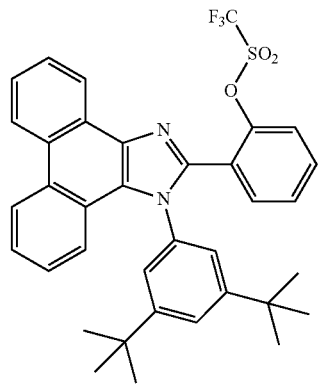

(C-2)

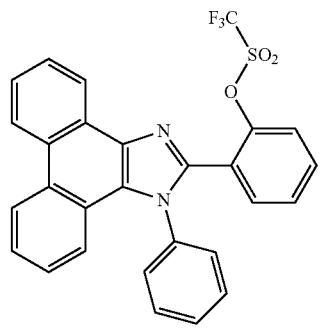

(C-3)

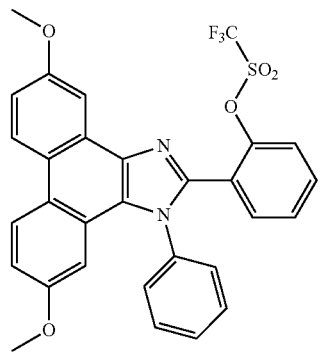

(C-4)

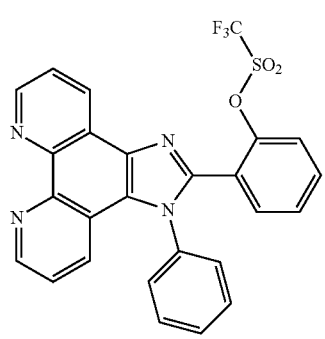 (C-5)
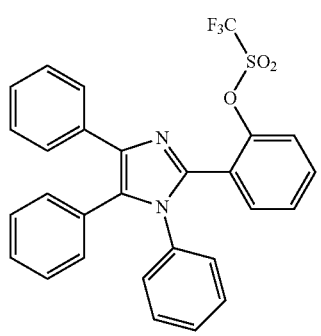 (C-6)
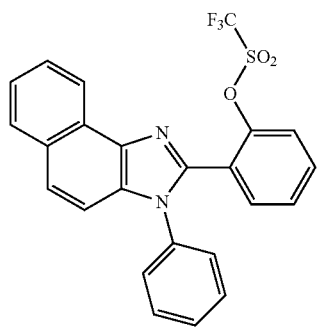 (C-7)
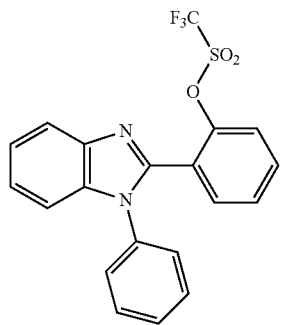 (C-8)
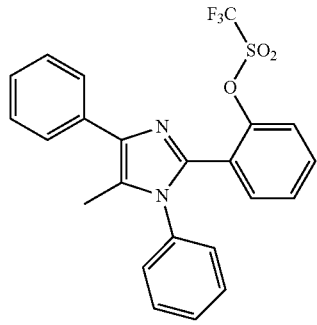 (C-9)
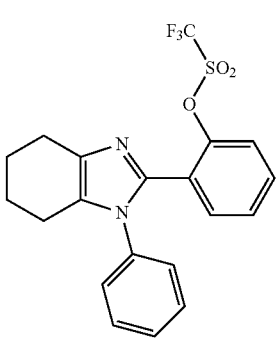 (C-10)
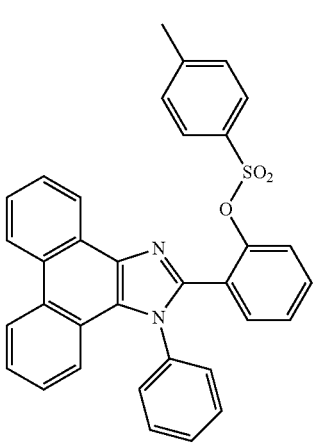 (C-11)
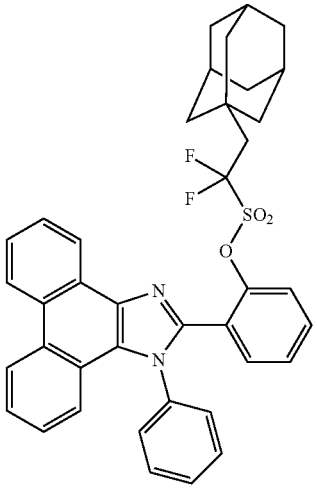 (C-12)
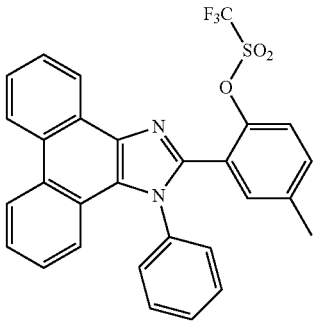 (C-13)

-continued

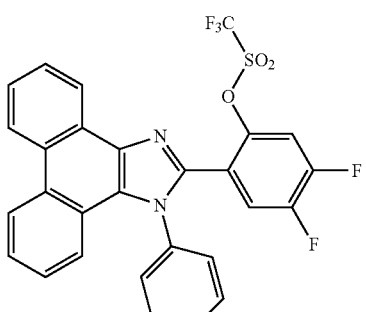
(C-14)

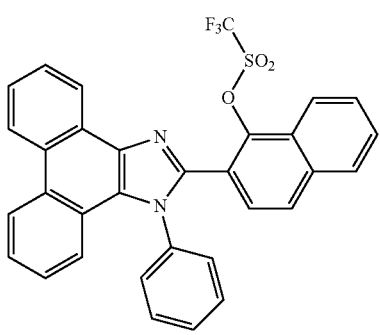
(C-15)

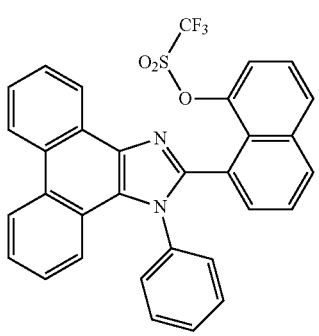
(C-16)

Synthesis Example 1: Synthesis of Compound (C-1)

In a reaction vessel, 2.08 g (10 mol) of 9,10-phenanthrenequinone, 2.75 g (15 mmol) of 3,4,5-trimethoxyaniline, 2.54 g (10 mmol) of 2-trifluoromethanesulfonyloxybenzaldehyde, 3.85 g (50 mmol) of ammonium acetate and 100 mL of acetic acid were charged, and the mixture was heated to 110° C. and stirred for 4 hrs. Next, acetic acid was removed under a reduced pressure condition, and adding 50 mL of ethyl acetate and 50 mL of an aqueous saturated sodium bicarbonate solution thereto and liquid separation followed. The organic layer was dried over anhydrous sodium sulfate and filtered, and the solvent was distilled off. The compound (C-1) was obtained by purification on silica gel column chromatography (amount: 4.43 g; yield: 73%).

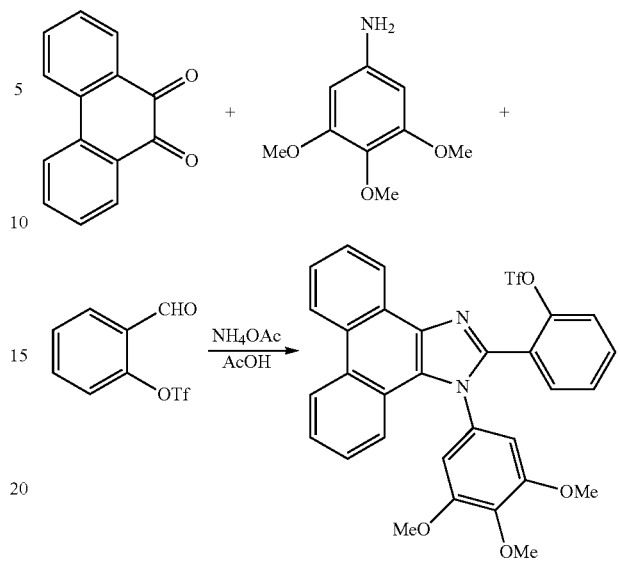

Synthesis Examples 2 to 16: Syntheses of Compounds (C-2) to (C-16)

The compounds (C-2) to (C-16) were synthesized by a similar operation to that of Synthesis Example 1 through appropriately selecting the precursor.

Synthesis of Polymer

Monomers used for the syntheses of the polymer (A) and the polymer (D) are shown below. The compound (M-16) gives a p-hydroxystyrene unit in the polymer.

(M-1)

(M-2)

(M-3)

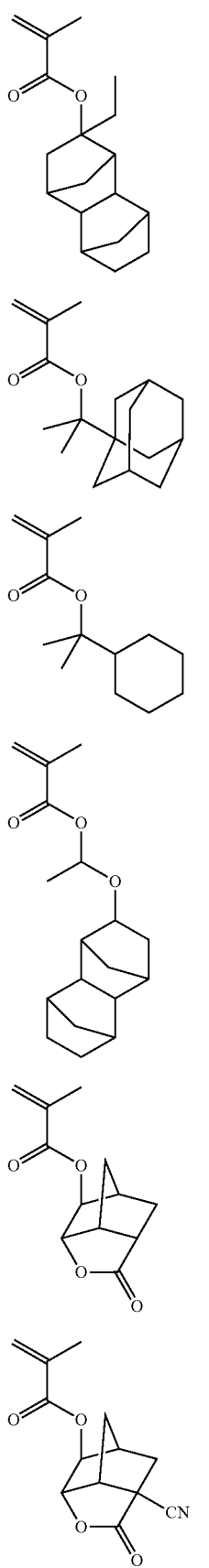
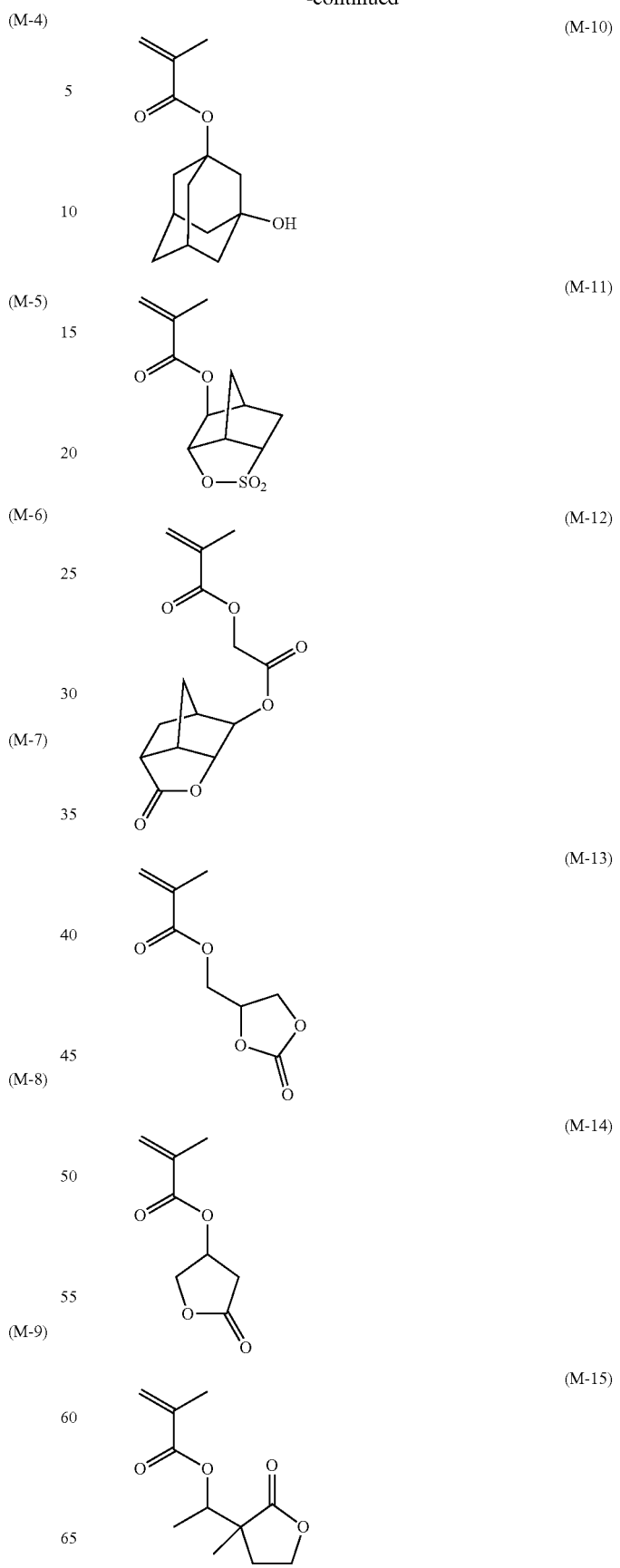

-continued

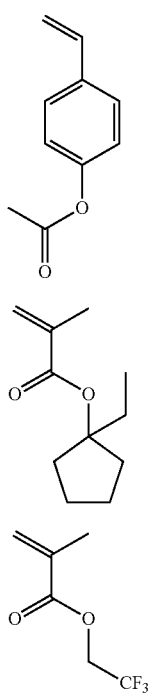

(M-16)

(M-17)

(M-18)

Synthesis of Polymer (A)

Synthesis Example 17: Synthesis of Polymer (A-1)

A monomer solution was prepared by dissolving 7.32 g (40 mol %) of the compound (M-1), 2.32 g (10 mol %) of the compound (M-3) and 10.36 g (50 mol %) of the compound (M-8) in 40 g of 2-butanone, and further dissolving therein 0.766 g (5 mol % with respect to the total monomer) of azobisisobutyronitrile as a radical polymerization initiator. Next, a 200 mL three-neck flask containing 20 g of 2-butanone was heated to 80° C. with stirring in a nitrogen atmosphere, and the monomer solution prepared as described above was added dropwise over 3 hrs. After the completion of the dropwise addition, a polymerization reaction was allowed by further heating at 80° C. for 3 hrs. After the completion of the polymerization reaction, the polymerization reaction mixture was cooled to room temperature, poured into 300 g of methanol, and thus precipitated solid was filtered off. The collected solid was washed twice with 60 mL of methanol, followed by filtration, and then dried at 50° C. for 15 hrs to give a polymer (A-1) (amount: 15.8 g; yield: 78.9%). The polymer (A-1) had the Mw of 6,100, and the Mw/Mn of 1.41. The results of the $^{13}$C-NMR analysis indicated that the proportions of the structural units derived from (M-1), (M-3) and (M-8) were 41.2 mol %, 9.2 mol % and 49.6 mol %, respectively.

Synthesis Examples 18 to 22: Syntheses of Polymers (A-2) to (A-6)

Polymers (A-2) to (A-6) were synthesized by a similar operation to that of Synthesis Example 17 except that the type and the amount of the monomer used were as shown in Table 1 below.

Synthesis Example 23: Synthesis of Polymer (A-7)

After 45.24 g (50 mol %) of the compound (M-16), 54.76 g (50 mol %) of the compound (M-1), 4.58 g (5 mol % with respect to the total monomer) of azobisisobutyronitrile as a radical polymerization initiator, and 1.14 g t-dodecyl mercaptan were dissolved in 100 g of propylene glycol monomethyl ether, the mixture was subjected to polymerization for 16 hrs in a nitrogen atmosphere, while the reaction temperature was maintained at 70° C. After the completion of the polymerization reaction, the polymerization reaction mixture was added dropwise to 1,000 g of n-hexane to permit solidification purification of a polymer. Thereafter, to the resulting solid was added 150 g of propylene glycol monomethyl ether again, and then 150 g of methanol, 34 g of triethylamine and 6 g of water were further added. The mixture was subjected to a hydrolysis reaction for 8 hrs while refluxing at a boiling point was allowed. After the completion of the reaction, the solvent and triethylamine were distilled off in vacuo, the resulting solid was dissolved in 150 g of acetone, which was then added dropwise to 2,000 g of water to permit solidification, and the produced solid was filtered off and was dried at 50° C. for 17 hrs to give a polymer (A-7) as a white powder (amount: 63.8 g; yield: 72.3%). The polymer (A-7) had the Mw of 6,400, and the Mw/Mn of 1.72. The result of $^{13}$C-NMR analysis indicated that the proportions of the p-hydroxystyrene unit and the structural unit derived from (M-1) were 51.2 mol % and 48.8 mol %, respectively.

TABLE 1

| | (A) Polymer | Monomer that gives structural unit (I) | | Monomer that gives structural unit (II) | | Monomer that gives structural unit (III) or (IV) | | | Yield (%) | Mw | Mw/Mn |
| | | type | amount (mol %) | proportion of structural unit (mol %) | type | amount (mol %) | proportion of structural unit (mol %) | type | amount (mol %) | proportion of structural unit (mol %) | | | |
|---|---|---|---|---|---|---|---|---|---|---|---|---|---|
| Synthesis Example 17 | A-1 | M-1 | 40 | 41.2 | M-8 | 50 | 49.6 | — | — | — | 78.9 | 6,100 | 1.41 |
| | | M-3 | 10 | 9.2 | | | | | | | | | |
| Synthesis Example 18 | A-2 | M-2 | 40 | 40.8 | — | — | — | M-10 | 40 | 39.4 | 79.3 | 6,200 | 1.39 |
| | | M-5 | 20 | 19.8 | | | | | | | | | |
| Synthesis Example 19 | A-3 | M-1 | 30 | 30.2 | M-14 | 60 | 59.7 | — | — | — | 82.3 | 6,300 | 1.42 |
| | | M-7 | 10 | 10.1 | | | | | | | | | |
| Synthesis Example 20 | A-4 | M-1 | 40 | 39.7 | M-9 | 30 | 30.4 | — | — | — | 81.2 | 6,200 | 1.43 |
| | | | | | M-13 | 30 | 39.9 | | | | | | |
| Synthesis Example 21 | A-5 | M-6 | 50 | 48.9 | M-11 | 30 | 30.2 | — | — | — | 73.5 | 6,100 | 1.40 |
| | | | | | M-15 | 20 | 30.9 | | | | | | |
| Synthesis Example 22 | A-6 | M-4 | 50 | 48.2 | M-12 | 50 | 51.8 | — | — | — | 70.2 | 6,400 | 1.44 |

TABLE 1-continued

| (A) Polymer | type | Monomer that gives structural unit (I) amount (mol %) | proportion of structural unit (mol %) | type | Monomer that gives structural unit (II) amount (mol %) | proportion of structural unit (mol %) | type | Monomer that gives structural unit (III) or (IV) amount (mol %) | proportion of structural unit (mol %) | Yield (%) | Mw | Mw/Mn |
|---|---|---|---|---|---|---|---|---|---|---|---|---|
| Synthesis Example 23 | A-7 | M-1 | 50 | 51.2 | — | — | — | M-16 | 50 | 48.8 | 72.3 | 6,400 | 1.72 |

Synthesis of Polymer (D)

Synthesis Example 24: Synthesis of Polymer (D-1)

A monomer solution was prepared by dissolving 21.5 g (70 mol %) of the compound (M-17) and 8.5 g (30 mol %) of the compound (M-18) in 20 g of 2-butanone, and further dissolving therein 1.38 g (5 mol % with respect to the total monomer) of azobisisobutyronitrile as a radical polymerization initiator. Next, a 100 mL three-neck flask containing 10 g of 2-butanone was heated to 80° C. with stirring in a nitrogen atmosphere, and the monomer solution prepared as described above was added dropwise over 3 hrs. After the completion of the dropwise addition, a polymerization reaction was allowed by further heating at 80° C. for 3 hrs. After the completion of the polymerization reaction, the polymerization reaction mixture was cooled to room temperature and transferred into a separatory funnel. Thereafter, the reaction mixture was homogeneously diluted in 45 g of n-hexane, and 180 g of methanol was charged thereto and mixed therewith. Next, 9 g of distilled water was added thereto, and the mixture was further stirred and left to stand for 30 min. Subsequently, the underlayer was recovered and the solvent was replaced with propylene glycol monomethyl ether acetate to give a propylene glycol monomethyl ether acetate solution containing a polymer (D-1) being the solid content (yield: 60.0%). The polymer (D-1) had the Mw of 7,200, and the Mw/Mn of 2.00. The results of the $^{13}$C-NMR analysis indicated that the proportions of the structural units derived from (M-17) and (M-18) were 71.1 mol % and 28.9 mol %, respectively.

Preparation of Radiation-Sensitive Resin Composition

The acid generating agent (B), the compound (C) and the solvent (E) which were used in the preparation of the radiation-sensitive resin composition are shown below.

(B) Acid Generating Agent

B-1 to B-9: compounds represented by the following formulae (B-1) to (B-9).

(B-1)

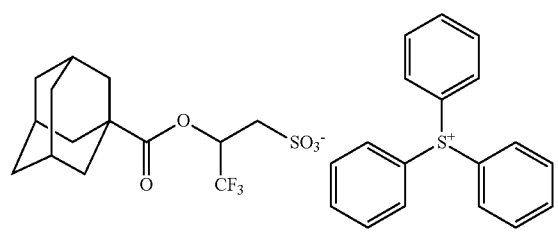

(B-2)

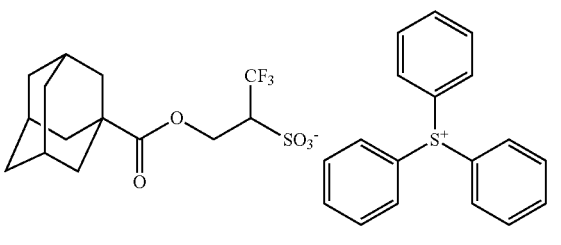

(B-3)

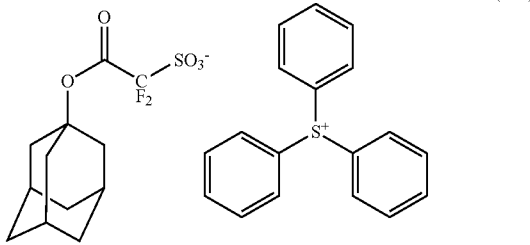

(B-4)

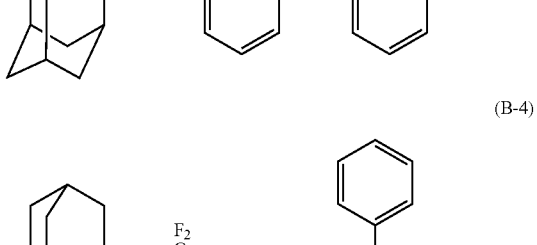

(B-5)

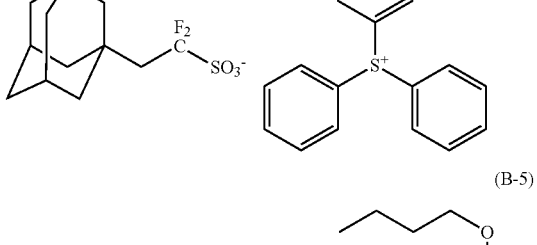

(B-6)

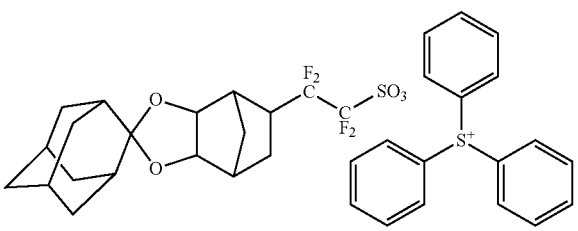

-continued (B-7)
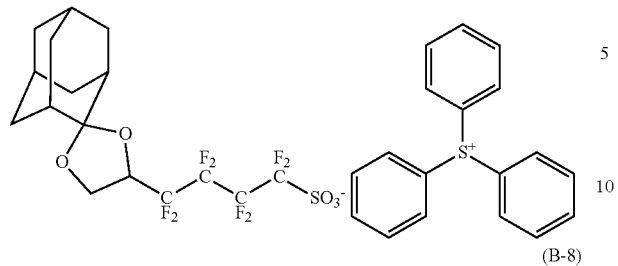

(B-8)
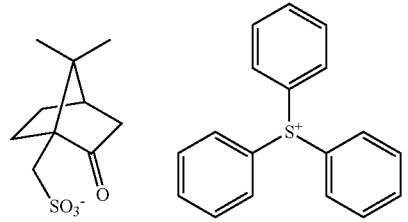

(B-9)
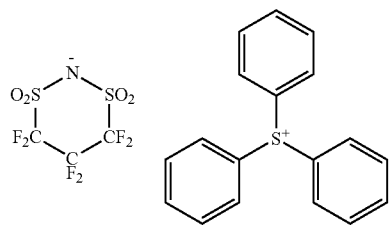

(C) Compound
C-1 to C-16: the compounds (C-1) to (C-16) synthesized as described above.
CC-1 to CC-8: compounds represented by the following formulae (CC-1) to (CC-8).

(CC-1)
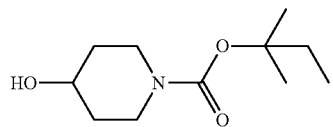

(CC-2)
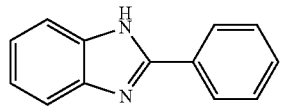

(CC-3)
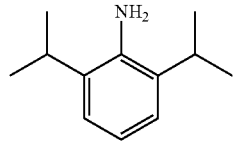

(CC-4)
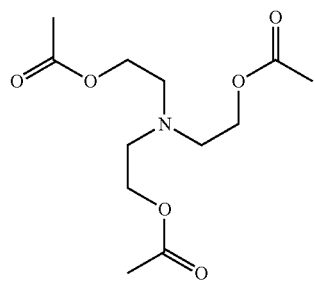

-continued (CC-5)
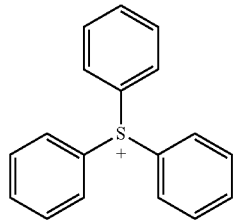

(CC-6)
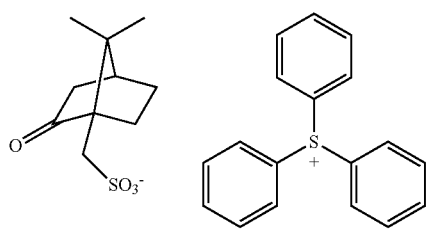

(CC-7), (CC-8)
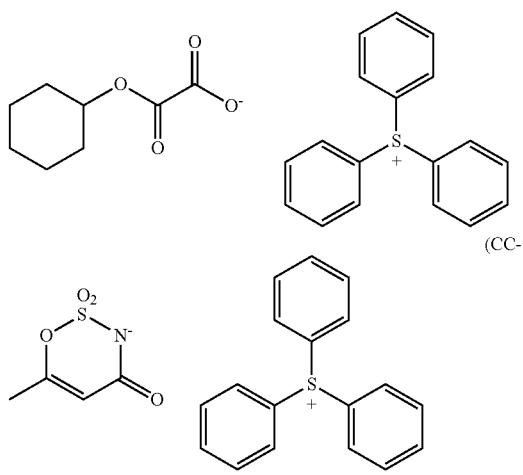

(E) Solvent
E-1: propylene glycol monomethyl ether acetate
E-2: cyclohexanone
E-3: γ-butyrolactone
E-4: ethyl lactate Preparation of Radiation-Sensitive Resin Composition for ArF Exposure Example 1: Preparation of Radiation-Sensitive Resin Composition (J-1)

A radiation-sensitive resin composition (J-1) was prepared by mixing 100 parts by mass of (A-1) as the polymer (A), 7.9 parts by mass of (B-1) as the acid generating agent (B), 1.6 parts by mass of (C-1) as the compound (C), 3.0 parts by mass of (D-1) as the polymer (D), and 2,240 parts by mass of (E-1), 960 parts by mass of (E-2) and 30 parts by mass of (E-3) as the solvent (E), and thereafter filtering the resulting mixed solution through a filter having a pore size of 0.20 μm.

Examples 2 to 27 and Comparative Examples 1 to 8

Radiation-sensitive resin compositions (J-2) to (J-27), and (CJ-1) to (CJ-8) were prepared by a similar operation to that of Example 1 except that the type and the content of each component used were as shown in Table 2 and Table 3 below.

TABLE 2

| Radiation-sensitive resin composition | (A) Polymer type | content (parts by mass) | (B) Acid generating agent type | content (parts by mass) | (C) Compound type | content (parts by mass) | (D) Polymer type | content (parts by mass) | (E) Solvent type | content (parts by mass) |
|---|---|---|---|---|---|---|---|---|---|---|
| Example 1 | J-1 | A-1 | 100 | B-1 | 7.9 | C-1 | 1.6 | D-1 | 3 | E-1/E-2/E-3 | 2,240/960/30 |
| Example 2 | J-2 | A-1 | 100 | B-1 | 15.2 | C-1 | 3.1 | D-1 | 3 | E-1/E-2/E-3 | 2,240/960/30 |
| Example 3 | J-3 | A-1 | 100 | B-1 | 4.8 | C-1 | 1.0 | D-1 | 3 | E-1/E-2/E-3 | 2,240/960/30 |
| Example 4 | J-4 | A-1 | 100 | B-1 | 7.9 | C-2 | 1.6 | D-1 | 3 | E-1/E-2/E-3 | 2,240/960/30 |
| Example 5 | J-5 | A-1 | 100 | B-1 | 7.9 | C-3 | 1.6 | D-1 | 3 | E-1/E-2/E-3 | 2,240/960/30 |
| Example 6 | J-6 | A-1 | 100 | B-1 | 7.9 | C-4 | 1.6 | D-1 | 3 | E-1/E-2/E-3 | 2,240/960/30 |
| Example 7 | J-7 | A-1 | 100 | B-1 | 7.9 | C-5 | 1.6 | D-1 | 3 | E-1/E-2/E-3 | 2,240/960/30 |
| Example 8 | J-8 | A-1 | 100 | B-1 | 7.9 | C-6 | 1.6 | D-1 | 3 | E-1/E-2/E-3 | 2,240/960/30 |
| Example 9 | J-9 | A-1 | 100 | B-1 | 7.9 | C-7 | 1.6 | D-1 | 3 | E-1/E-2/E-3 | 2,240/960/30 |
| Example 10 | J-10 | A-1 | 100 | B-1 | 7.9 | C-8 | 1.6 | D-1 | 3 | E-1/E-2/E-3 | 2,240/960/30 |
| Example 11 | J-11 | A-1 | 100 | B-1 | 7.9 | C-9 | 1.6 | D-1 | 3 | E-1/E-2/E-3 | 2,240/960/30 |
| Example 12 | J-12 | A-1 | 100 | B-1 | 7.9 | C-10 | 1.6 | D-1 | 3 | E-1/E-2/E-3 | 2,240/960/30 |
| Example 13 | J-13 | A-1 | 100 | B-1 | 7.9 | C-11 | 1.6 | D-1 | 3 | E-1/E-2/E-3 | 2,240/960/30 |
| Example 14 | J-14 | A-1 | 100 | B-1 | 7.9 | C-12 | 1.6 | D-1 | 3 | E-1/E-2/E-3 | 2,240/960/30 |
| Example 15 | J-15 | A-1 | 100 | B-1 | 7.9 | C-13 | 1.6 | D-1 | 3 | E-1/E-2/E-3 | 2,240/960/30 |
| Example 16 | J-16 | A-1 | 100 | B-1 | 7.9 | C-14 | 1.6 | D-1 | 3 | E-1/E-2/E-3 | 2,240/960/30 |
| Example 17 | J-17 | A-1 | 100 | B-1 | 7.9 | C-15 | 1.6 | D-1 | 3 | E-1/E-2/E-3 | 2,240/960/30 |
| Example 18 | J-18 | A-1 | 100 | B-1 | 7.9 | C-16 | 1.6 | D-1 | 3 | E-1/E-2/E-3 | 2,240/960/30 |

TABLE 3

| Radiation-sensitive resin composition | (A) Polymer type | content (parts by mass) | (B) Acid generating agent type | content (parts by mass) | (C) Compound type | content (parts by mass) | (D) Polymer type | content (parts by mass) | (E) Solvent type | content (parts by mass) |
|---|---|---|---|---|---|---|---|---|---|---|
| Example 19 | J-19 | A-2 | 100 | B-2 | 7.9 | C-1 | 1.6 | D-1 | 3 | E-1/E-2/E-3 | 2,240/960/30 |
| Example 20 | J-20 | A-6 | 100 | B-3 | 7.9 | C-1 | 1.6 | D-1 | 3 | E-1/E-2/E-3 | 2,240/960/30 |
| Example 21 | J-21 | A-4 | 100 | B-4 | 7.9 | C-1 | 1.6 | D-1 | 3 | E-1/E-2/E-3 | 2,240/960/30 |
| Example 22 | J-22 | A-2 | 100 | B-5 | 7.9 | C-1 | 1.6 | D-1 | 3 | E-1/E-2/E-3 | 2,240/960/30 |
| Example 23 | J-23 | A-4 | 100 | B-6 | 7.9 | C-1 | 1.6 | D-1 | 3 | E-1/E-2/E-3 | 2,240/960/30 |
| Example 24 | J-24 | A-3 | 100 | B-7 | 7.9 | C-1 | 1.6 | D-1 | 3 | E-1/E-2/E-3 | 2,240/960/30 |
| Example 25 | J-25 | A-5 | 100 | B-9 | 7.9 | C-1 | 1.6 | D-1 | 3 | E-1/E-2/E-3 | 2,240/960/30 |
| Example 26 | J-26 | A-7 | 100 | B-7 | 7.9 | C-1/CC-1 | 1.0/0.6 | D-1 | 3 | E-1/E-2/E-3 | 2,240/960/30 |
| Example 27 | J-27 | A-1 | 100 | B-3 | 7.9 | C-1/CC-5 | 1.0/0.6 | D-1 | 3 | E-1/E-2/E-3 | 2,240/960/30 |
| Comparative Example 1 | CJ-1 | A-1 | 100 | B-1 | 7.9 | CC-1 | 1.6 | D-1 | 3 | E-1/E-2/E-3 | 2,240/960/30 |
| Comparative Example 2 | CJ-2 | A-1 | 100 | B-1 | 7.9 | CC-2 | 1.6 | D-1 | 3 | E-1/E-2/E-3 | 2,240/960/30 |
| Comparative Example 3 | CJ-3 | A-1 | 100 | B-1 | 7.9 | CC-3 | 1.6 | D-1 | 3 | E-1/E-2/E-3 | 2,240/960/30 |
| Comparative Example 4 | CJ-4 | A-1 | 100 | B-1 | 7.9 | CC-4 | 1.6 | D-1 | 3 | E-1/E-2/E-3 | 2,240/960/30 |
| Comparative Example 5 | CJ-5 | A-1 | 100 | B-1 | 7.9 | CC-5 | 1.6 | D-1 | 3 | E-1/E-2/E-3 | 2,240/960/30 |
| Comparative Example 6 | CJ-6 | A-1 | 100 | B-1 | 7.9 | CC-6 | 1.6 | D-1 | 3 | E-1/E-2/E-3 | 2,240/960/30 |
| Comparative Example 7 | CJ-7 | A-1 | 100 | B-1 | 7.9 | CC-7 | 1.6 | D-1 | 3 | E-1/E-2/E-3 | 2,240/960/30 |
| Comparative Example 8 | CJ-8 | A-1 | 100 | B-1 | 7.9 | CC-8 | 1.6 | D-1 | 3 | E-1/E-2/E-3 | 2,240/960/30 |

Resist Pattern Formation

Resist Pattern Formation (1)

An underlayer antireflective film having an average thickness of 105 nm was formed on the surface of a 12-inch silicon wafer by applying a composition for underlayer antireflective film formation ("ARC66" available from Brewer Science) on the surface of the 12-inch silicon wafer using a spin-coater ("CLEAN TRACK ACT12" available from Tokyo Electron Limited), and thereafter baking the composition at 205° C. for 60 sec. Each radiation-sensitive resin composition prepared as described above was applied on the underlayer antireflective film using the spin-coater, and subjected to PB at 90° C. for 60 sec. Thereafter, cooling was carried out at 23° C. for 30 sec to form a resist film having an average thickness of 90 nm. Next, the resist film was exposed using an ArF excimer laser Immersion Scanner ("NSR-S610C" available from NIKON) through a 40 nm line-and-space (1L/1S) mask pattern, under optical conditions involving NA of 1.3 and dipole (Sigma: 0.977/0.782). After the exposure, PEB was carried out at 90° C. for 60 sec. Thereafter, a development was carried out with a 2.38% by mass aqueous TMAH solution as an alkaline developer solution, followed by washing with water and drying to form a positive resist pattern. In this resist pattern formation, an exposure dose at which a 1:1 line-and-space pattern with a line width of 40 nm was formed through a mask for a 1:1 line-and-space with a target dimension of 40 nm was defined as "optimum exposure dose".

Resist Pattern Formation (2)

A negative tone resist pattern was formed by a similar operation to that of the Formation of Resist Pattern (1) described above except that: n-butyl acetate was used in place of the aqueous TMAH solution used to execute a development with an organic solvent; and the washing with water was not carried out.

Evaluations

The LWR performance, the resolution, the depth of focus and the inhibitory ability of defects of each radiation-sensitive resin composition were evaluated according to the following methods on each resist pattern formed as described above. In addition, the inhibitory ability of contraction during PEB was also evaluated in cases in which the development with an organic solvent was conducted. Furthermore, the storage stability of each radiation-sensitive resin composition was evaluated. It is to be noted that for a line-width measurement of the resist patterns, a scanning electron microscope ("CG-4100" available from Hitachi High-Technologies Corporation) was used. The results of the evaluations in the case of the development with an organic solvent and in the case of the development with an alkali are shown in Tables 4 and 5, respectively.

LWR Performance

The resist pattern was observed from above by using the scanning electron microscope. The line width was measured at arbitrary points of 50 in total, then a 3 Sigma value was determined from the distribution of the measurements, and the value was defined as "LWR performance". The smaller value indicates a better LWR performance. The LWR performance was evaluated to be: "favorable" in a case where the value of the LWR performance was no greater than 4.9 nm; and "unfavorable" in a case where the value of the LWR performance was greater than 4.9 nm.

Resolution

A dimension of the minimum resist pattern was measured which was resolved at the optimum exposure dose when the mask pattern size for forming the line-and-space (1L/1S) was changed, and the measurement value was defined as "resolution". The smaller value indicates a better resolution. The resolution was evaluated to be: "favorable" in a case where the value of the resolution was no greater than 36 nm; and "unfavorable" in a case where the value of the resolution was greater than 36 nm.

Depth of Focus

On the resist pattern which was resolved at the optimum exposure dose, the dimension of a pattern formed when the focus was shifted along the depth direction was observed, a latitude in the depth direction in which the pattern dimension falls within the range of 90% to 110% of the basis without being accompanied by a bridge and/or residue was determined, and the measurement was defined as "depth of focus". The depth of focus was evaluated to be: "favorable" in a case where the measurement was greater than 50 nm; and "unfavorable" in a case where the measurement was no greater than 50 nm.

Inhibitory Ability of Contraction During PEB

An underlayer antireflective film having an average thickness of 105 nm was formed on the surface of a 12-inch silicon wafer by applying a composition for forming an underlayer antireflective film ("ARC66" manufactured by Brewer Science) on the surface of the 12-inch silicon wafer using a spin-coater ("CLEAN TRACK ACT12" available from Tokyo Electron Limited), and thereafter heating the composition at 205° C. for 60 sec. Each radiation-sensitive resin composition prepared as described above was applied on the underlayer antireflective film using the spin-coater, and subjected to PB at 90° C. for 60 sec. Thereafter, cooling was carried out at 23° C. for 30 sec to form a resist film having an average thickness of 90 nm. Next, the resist film was subjected to overall-exposure at 70 mJ using an ArF excimer laser Immersion Scanner ("NSR-S610C" available from NIKON), and then the film thickness was measured to determine a film thickness A. Subsequently, PEB was carried out at 90° C. for 60 sec, and thereafter the film thickness was measured again to determine a film thickness B. From the values of the film thickness A and the film thickness B, $[100\times(A-B)/A\,(\%)]$ was calculated, which was defined as "inhibitory ability of contraction during PEB". The smaller value indicates a better inhibitory ability of contraction during PEB. The inhibitory ability of contraction during PEB was evaluated to be: "favorable" in a case where the value was no greater than 14%; and "unfavorable" in a case where the value was greater than 14%.

Storage Stability

The radiation-sensitive resin composition immediately after the preparation, and the same after three-months storage at 25° C. subsequent to the preparation were examined on respective exposure doses at which the pattern formed through a 40-nm 1:1 line-and-space mask resulted in formation of the 1:1 line-and-space with a width of 40 nm. These optimum exposure doses were designated as Ea and Eb, respectively, and $[(Ea-Eb)\times100/Ea]$ was determined as a marker of the storage stability. The storage stability may be evaluated to be: "favorable" in the case resulting in $-1.00\leq[(Ea-Eb)\times100/Ea]\leq1.00$; and "unfavorable" in the case resulting in $[(Ea-Eb)\times100/Ea]<-1.00$ or $1.00<[(Ea-Eb)\times100/Ea]$.

Inhibitory Ability of Defects

On the resist pattern resolved at the optimum exposure dose, the number of defects was counted by using a defect inspection apparatus (KLA-Tencor Corporation, "KLA2810"). A more favorable inhibitory ability of defects is indicated as the number of defects per unit area is smaller. The inhibitory ability of defects may be evaluated to be: "favorable" in the case resulting in no more than 0.2 defects/cm$^2$; and "unfavorable" in the case resulting in more than 0.2 defects/cm$^2$.

TABLE 4

| | Radiation-sensitive resin composition | Development with organic solvent | | | | | |
|---|---|---|---|---|---|---|---|
| | | LWR performance (nm) | resolution (nm) | depth of focus (nm) | inhibitory ability of contraction during PEB (%) | storage stability (%) | inhibitory ability of defects (defects/cm$^2$) |
| Example 1 | J-1 | 4.63 | 34 | 100 | 11.2 | 0.53 | <0.1 |
| Example 2 | J-2 | 4.39 | 34 | 100 | 13.2 | 0.44 | <0.1 |
| Example 3 | J-3 | 4.42 | 34 | 90 | 10.0 | 0.78 | <0.1 |
| Example 4 | J-4 | 4.65 | 33 | 80 | 11.4 | 0.37 | <0.1 |

TABLE 4-continued

| | Radiation-sensitive resin composition | Development with organic solvent ||||||
| | | LWR performance (nm) | resolution (nm) | depth of focus (nm) | inhibitory ability of contraction during PEB (%) | storage stability (%) | inhibitory ability of defects (defects/cm$^2$) |
|---|---|---|---|---|---|---|---|
| Example 5 | J-5 | 4.82 | 35 | 70 | 9.8 | −0.36 | <0.1 |
| Example 6 | J-6 | 4.21 | 34 | 80 | 7.4 | 0.64 | <0.1 |
| Example 7 | J-7 | 4.80 | 35 | 70 | 12.7 | −0.08 | <0.1 |
| Example 8 | J-8 | 4.45 | 33 | 80 | 13.2 | −0.38 | <0.1 |
| Example 9 | J-9 | 4.53 | 35 | 90 | 9.4 | 0.49 | <0.1 |
| Example 10 | J-10 | 4.34 | 34 | 80 | 12.8 | −0.55 | <0.1 |
| Example 11 | J-11 | 4.57 | 35 | 80 | 12.5 | −0.42 | <0.1 |
| Example 12 | J-12 | 4.34 | 35 | 100 | 11.6 | 0.44 | <0.1 |
| Example 13 | J-13 | 4.38 | 35 | 90 | 10.7 | 0.60 | <0.1 |
| Example 14 | J-14 | 4.31 | 35 | 80 | 11.3 | 0.32 | <0.1 |
| Example 15 | J-15 | 4.34 | 33 | 90 | 11.6 | −0.57 | <0.1 |
| Example 16 | J-16 | 4.54 | 34 | 90 | 10.3 | 0.83 | <0.1 |
| Example 17 | J-17 | 4.40 | 33 | 100 | 10.4 | −0.48 | <0.1 |
| Example 18 | J-18 | 4.20 | 33 | 80 | 9.3 | 0.23 | <0.1 |
| Example 19 | J-19 | 4.57 | 34 | 80 | 10.7 | −0.44 | <0.1 |
| Example 20 | J-20 | 4.34 | 33 | 80 | 9.8 | 0.57 | <0.1 |
| Example 21 | J-21 | 4.20 | 35 | 100 | 11.2 | −0.68 | <0.1 |
| Example 22 | J-22 | 4.33 | 35 | 100 | 12.9 | −0.92 | <0.1 |
| Example 23 | J-23 | 4.20 | 32 | 80 | 10.3 | 0.56 | <0.1 |
| Example 24 | J-24 | 4.22 | 33 | 70 | 9.2 | 0.35 | <0.1 |
| Example 25 | J-25 | 3.98 | 33 | 90 | 11.5 | 0.24 | <0.1 |
| Example 26 | J-26 | 4.53 | 32 | 80 | 11.0 | −0.22 | <0.1 |
| Example 27 | J-27 | 4.33 | 34 | 90 | 10.9 | −0.43 | <0.1 |
| Comparative Example 1 | CJ-1 | 5.34 | 38 | 30 | 15.2 | 1.31 | 2.1 |
| Comparative Example 2 | CJ-2 | 5.12 | 39 | 40 | 16.3 | 1.58 | 1.5 |
| Comparative Example 3 | CJ-3 | 5.22 | 38 | 40 | 15.5 | 4.23 | 2.0 |
| Comparative Example 4 | CJ-4 | 6.32 | 37 | 30 | 15.0 | 5.67 | 1.3 |
| Comparative Example 5 | CJ-5 | 5.36 | 39 | 40 | 16.2 | 3.86 | 4.6 |
| Comparative Example 6 | CJ-6 | 5.95 | 38 | 40 | 16.3 | 1.32 | 2.2 |
| Comparative Example 7 | CJ-7 | 7.22 | 39 | 30 | 15.9 | 3.44 | 3.2 |
| Comparative Example 8 | CJ-8 | 5.08 | 37 | 40 | 15.6 | 2.53 | 0.8 |

TABLE 5

| | Radiation-sensitive resin composition | Development with alkali |||||
| | | LWR performance (nm) | resolution (nm) | depth of focus (nm) | storage stability (%) | inhibitory ability of defects (defects/cm$^2$) |
|---|---|---|---|---|---|---|
| Example 1 | J-1 | 4.74 | 34 | 100 | −0.48 | <0.1 |
| Example 2 | J-2 | 4.55 | 35 | 90 | −0.54 | <0.1 |
| Example 3 | J-3 | 4.58 | 34 | 90 | −0.78 | <0.1 |
| Example 4 | J-4 | 4.42 | 34 | 70 | −0.95 | <0.1 |
| Example 5 | J-5 | 4.86 | 35 | 70 | 0.79 | <0.1 |
| Example 6 | J-6 | 4.38 | 36 | 90 | −0.89 | <0.1 |
| Example 7 | J-7 | 4.79 | 35 | 70 | −0.01 | <0.1 |
| Example 8 | J-8 | 4.54 | 35 | 80 | 0.47 | <0.1 |
| Example 9 | J-9 | 4.35 | 33 | 90 | −0.66 | <0.1 |
| Example 10 | J-10 | 4.67 | 35 | 80 | 0.70 | <0.1 |
| Example 11 | J-11 | 4.37 | 35 | 80 | 0.60 | <0.1 |
| Example 12 | J-12 | 4.40 | 34 | 100 | −0.74 | <0.1 |
| Example 13 | J-13 | 4.50 | 35 | 90 | −0.86 | <0.1 |
| Example 14 | J-14 | 4.37 | 34 | 90 | −0.55 | <0.1 |
| Example 15 | J-15 | 4.47 | 34 | 100 | 0.68 | <0.1 |
| Example 16 | J-16 | 4.65 | 32 | 80 | −0.66 | <0.1 |
| Example 17 | J-17 | 4.32 | 33 | 100 | 0.56 | <0.1 |
| Example 18 | J-18 | 4.52 | 35 | 90 | 0.78 | <0.1 |
| Example 19 | J-19 | 4.43 | 34 | 90 | −0.69 | <0.1 |
| Example 20 | J-20 | 4.37 | 36 | 80 | 0.72 | <0.1 |
| Example 21 | J-21 | 4.54 | 35 | 90 | 0.77 | <0.1 |
| Example 22 | J-22 | 4.22 | 32 | 70 | 0.74 | <0.1 |
| Example 23 | J-23 | 4.53 | 33 | 80 | −0.22 | <0.1 |

TABLE 5-continued

|  | Radiation-sensitive resin composition | Development with alkali | | | | |
|---|---|---|---|---|---|---|
|  |  | LWR performance (nm) | resolution (nm) | depth of focus (nm) | storage stability (%) | inhibitory ability of defects (defects/cm²) |
| Example 24 | J-24 | 4.13 | 34 | 90 | −0.22 | <0.1 |
| Example 25 | J-25 | 3.87 | 33 | 90 | −0.64 | <0.1 |
| Example 26 | J-26 | 4.30 | 33 | 70 | 0.52 | <0.1 |
| Example 27 | J-27 | 4.40 | 34 | 90 | 0.47 | <0.1 |
| Comparative Example 1 | CJ-1 | 5.14 | 37 | 40 | 2.80 | 0.8 |
| Comparative Example 2 | CJ-2 | 5.25 | 38 | 50 | 3.22 | 2.3 |
| Comparative Example 3 | CJ-3 | 5.25 | 37 | 40 | 6.23 | 0.9 |
| Comparative Example 4 | CJ-4 | 5.78 | 38 | 40 | 7.20 | 3.0 |
| Comparative Example 5 | CJ-5 | 6.26 | 37 | 30 | 4.23 | 1.9 |
| Comparative Example 6 | CJ-6 | 7.22 | 37 | 50 | 1.45 | 1.4 |
| Comparative Example 7 | CJ-7 | 5.78 | 39 | 40 | 2.45 | 0.7 |
| Comparative Example 8 | CJ-8 | 4.92 | 37 | 40 | 1.56 | 0.4 |

Preparation of Radiation-Sensitive Resin Composition for Electron Beam Exposure

Example 28: Preparation of Radiation-Sensitive Resin Composition (J-28)

A radiation-sensitive resin composition (J-28) was prepared by mixing 100 parts by mass of (A-7) as the polymer (A), 20 parts by mass of (B-7) as the acid generating agent (B), 2.5 parts by mass of (C-5) as the compound (C), and 4,280 parts by mass of (E-1) and 1,830 parts by mass of (E-2) as the solvent (E), and thereafter filtering the resulting mixture through a membrane filter having a pore size of 0.2 µm.

Examples 29 to 32 and Comparative Examples 9 and 10

Radiation-sensitive resin compositions (J-28) to (J-31), and (CJ-9) and (CJ-10) were prepared by a similar operation to that of Example 28 except that the type and the content of each component used were as shown in Table 6 below.

TABLE 6

|  | Radiation-sensitive resin composition | (A) Polymer | | (B) Acid generating agent | | (C) Compound | | (E) Solvent | |
|---|---|---|---|---|---|---|---|---|---|
|  |  | type | content (parts by mass) | type | content (parts by mass) | type | content (parts by mass) | type | content (parts by mass) |
| Example 28 | J-28 | A-7 | 100 | B-7 | 20 | C-5 | 2.5 | E-1/E-2 | 4,280/1,830 |
| Example 29 | J-29 | A-7 | 100 | B-8 | 20 | C-9 | 2.5 | E-1/E-2 | 4,280/1,830 |
| Example 30 | J-30 | A-1 | 100 | B-2 | 20 | C-14 | 2.5 | E-1/E-2 | 4,280/1,830 |
| Example 31 | J-31 | A-4 | 100 | B-7 | 20 | C-16 | 2.5 | E-1/E-2 | 4,280/1,830 |
| Comparative Example 9 | CJ-9 | A-7 | 100 | B-8 | 20 | CC-1 | 3.2 | E-1/E-2 | 4,280/1,830 |
| Comparative Example 10 | CJ-10 | A-4 | 100 | B-7 | 20 | CC-4 | 3.2 | E-1/E-2 | 4,280/1,830 |

Resist Pattern Formation (3)

The radiation-sensitive resin composition prepared as described above was applied onto the surface of an 8-inch silicon wafer by using a spin coater (Tokyo Electron Limited, "CLEAN TRACK ACTS"), and then subjected to PB at 90° C. for 60 sec. Thereafter, the silicon wafer was cooled at 23° C. for 30 sec to form a resist film having an average thickness of 50 nm. Next, this resist film was irradiated with an electron beam by using a simplified electron beam writer (Hitachi, Ltd., "HL800D", output: 50 KeV, electric current density: 5.0 A/cm²). After the irradiation, PEB was carried out at 120° C. for 60 sec. The resist film was then developed by using a 2.38% by mass aqueous TMAH solution as an alkaline developer solution at 23° C. for 30 sec, followed by washing with water and drying to form a positive-tone 1:1 line-and-space pattern with a line width of 100 nm.

Resist Pattern Formation (4)

A negative tone resist pattern was formed by a similar operation to that of the Formation of Resist Pattern (3) described above except that: n-butyl acetate was used in place of the aqueous TMAH solution used to execute a development with an organic solvent; and the washing with water was not carried out.

Evaluations

The LWR performance, the resolution, the depth of focus, the inhibitory ability of defects and the inhibitory ability of contraction during PEB were evaluated according to the procedures similar to those for the case of the ArF exposure described above, on the resist pattern formed through the electron beam exposure. In addition, the storage stability of the radiation-sensitive resin composition was evaluated. The results of the evaluations are shown in Table 7 below.

was exposed to KrF excimer laser (wavelength: 248 nm) by using a KrF excimer laser irradiation scanner ("NSR-S203B" available from NIKON) through a mask pattern with varying exposure doses, and thereafter PEB was carried out at 110° C. for 90 sec. The resist film was then developed

TABLE 7

| | Radiation-sensitive resin composition | Development with organic solvent | | | | | Development with alkali | | | | |
|---|---|---|---|---|---|---|---|---|---|---|---|
| | | LWR performance (nm) | resolution (nm) | depth of focus (nm) | inhibitory ability of contraction during PEB (%) | storage stability (%) | inhibitory ability of defects (defects/cm$^2$) | LWR performance (nm) | resolution (nm) | depth of focus (nm) | storage stability (%) | inhibitory ability of defects (defects/cm$^2$) |
| Example 28 | J-28 | 4.23 | 34 | 100 | 12.3 | 0.22 | <0.1 | 4.32 | 34 | 100 | −0.48 | <0.1 |
| Example 29 | J-29 | 3.89 | 34 | 90 | 11.5 | 0.78 | <0.1 | 4.18 | 33 | 90 | 0.32 | <0.1 |
| Example 30 | J-30 | 4.13 | 32 | 80 | 9.5 | −0.45 | <0.1 | 4.22 | 34 | 80 | 0.57 | <0.1 |
| Example 31 | J-31 | 4.76 | 33 | 90 | 11.3 | 0.53 | <0.1 | 4.56 | 34 | 70 | −0.35 | <0.1 |
| Comparative Example 9 | CJ-9 | 5.64 | 39 | 40 | 18.5 | −1.56 | 2.45 | 5.78 | 38 | 30 | 0.79 | 3.15 |
| Comparative Example 10 | CJ-10 | 6.22 | 38 | 30 | 19.0 | −2.55 | 3.12 | 6.14 | 39 | 40 | −0.89 | 3.45 |

Preparation of Radiation-Sensitive Resin Composition for KrF Exposure Example 32

A radiation-sensitive resin composition (J-32) was prepared by mixing 100 parts by mass of (A-7) as the polymer (A), 10 parts by mass of (B-7) as the acid generating agent (B), 0.8 parts by mass of (C-1) as the compound (C), and 180 parts by mass of (E-1) and 430 parts by mass of the solvent (E-4) as the solvent (E), and thereafter filtering the resulting mixture through a membrane filter having a pore size of 0.2 μm.

Examples 33 to 35, and Comparative Examples 11 and 12

Radiation-sensitive resin compositions (J-33) to (J-35), and (CJ-11) and (CJ-12) were prepared by a similar operation to that of Example 32 except that the type and the content of each component used were as shown in Table 8 below.

TABLE 8

| | Radiation-sensitive resin composition | (A) Polymer | | (B) Acid generating agent | | (C) Compound | | (E) Solvent | |
|---|---|---|---|---|---|---|---|---|---|
| | | type | content (parts by mass) | type | content (parts by mass) | type | content (parts by mass) | type | content (parts by mass) |
| Example 32 | J-32 | A-7 | 100 | B-7 | 10 | C-1 | 0.8 | E-1/E-4 | 180/430 |
| Example 33 | J-33 | A-7 | 100 | B-8 | 10 | C-3 | 0.8 | E-1/E-4 | 180/430 |
| Example 34 | J-34 | A-1 | 100 | B-1 | 10 | C-10 | 0.8 | E-1/E-4 | 180/430 |
| Example 35 | J-35 | A-4 | 100 | B-6 | 10 | C-12 | 0.8 | E-1/E-4 | 180/430 |
| Comparative Example 11 | CJ-11 | A-7 | 100 | B-8 | 10 | CC-1 | 0.8 | E-1/E-4 | 180/430 |
| Comparative Example 12 | CJ-12 | A-4 | 100 | B-6 | 10 | CC-4 | 0.8 | E-1/E-4 | 180/430 |

Resist Pattern Formation (5)

After each radiation-sensitive resin composition prepared as described above was spin-coated on a silicon wafer, PB was carried out at 110° C. for 90 sec to form a resist film having an average thickness of 0.3 μm. Next, the resist film by using a 2.38% by mass aqueous TMAH solution as an alkaline developer solution at 23° C. for 60 sec, followed by washing with water for 30 sec and drying to form a positive-tone 1:1 line-and-space pattern with a line width of 180 nm.

Resist Pattern Formation (6)

A negative tone resist pattern was formed by a similar operation to that of the Formation of Resist Pattern (5) described above except that: n-butyl acetate was used in place of the aqueous TMAH solution used to execute a development with an organic solvent; and the washing with water was not carried out.

Evaluations

The LWR performance, the resolution, the depth of focus, the inhibitory ability of defects and the inhibitory ability of contraction during PEB were evaluated according to the procedures similar to those for the case of the ArF exposure described above, on the resist pattern formed through the KrF exposure. In addition, the storage stability of the radiation-sensitive resin composition was evaluated. The results of the evaluations are shown in Table 9 below. It is to be noted that in the case of the KrF exposure, the resolution was evaluated to be: "favorable" in a case where the value of the resolution was no greater than 100 nm; and "unfavorable" in a case where the value of the resolution was greater than 100 nm.

TABLE 9

| | Radiation-sensitive resin composition | Development with organic solvent | | | | | | Development with alkali | | | | |
|---|---|---|---|---|---|---|---|---|---|---|---|---|
| | | LWR performance (nm) | resolution (nm) | depth of focus (nm) | inhibitory ability of contraction during PEB (%) | storage stability (%) | inhibitory ability of defects (defects/cm²) | LWR performance (nm) | resolution (nm) | depth of focus (nm) | storage stability (%) | inhibitory ability of defects (defects/cm²) |
| Example 32 | J-32 | 4.23 | 95 | 110 | 10.3 | 0.55 | <0.1 | 4.74 | 97 | 100 | −0.43 | <0.1 |
| Example 33 | J-33 | 4.55 | 89 | 90 | 12.9 | 0.32 | <0.1 | 4.55 | 98 | 90 | −0.59 | <0.1 |
| Example 34 | J-34 | 4.13 | 88 | 70 | 9.7 | −0.89 | <0.1 | 4.58 | 87 | 90 | −0.87 | <0.1 |
| Example 35 | J-35 | 4.29 | 92 | 90 | 11.3 | 0.38 | <0.1 | 4.42 | 92 | 70 | −0.40 | <0.1 |
| Comparative Example 11 | CJ-11 | 6.78 | 110 | 30 | 18.9 | −1.90 | 2.5 | 4.86 | 105 | 40 | 3.50 | 3.2 |
| Comparative Example 12 | CJ-12 | 7.90 | 109 | 40 | 16.0 | 3.28 | 4.6 | 4.38 | 113 | 40 | −3.11 | 2.4 |

As is clear from the results shown in Table 4, Table 5, Table 7 and Table 9, the radiation-sensitive resin compositions of Examples were superior in the LWR performance, the resolution, the depth of focus, the storage stability and the inhibitory ability of defects in every case of the ArF exposure, the electron beam exposure and the KrF exposure, for both the development with an alkali and the development with an organic solvent. In addition, the inhibitory ability of contraction during PEB was superior for the development with an organic solvent. In Comparative Examples, each of these characteristics was inferior as compared with those of Examples. In general, an electron beam exposure is known to exhibit a similar tendency to the case of an EUV exposure, and therefore, the radiation-sensitive resin compositions of Examples are inferred to be superior in the LWR performances, etc., also in the case of the EUV exposure.

The radiation-sensitive resin composition and the resist pattern-forming method of the embodiments of the present invention enable formation of a resist pattern accompanied by less LWR, higher resolution, and fewer defects is enabled, with the superior depth of focus, inhibitory ability of contraction during PEB and storage stability attained. The acid diffusion control agent of the embodiment of the present invention can be suitably used as an acid diffusion control agent component of the radiation-sensitive resin composition. Therefore, these can be suitably used for pattern formation in in manufacture of semiconductor devices and the like in which further progress of miniaturization is expected.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
a first polymer comprising a first structural unit that comprises an acid-labile group;
a radiation-sensitive acid generator; and
a first compound capable of forming a salt through a structural change in a molecule thereof upon irradiation with a radioactive ray, wherein the first compound is not a salt and represented by formula (1):

(1)

wherein, in the formula (1),
Ar¹ represents a substituted or unsubstituted heteroarenediyl group having 4 to 30 ring atoms and having at least one nitrogen atom as a ring-constituting atom;

Ar² represents a substituted or unsubstituted aryl group having 6 to 30 ring atoms, at least one ring atom of the aryl group being a carbon atom having a hydrogen atom bound thereto, or a substituted or unsubstituted heteroaryl group having 4 to 30 ring atoms, at least one ring atom of the heteroaryl group being a carbon atom having a hydrogen atombound thereto;
Ar³ represents an aryl group having 6 to 30 ring atoms, the aryl group being unsubstituted except that one of the ring atoms of the aryl group is a carbon atom having a single leaving group bound thereto, wherein the leaving group leaves upon irradiation with a radioactive ray to generate an acid, or a heteroaryl group having 4 to 30 ring atoms, the heteroaryl group being unsubstituted except that one of the ring atoms of the heteroaryl group is a carbon atom having a single leaving group bound thereto, wherein the leaving group leaves upon irradiation with a radioactive ray to generate an acid,
wherein number of covalent bonds constituting a shortest bond path between the carbon atom to which the hydrogen atom bonds in Ar² the carbon atom to which the leaving group bonds in Ar³ is no less than 4 and no greater than 7.

2. The radiation-sensitive resin composition according to claim 1, wherein basicity of the first compound changes upon irradiation with a radioactive ray.

3. A radiation-sensitive resin composition comprising:
a first polymer comprising a first structural unit that comprises an acid-labile group;
a radiation-sensitive acid generator; and
a first compound capable of forming a salt through a structural change in a molecule thereof upon irradiation with a radioactive ray, wherein the first compound is not a salt and is represented by formula (1-1):

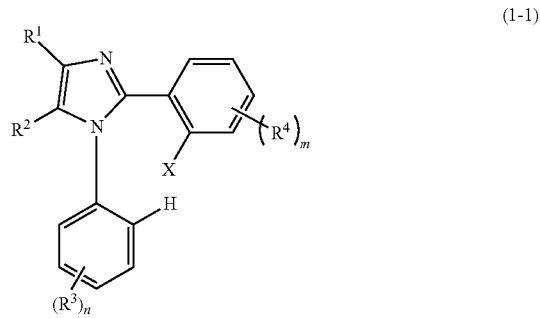

(1-1)

wherein, in the formula (1-1),
R¹ and R² each independently represent a hydrogen atom or a monovalent organic group having 1 to 20 carbon atoms, or $R^1$ and $R^2$ taken together represent a ring structure having 4 to 20 ring atoms together with the carbon atom to which $R^1$ and $R^2$ bond;

$R^3$ represents a monovalent organic group having 1 to 20 carbon atoms; n is an integer of 0 to 4, wherein in a case in which n is no less than 2, a plurality of $R^3$s are identical or different, and the plurality of $R^3$s optionally taken together represent a ring structure having 4 to 20 ring atoms together with the carbon chain to the which the plurality of $R^3$s bond;

$R^4$ represents a monovalent organic group having 1 to 20 carbon atoms other than a leaving group, the leaving group leaving upon irradiation with a radioactive ray to generate an acid, m is an integer of 0 to 4, wherein in a case in which m is no less than 2, a plurality of $R^4$s are identical or different, and the plurality of $R^4$s optionally taken together represent a ring structure having 4 to 20 ring atoms together with the carbon chain to which the plurality of $R^4$s bond; and X represents a monovalent leaving group, the monovalent leaving group leaving upon irradiation with a radioactive ray to generate an acid.

4. The radiation-sensitive resin composition according to claim 1, wherein the first structural unit is a structural unit represented by formula (2), a structural unit that comprises an acetal structure or a combination thereof,

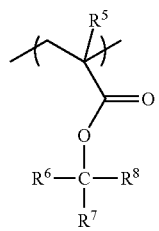

(2)

wherein, in the formula (2), $R^5$ represents a hydrogen atom, a fluorine atom, a methyl group or a trifluoromethyl group; $R^6$ represents a monovalent hydrocarbon group having 1 to 20 carbon atoms; and $R^7$ and $R^8$ each independently represent a monovalent hydrocarbon group having 1 to 20 carbon atoms, or $R^7$ and $R^8$ taken together represent an alicyclic structure having 3 to 20 ring atoms together with the carbon atom to which $R^7$ and $R^8$ bond.

5. A resist pattern-forming method comprising:
applying the radiation-sensitive resin composition according to claim 1 on one face side of a substrate;
exposing the resist film obtained after the applying; and
developing the resist film exposed.

6. The radiation-sensitive resin composition according to claim 5, wherein the monovalent leaving group is a group obtained by removing an acidic hydrogen atom from a hydrohalogenic acid or from a sulfonic acid.

7. The resist pattern-forming method according to claim 5, wherein basicity of the first compound changes upon irradiation with a radioactive ray.

8. The resist pattern-forming method according to claim 5, wherein the first structural unit is a structural unit represented by formula (2), a structural unit that comprises an acetal structure or a combination thereof,

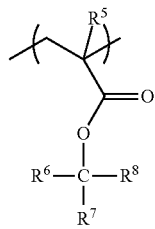

(2)

wherein, in the formula (2), $R^5$ represents a hydrogen atom, a fluorine atom, a methyl group or a trifluoromethyl group; $R^6$ represents a monovalent hydrocarbon group having 1 to 20 carbon atoms; and $R^7$ and $R^8$ each independently represent a monovalent hydrocarbon group having 1 to 20 carbon atoms, or $R^7$ and $R^8$ taken together represent an alicyclic structure having 3 to 20 ring atoms together with the carbon atom to which $R^7$ and $R^8$ bond.

9. The radiation-sensitive resin composition according to claim 1, wherein the leaving group is a group obtained by removing an acidic hydrogen atom from a hydrohalogenic acid or from a sulfonic acid.

10. The radiation-sensitive resin composition according to claim 1, wherein the leaving group is a group obtained by removing an acidic hydrogen atom from a hydrohalogenic acid or from trifluoromethanesulfonic acid.

11. The radiation-sensitive resin composition according to claim 1, wherein in the formula (1), in the definition of Ar', the heteroarenediyl group is unsubstituted or substituted with a methyl group, tert-butyl group, a fluorine atom, or a cyano group; and in the definition of $Ar^2$, the aryl group and the heteroaryl group are each independently unsubstituted or substituted with a hydrogen atom, a halogen atom, a hydroxy group, a nitro group, an amino group, a fluorinated alkyl group, or an alkyl group.

12. The radiation-sensitive resin composition according to claim 5, wherein basicity of the first compound changes upon irradiation with a radioactive ray.

13. The radiation-sensitive resin composition according to claim 5, wherein the first structural unit is a structural unit represented by formula (2), a structural unit that comprises an acetal structure or a combination thereof,

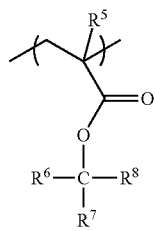

(2)

wherein, in the formula (2), $R^5$ represents a hydrogen atom, a fluorine atom, a methyl group or a trifluoromethyl group; $R^6$ represents a monovalent hydrocarbon group having 1 to 20 carbon atoms; and $R^7$ and $R^8$ each independently represent a monovalent hydrocarbon group having 1 to 20 carbon atoms, or $R^7$ and $R^8$ taken together represent an alicyclic structure having 3 to 20 ring atoms together with the carbon atom to which $R^7$ and $R^8$ bond.

14. The resist pattern-forming method according to claim 7, wherein the leaving group is a group obtained by removing an acidic hydrogen atom from a hydrohalogenic acid or from a sulfonic acid.

15. The resist pattern-forming method according to claim 7, wherein the leaving group is a group obtained by removing an acidic hydrogen atom from a hydrohalogenic acid or from trifluoromethanesulfonic acid.

16. The resist pattern-forming method according to claim 5, wherein in the formula (1), in the definition of AO, the heteroarenediyl group is unsubstituted or substituted with a methyl group, tert-butyl group, a fluorine atom, or a cyano group; and in the definition of $Ar^2$, the aryl group and the heteroaryl group are each independently unsubstituted or substituted with a hydrogen atom, a halogen atom, a hydroxy group, a nitro group, an amino group, a fluorinated alkyl group, or an alkyl group.

17. A resist pattern-forming method comprising:
    applying the radiation-sensitive resin composition according to claim 5 on one face side of a substrate;
    exposing the resist film obtained after the applying; and
    developing the resist film exposed.

18. The resist pattern-forming method according to claim 17, wherein basicity of the first compound changes upon irradiation with a radioactive ray.

19. The resist pattern-forming method according to claim 17, wherein the first structural unit is a structural unit represented by formula (2), a structural unit that comprises an acetal structure or a combination thereof,

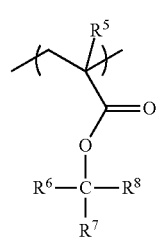

(2)

wherein, in the formula (2), $R^5$ represents a hydrogen atom, a fluorine atom, a methyl group or a trifluoromethyl group; $R^6$ represents a monovalent hydrocarbon group having 1 to 20 carbon atoms; and $R^7$ and $R^8$ each independently represent a monovalent hydrocarbon group having 1 to 20 carbon atoms, or $R^7$ and $R^8$ taken together represent an alicyclic structure having 3 to 20 ring atoms together with the carbon atom to which $R^7$ and $R^8$ bond.

20. The resist pattern-forming method according to claim 17, wherein the monovalent leaving group is a group obtained by removing an acidic hydrogen atom from a hydrohalogenic acid or from a sulfonic acid.

* * * * *